(12) United States Patent
Ohkura et al.

(10) Patent No.: US 12,279,523 B2
(45) Date of Patent: Apr. 15, 2025

(54) COMPOUND, HOLE TRANSPORT MATERIAL, AND PHOTOELECTRIC CONVERSION ELEMENT INCLUDING SAME

(71) Applicant: HODOGAYA CHEMICAL CO., LTD., Tokyo (JP)

(72) Inventors: Yuya Ohkura, Tokyo (JP); Hideaki Takahashi, Tokyo (JP); Hiroshi Sato, Tokyo (JP)

(73) Assignee: HODOGAYA CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 18/269,881

(22) PCT Filed: Jan. 11, 2022

(86) PCT No.: PCT/JP2022/000486
§ 371 (c)(1),
(2) Date: Jun. 27, 2023

(87) PCT Pub. No.: WO2022/153962
PCT Pub. Date: Jul. 21, 2022

(65) Prior Publication Data
US 2024/0099128 A1 Mar. 21, 2024

(30) Foreign Application Priority Data
Jan. 12, 2021 (JP) .................. 2021-002801

(51) Int. Cl.
*H10K 85/60* (2023.01)
*C07C 225/22* (2006.01)
*C07C 229/44* (2006.01)
*C07C 255/42* (2006.01)
(Continued)

(52) U.S. Cl.
CPC ......... *H10K 85/633* (2023.02); *C07C 225/22* (2013.01); *C07C 229/44* (2013.01);
(Continued)

(58) Field of Classification Search
CPC .. H10K 85/633; H10K 85/636; H10K 85/654; H10K 85/655; H10K 85/657;
(Continued)

(56) References Cited

U.S. PATENT DOCUMENTS

| 4,576,886 A | 3/1986 | Hirose et al. |
| 10,937,972 B2 | 3/2021 | Wakamiya et al. |

FOREIGN PATENT DOCUMENTS

| CN | 102214800 A | 10/2011 |
| CN | 106467485 A | 3/2017 |

(Continued)

OTHER PUBLICATIONS

CN 107046100A English machine translation (Year: 2011).*
(Continued)

*Primary Examiner* — Andrew J Golden
(74) *Attorney, Agent, or Firm* — Birch, Stewart, Kolasch & Birch, LLP

(57) ABSTRACT

An object of the present invention is to provide a compound that is useful as a hole transport material for providing a device for converting light into electricity that is capable of extracting current with high efficiency, and a device for converting light into electricity and a solar cell that include the compound in a hole transport layer and have favorable light/electricity conversion characteristics. The present invention provides a compound represented by the general formula (1) below. In the formula, $R^1$ to $R^{20}$ each represent a hydrogen atom, an alkoxy group having 1 to 20 carbon atoms, or the like, and Y represents an oxygen atom or $CR^{21}R^{22}$, where $R^{21}$ and $R^{22}$ each represent a nitrile group, an acyl group having 1 to 10 carbon atoms, or the like.

(Continued)

← 5 Counter electrode
← 4 Hole transport layer
← 3 Light/electricity conversion layer
← 2 Electron transport layer
← 1 Conductive support (1)

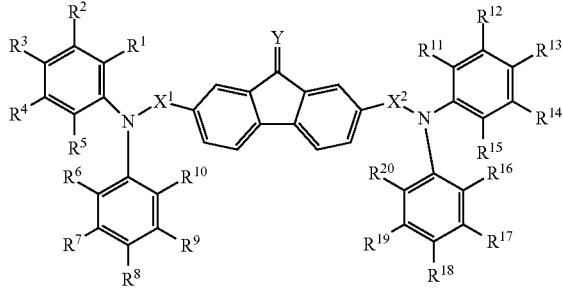

4 Claims, 1 Drawing Sheet

(51) Int. Cl.
 C07D 209/86 (2006.01)
 C07D 239/66 (2006.01)
 C07D 265/38 (2006.01)
 C07D 279/28 (2006.01)
 C07D 333/22 (2006.01)
 C07D 409/14 (2006.01)
 H10K 30/86 (2023.01)
(52) U.S. Cl.
 CPC .......... C07C 255/42 (2013.01); C07D 209/86 (2013.01); C07D 239/66 (2013.01); C07D 265/38 (2013.01); C07D 279/28 (2013.01); C07D 333/22 (2013.01); C07D 409/14 (2013.01); H10K 85/636 (2023.02); H10K 30/86 (2023.02); H10K 85/615 (2023.02); H10K 85/654 (2023.02); H10K 85/655 (2023.02); H10K 85/657 (2023.02); H10K 85/6572 (2023.02)
(58) Field of Classification Search
 CPC .. H10K 85/6572; H10K 85/615; H10K 30/86; C07C 225/22; C07C 229/44; C07C 255/42; C07D 209/86; C07D 239/66; C07D 265/38; C07D 279/28; C07D 333/22; C07D 409/14
 See application file for complete search history.

(56) References Cited

FOREIGN PATENT DOCUMENTS

| CN | 106467529 A | 3/2017 |
|---|---|---|
| CN | 107046100 A | 8/2017 |
| CN | 108586289 A | 9/2018 |
| CN | 108675941 A | 10/2018 |
| CN | 109180528 A | 1/2019 |
| CN | 109574917 A | 4/2019 |
| CN | 110627667 A | 12/2019 |
| CN | 113087726 A | 7/2021 |

OTHER PUBLICATIONS

CN 108586289A English machine translation (Year: 2018).*
Cao et al., "Efficient Perovskite Solar Cells with a Novel Aggregation-Induced Emission Molecule as Hole-Transport Material", Journal of Materials Chemistry C, vol. 4, No. 17, May 7, 2016, p. 3665-3874.
Gao et al., "p-Doped p-phenylenediamine-substituted fluorenes for organic electroluminescent devices", Organic Electronics, 2009, vol. 10, p. 666-673.
Hu et al., "Theoretical study of two-photon absorption properties and up-conversion efficiency of new symmetric organic Pi-conjugated molecules for photovoltaic devices", Journal of Molecular Modeling, 2012, vol. 18, No. 8, p. 3657-3667.
Huang et al., "A Cost-Effective D-A-D Type Hole-Transport Material Enabling 20% Efficiency Inverted Perovskite Solar Cells", Chinese Journal of Chemistry, 2021, vol. 39, No. 6, p. 1545-1552.
International Search Report, issued in PCT/JP2022/000486, PCT/ISA/210, dated Mar. 29, 2022.
Kojima et al., "Organometal Halide Perovskites as Visible-Light Sensitizers for Photovoltaic Cells", J. Am. Chem. Soc., 2009, vol. 131, p. 6050-6051.
Lee et al., Efficient Hybrid Solar Cells Based on Meso-Superstructured Organometal Halide Perovskites, Science, Nov. 2, 2012, vol. 338, p. 643-647.
Rakstys et al., "Efficiency vs. stability: dopant-free hole transporting materials towards stabilized perovskite solar cells", Chem. Sci., 2019, vol. 10, p. 6748-6769.
Wielopolski et al., "Synthesis and optoelectronic properties of chemically modified bi-fluorenylidenes", Journal of Materials Chemistry C: Materials for Optical and Electronic Devices, 2016, vol. 4, No. 17, p. 3798-3808.
Written Opinion of the International Searching Authority, issued in PCT/JP2022/000486, PCT/ISA/237, dated Mar. 29, 2022.
Yao et al., "Insights into molecular packing effects on the emission properties of fluorenone-based molecules in the aggregate state", Journal of Materials Chemistry C: Materials for Optical and Electronic Devices, Aug. 26, 2021, vol. 9, No. 39, p. 13687-13696. Abstract (3 pages).
Yu et al., "Dopant-free dicyanofluoranthene-based hole transporting material with low cost enables efficient flexible perovskite solar cells", Nano Energy 82 (2021), Dec. 16, 2020, 105701, total 10 pages.
Wang et al., "Boosting Non-Radiative Decay to Do Useful Work: Development of a Multi-Modality Theranostic System fom an AIEgen," Angewandte Chemie International Edition, vol. 58, 2019, pp. 5628-5632.

* cited by examiner

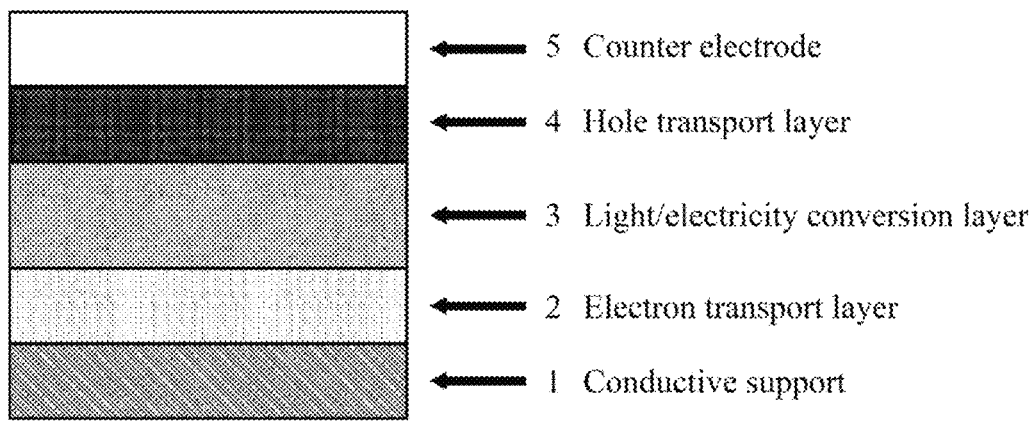

COMPOUND, HOLE TRANSPORT MATERIAL, AND PHOTOELECTRIC CONVERSION ELEMENT INCLUDING SAME

TECHNICAL FIELD

The present invention relates to a compound, a hole transport material, and a device for converting light into electricity, the device including the hole transport material.

BACKGROUND ART

In recent years, photovoltaic power generation has been gaining attention as a clean energy source, and solar cells has been actively developed. In particular, the development of solar cells having a perovskite material-containing layer to convert light into electricity (hereinafter referred to as "perovskite solar cells") is gaining attention (see Patent Literature 1 and Non-Patent Literatures 1 and 2, for example).

A hole transport material is often used in perovskite solar cells. The purposes of using the hole transport material include: (1) enhancing the ability to selectively transport holes to thereby improve the efficiency in conversion of light into electricity (i.e., power conversion efficiency), and (2) joining the hole transport material to the perovskite layer, which is for converting light into electricity, to thereby protect a perovskite material, which is susceptible to moisture and oxygen (see Non-Patent Literature 3, for example) (hereinafter, converting (or conversion of) light into electricity is also referred to as "light/electricity conversion"). A spirobifluorene-based organic compound Spiro-OMeTAD is often used as a standard hole transport material, and there have been few reports on a hole transport material that contributes more to light/electricity conversion characteristics than Spiro-OMeTAD.

CITATION LIST

Patent Literature

Patent Literature 1: U.S. Pat. No. 10,937,972B2

Non-Patent Literature

Non-Patent Literature 1: Journal of the American Chemical Society, 2009, Vol. 131, pp. 6050-6051
Non-Patent Literature 2: Science, 2012, Vol. 388, pp. 643-647
Non-Patent Literature 3: Chem. Sci., 2019, 10, pp. 6748-6769

SUMMARY OF INVENTION

It is an object of the present invention to provide a compound that is useful as a hole transport material for providing a device for converting light into electricity that is capable of extracting current with high efficiency, and a device for converting light into electricity and a solar cell that include the compound in a hole transport layer and have favorable light/electricity conversion characteristics.

To achieve the above-described object, the inventors of the present invention have conducted in-depth research on improving light/electricity conversion characteristics and have found that a device for converting light into electricity and a perovskite solar cell that exhibit high efficiency in conversion of light into electricity can be obtained by designing and developing a compound with a specific structure and using this compound as a hole transport layer in the device for converting light into electricity. Specifically, the present invention is summarized as follows.

1. A compound represented by the general formula (1) below.

[Chem. 1]

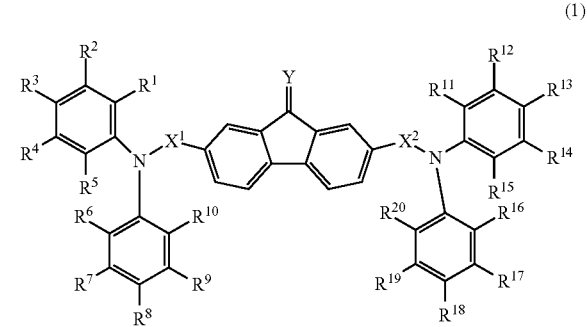

(1)

In this formula, $R^1$ to $R^{20}$ each independently represent a hydrogen atom, a halogen atom, a carboxyl group, a trimethylsilyl group, a linear or branched alkyl group having 1 to 20 carbon atoms and optionally having a substituent, a linear or branched alkenyl group having 2 to 20 carbon atoms and optionally having a substituent, a cycloalkyl group having 3 to 10 carbon atoms and optionally having a substituent, an alkyloxy group having 1 to 20 carbon atoms and optionally having a substituent, a cycloalkyloxy group having 3 to 10 carbon atoms and optionally having a substituent, an acyl group having 1 to 20 carbon atoms and optionally having a substituent, a thio group having 1 to 18 carbon atoms and optionally having a substituent, an amino group having 1 to 20 carbon atoms and optionally having a substituent, an aromatic hydrocarbon group having 6 to 36 carbon atoms and having a substituent, or a heterocyclic group having 5 to 36 ring-forming atoms and optionally having a substituent;

$R^1$ and $R^2$; $R^2$ and $R^3$; $R^3$ and $R^4$; $R^4$ and $R^5$; $R^6$ and $R^7$; $R^7$ and $R^8$; $R^8$ and $R^9$; $R^9$ and $R^{10}$; $R^{11}$ and $R^{12}$; $R^{12}$ and $R^{13}$; $R^{13}$ and $R^{14}$; $R^{14}$ and $R^{15}$; $R^{16}$ and $R^{17}$; $R^{17}$ and $R^{18}$; $R^{18}$ and $R^{19}$; and $R^{19}$ and $R^{20}$ are, in each combination, optionally bonded to each other to form a ring; and $R^5$ and $R^6$; and $R^{15}$ and $R^{16}$ are, in each combination, optionally bonded to each other to form a ring;

$X^1$ and $X^2$ each represent a divalent group; and

Y represents an oxygen atom or $CR^{21}R^{22}$, where $R^{21}$ and $R^{22}$ each independently represent a nitrile group, an acyl group having 1 to 10 carbon atoms and optionally having a substituent, or an alkoxycarbonyl group having 1 to 10 carbon atoms and optionally having a substituent, and $R^{21}$ and $R^{22}$ are optionally bonded to each other to form a ring.

2. The above-described compound, wherein, in the general formula (1), $X^1$ and $X^2$ are represented by the general formula (2) below.

[Chem. 2]

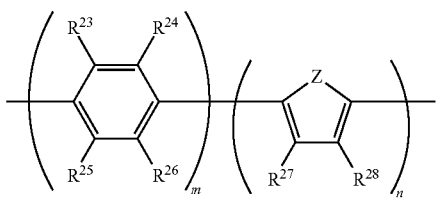

(2)

In this formula, $R^{23}$ to $R^{28}$ each independently represent a hydrogen atom, a linear or branched alkyl group having 1 to 10 carbon atoms and optionally having a substituent, a linear or branched alkenyl group having 2 to 10 carbon atoms and optionally having a substituent, a cycloalkyl group having 3 to 10 carbon atoms and optionally having a substituent, an aromatic hydrocarbon group having 6 to 18 carbon atoms and optionally having a substituent, or a heterocyclic group having 5 to 18 ring-forming atoms and optionally having a substituent;

$R^{23}$ and $R^{24}$; $R^{25}$ and $R^{26}$; and $R^{27}$ and $R^{28}$ are, in each combination, optionally bonded to each other to form a ring;

Z represents an oxygen atom, a sulfur atom, or a selenium atom; and m and n represent integers of 0 to 2, with the proviso that cases where both m and n are 0 are excluded.

3. The above-described compound, wherein, in the general formula (2), m is 1.

4. The above-described compound, wherein, in the general formula (1), $R^1$ to $R^{20}$ are each independently a hydrogen atom, a linear or branched alkyl group having 1 to 20 carbon atoms and optionally having a substituent, an alkoxy group having 1 to 20 carbon atoms and optionally having a substituent, a thio group having 1 to 18 carbon atoms and optionally having a substituent, or an amino group having 1 to 20 carbon atoms and optionally having a substituent.

5. A hole transport material including the above-described compound.

6. A device for converting light into electricity, including the above-described hole transport material.

The compound and the hole transport layer including the compound according to the present invention enable a device for converting light into electricity and a perovskite solar cell that have favorable power conversion efficiency.

BRIEF DESCRIPTION OF DRAWING

FIG. 1 is a schematic cross-sectional view showing the configuration of the devices for converting light into electricity of Examples and Comparative Examples.

DESCRIPTION OF EMBODIMENTS

Embodiments of the present invention will be described in detail below. The hole transport material of the present invention is suitably used for a device for converting light into electricity and a perovskite solar cell.

Device for Converting Light into Electricity

As shown in the schematic cross-sectional view of FIG. 1, a device for converting light into electricity of the present invention (hereinafter, also simply referred to as "the device of the present invention") typically has a conductive support 1; an electron transport layer 2; a layer that convers light into electricity (hereinafter also referred to as "light/electricity conversion layer"), 3; a hole transport layer 4; and a counter electrode 5.

Hereinafter, a compound represented by the general formula (1) above, which serves as a hole transport material for use in the hole transport layer of the device of the present invention, will be described specifically, but the present invention is not limited to the following descriptions.

$R^1$ to $R^{20}$ in the general formula (1) each independently represent a hydrogen atom, a halogen atom, a carboxyl group, a trimethylsilyl group, a linear or branched alkyl group having 1 to 20 carbon atoms and optionally having a substituent, a linear or branched alkenyl group having 2 to 20 carbon atoms and optionally having a substituent, a cycloalkyl group having 3 to 10 carbon atoms and optionally having a substituent, an alkyloxy group having 1 to 20 carbon atoms and optionally having a substituent, a cycloalkyloxy group having 3 to 10 carbon atoms and optionally having a substituent, an acyl group having 1 to 20 carbon atoms and optionally having a substituent, a thio group having 1 to 18 carbon atoms and optionally having a substituent, an amino group having 1 to 20 carbon atoms and optionally having a substituent, an aromatic hydrocarbon group having 6 to 36 carbon atoms and having a substituent, or a heterocyclic group having 5 to 36 ring-forming atoms and optionally having a substituent.

Examples of the "halogen atom" represented by $R^1$ to $R^{20}$ include fluorine, chlorine, bromine, and iodine.

Examples of the "linear or branched alkyl group having 1 to 20 carbon atoms" of the "linear or branched alkyl group having 1 to 20 carbon atoms and optionally having a substituent" represented by $R^1$ to $R^{20}$ include: a methyl group, an ethyl group, an n-propyl group, an isopropyl group, an n-butyl group, an isobutyl group, an s-butyl group, a t-butyl group, an n-pentyl group, an isopentyl group, an n-hexyl group, a 2-ethylhexyl group, a heptyl group, an octyl group, an isooctyl group, a nonyl group, and a decyl group.

Examples of the "linear or branched alkenyl group having 2 to 20 carbon atoms" of the "linear or branched alkenyl group having 2 to 20 carbon atoms and optionally having a substituent" represented by $R^1$ to $R^{20}$ include: an ethenyl group (vinyl group), a 1-propenyl group, a 2-propenyl group (allyl group), a 1-methylethenyl group, a 1-butenyl group, a 2-butenyl group, a 1-pentenyl group, a 1-hexenyl group, a 2-methyl-1-propenyl group, a 2-methyl-2-propenyl group, and a 1-ethylethenyl group, and also a linear or branched alkenyl group having 2 to 20 carbon atoms that is composed of a plurality of these alkenyl groups linked together.

Examples of the "cycloalkyl group having 3 to 10 carbon atoms" of the "cycloalkyl group having 3 to 10 carbon atoms and optionally having a substituent" represented by $R^1$ to $R^{20}$ include: a cyclopropyl group, a cyclobutyl group, a cyclopentyl group, a cyclohexyl group, a cycloheptyl group, a cyclooctyl group, a cyclodecyl group, a cyclododecyl group, a 4-methylcyclohexyl group, and a 4-ethylcyclohexyl group.

Examples of the "alkoxy group having 1 to 20 carbon atoms" of the "alkoxy group having 1 to 20 carbon atoms and optionally having a substituent" represented by $R^1$ to $R^{20}$ include: a methoxy group, an ethoxy group, a propoxy group, an n-butoxy group, an n-pentyloxy group, an n-hexyloxy group, a heptyloxy group, an octyloxy group, a nonyloxy group, a decyloxy group, an isopropoxy group, an isobutoxy group, an s-butoxy group, a t-butoxy group, an isooctyloxy group, a t-octyloxy group, a phenoxy group, a tolyloxy group, a biphenylyloxy group, a terphenylyloxy group, a naphthyloxy group, an anthryloxy group, a phenanthryloxy group, a fluorenyloxy group, and an indenyloxy group.

Examples of the "cycloalkyloxy group having 3 to 10 carbon atoms" of the "linear or branched cycloalkyloxy group having 3 to 10 carbon atoms and optionally having a substituent" represented by $R^1$ to $R^{20}$ include: a cyclopropoxy group, a cyclobutoxy group, a cyclopentyloxy group, a cyclohexyloxy group, and a 4-methylcyclohexyloxy group.

Examples of the "acyl group having 1 to 20 carbon atoms" of the "acyl group having 1 to 20 carbon atoms and optionally having a substituent" represented by $R^1$ to $R^{20}$ include: an acetyl group, a propionyl group, a butyryl group, an isobutyryl group, a valeryl group, an isovaleryl group, a benzoylacetyl group, and a benzoyl group. One or more hydrogen atoms of the alkyl group in the acyl group may be replaced with fluorine atoms, and all of the hydrogen atoms may be replaced with fluorine atoms (that is, perfluorinated). The acyl group may be bonded to an amino group (—CO—N<).

Examples of the "thio group having 1 to 18 carbon atoms" of the "thio group having 1 to 18 carbon atoms and optionally having a substituent" represented by $R^1$ to $R^{20}$ include: a methylthio group, an ethylthio group, a propylthio group, a phenylthio group, and a biphenylthio group.

Examples of the "amino group having 1 to 20 carbon atoms" of the "amino group having 1 to 20 carbon atoms and optionally having a substituent" represented by $R^1$ to $R^{20}$ include: mono-substituted amino groups such as an ethylamino group, an acetylamino group, and a phenylamino group; and di-substituted amino groups such as a diethylamino group, a diphenylamino group, and an acetylphenylamino group.

Examples of the "aromatic hydrocarbon group having 6 to 36 carbon atoms" of the "aromatic hydrocarbon group having 6 to 36 carbon atoms and optionally having a substituent" represented by $R^1$ to $R^{20}$ include: a phenyl group, a biphenyl group, a terphenyl group, a naphthyl group, a biphenyl group, an anthracenyl group (anthryl group), a phenanthryl group, a fluorenyl group, an indenyl group, a pyrenyl group, a perylenyl group, a fluoranthenyl group, and a triphenylenyl group. In the present invention, the aromatic hydrocarbon group encompasses a "fused polycyclic aromatic group".

Examples of the "heterocyclic group having 5 to 36 ring-forming atoms" of the "heterocyclic group having 5 to 36 ring-forming atoms and optionally having a sub stituent" represented by $R^1$ to $R^{20}$ include: a pyridyl group, a pyrimidinyl group, a triazinyl group, a thienyl group, a furyl group (furanyl group), a pyrrolyl group, an imidazolyl group, a pyrazolyl group, a triazolyl group, a quinolyl group, an isoquinolyl group, a naphthyldinyl group, an acridinyl group, a phenanthrolinyl group, a benzofuranyl group, a benzothienyl group, an oxazolyl group, an indolyl group, a carbazolyl group, a benzoxazolyl group, a thiazolyl group, a benzothiazolyl group, a quinoxalinyl group, a benzimidazolyl group, a pyrazolyl group, a dibenzofuranyl group, a dibenzothienyl group, and a carbonylyl group.

Examples of the "substituent" of the "linear or branched alkyl group having 1 to 18 carbon atoms and optionally having a substituent", the "linear or branched alkenyl group having 2 to 20 carbon atoms and optionally having a substituent", the "cycloalkyl group having 3 to 10 carbon atoms and optionally having a substituent", the "alkyloxy group having 1 to 20 carbon atoms and optionally having a substituent", the "cycloalkyloxy group having 3 to 10 carbon atoms and optionally having a substituent", the "acyl group having 1 to 20 carbon atoms and optionally having a substituent", the "thio group having 1 to 18 carbon atoms and optionally having a substituent", the "amino group having 1 to 20 carbon atoms and optionally having a substituent", the "aromatic hydrocarbon group having 6 to 36 carbon atoms and having a sub stituent", or the "heterocyclic group having 5 to 36 ring-forming atoms and optionally having a substituent" include: halogen atoms such as a fluorine atom, a chlorine atom, a bromine atom, and an iodine atom; a cyano group; a hydroxyl group; a nitro group; a nitroso group; a carboxyl group; a phosphate group: a thioxo group (>C=S); a trimethylsilyl group; carboxylic acid ester groups such as methyl ester groups and ethyl ester groups; linear or branched alkyl groups having 1 to 18 carbon atoms such as a methyl group, an ethyl group, an n-propyl group, an isopropyl group, an n-butyl group, an isobutyl group, an s-butyl group, a t-butyl group, an n-pentyl group, an isopentyl group, an n-hexyl group, a 2-ethylhexyl group, a heptyl group, an octyl group, an isooctyl group, a nonyl group, and a decyl group; linear or branched alkenyl groups having 2 to 18 carbon atoms such as an ethenyl group (vinyl group), a 1-propenyl group, a 2-propenyl group (allyl group), a 1-butenyl group, a 2-butenyl group, a 1-pentenyl group, a 1-hexenyl group, a 2-methyl-1-propenyl group, a 2-methyl-2-propenyl group, and a 1-ethylethenyl group; alkoxy groups having 1 to 18 carbon atoms such as a methoxy group, an ethoxy group, a propoxy group, a t-butoxy group, a pentyloxy group, and a hexyloxy group; aromatic hydrocarbon groups having 6 to 30 carbon atoms such as a phenyl group, a naphthyl group, an anthryl group, a phenanthryl group, and a pyrenyl group; heterocyclic groups having 5 to 30 ring-forming atoms such as a pyridyl group, a pyrimidinyl group, a triazinyl group, a thienyl group, a furyl group (furanyl group), a pyrrolyl group, an imidazolyl group, a pyrazolyl group, a triazolyl group, a quinolyl group, an isoquinolyl group, a naphthyldinyl group, an acridinyl group, a phenanthrolinyl group, a benzofuranyl group, a benzothienyl groups, an oxazolyl group, an indolyl group, a carbazolyl group, a benzooxazolyl group, a thiazolyl group, a benzothiazolyl group, a quinoxalinyl group, a benzimidazolyl group, a pyrazolyl group, a dibenzofuranyl group, a dibenzothienyl group, and a carbonylyl group; amino groups having 0 to 18 carbon atoms such as an unsubstituted amino group (—$NH_2$), mono-substituted amino groups such as an ethylamino group, an acetylamino group, and a phenylamino group, and di-substituted amino groups such as a diethylamino group, a diphenylamino group, and an acetylphenylamino group; and thio groups having 0 to 18 carbon atoms such as an unsubstituted thio group (thiol group: —SH), a methylthio group, an ethylthio group, a propylthio group, a phenylthio group, and a biphenylthio groups. A plurality of "substituents" as described above may be contained, and when a plurality of substituents are contained, the substituents may be the same or different. These "substituents" may further have any of the substituents as listed above.

In the present invention, $R^1$ to $R^{20}$ are, each independently, preferably a hydrogen atom, a linear or branched alkyl group having 1 to 20 carbon atoms and optionally having a substituent, an alkoxy group having 1 to 20 carbon atoms and optionally having a substituent, a thio group having 1 to 18 carbon atoms and optionally having a substituent, or an amino group having 1 to 20 carbon atoms and optionally having a substituent, and more preferably a hydrogen atom or an alkoxy group having 1 to 10 carbon atoms. In particular, it is preferable that $R^1$, $R^2$, $R^4$, $R^5$, $R^6$, $R^7$, $R^9$, $R^{10}$, $R^{11}$, $R^{12}$, $R^{14}$, $R^{15}$, $R^{16}$, $R^{17}$, $R^{19}$, and $R^{20}$ are hydrogen atoms, and at the same time, that $R^3$, $R^8$, $R^{13}$, and $R^{18}$ are alkoxy groups having 1 to 10 carbon atoms, in view of favorable power conversion efficiency when used as a hole transport material in a device for converting light into electricity.

In the present invention, $R^1$ and $R^2$; $R^2$ and $R^3$; $R^3$ and $R^4$; $R^4$ and $R^5$; $R^6$ and $R^7$; $R^7$ and $R^8$; $R^8$ and $R^9$; $R^9$ and $R^{10}$; $R^{11}$ and $R^{12}$; $R^{12}$ and $R^{13}$; $R^{13}$ and $R^{14}$; $R^{14}$ and $R^{15}$; $R^{16}$ and $R^{17}$; $R^{17}$ and $R^{18}$; $R^{18}$ and $R^{19}$; and $R^{19}$ and $R^{20}$ may be, in each combination, bonded to each other to form a ring via a single bond, an oxygen atom, a sulfur atom, a selenium atom, or a nitrogen atom. $R^5$ and $R^6$; and $R^{15}$ and $R^{16}$ may also be, in each combination, bonded to each other to form a ring via a single bond, an oxygen atom, a sulfur atom, a selenium atom, or a nitrogen atom. When $R^5$ and $R^6$, and/or $R^{15}$ and $R^{16}$ form rings, the members in each combination are preferably bonded to each other to form a ring via a single bond, an oxygen atom, or a sulfur atom, and more preferably bonded to each other to form a ring via a single bond.

In the present invention, Y represents an oxygen atom or $CR^{21}R^{22}$, where $R^{21}$ and $R^{22}$ each independently represent a nitrile group, an acyl group having 1 to 10 carbon atoms and optionally having a substituent, or an alkoxycarbonyl group having 1 to 10 carbon atoms and optionally having a substituent, and are preferably electron-withdrawing groups.

Examples of the "acyl group having 1 to 10 carbon atoms and optionally having a substituent" represented by $R^{21}$ and $R^{22}$ include those having 1 to 10 carbon atoms, among the above-listed examples of the "acyl group having 1 to 20 carbon atoms and optionally having a substituent" represented by $R^1$ to $R^{20}$.

Examples of the "alkoxycarbonyl group having 1 to 10 carbon atoms" of the "alkoxycarbonyl group having 1 to 10 carbon atoms and optionally having a substituent" represented by $R^{21}$ and $R^{22}$ include a methoxycarbonyl group and an ethoxycarbonyl group. One or more hydrogen atoms of the alkyl group in the alkoxycarbonyl group may be replaced with fluorine atoms, and all of the hydrogen atoms may be replaced with fluorine atoms (that is, perfluorinated).

$R^{21}$ and $R^{22}$ may be bonded to each other to form a ring via a single bond, an oxygen atom, a sulfur atom, a selenium atom, or a nitrogen atom. When $R^{21}$ and $R^{22}$ from a ring, the ring is preferably an acidic heterocyclic ring such as a barbituric acid ring, a thiobarbituric acid ring, or an indanedione ring.

In the present invention, it is preferable that $X^1$ and $X^2$ in the general formula (1) each should be a divalent group represented by the general formula (2) above, in view of favorable power conversion efficiency when the compound is used as a hole transport material in a device for converting light into electricity.

$R^{23}$ to $R^{28}$ in the general formula (2) each independently represent a hydrogen atom, a linear or branched alkyl group having 1 to 10 carbon atoms and optionally having a substituent, a linear or branched alkenyl group having 2 to 10 carbon atoms and optionally having a substituent, a cycloalkyl group having 3 to 10 carbon atoms and optionally having a substituent, an aromatic hydrocarbon group having 6 to 18 carbon atoms and optionally having a substituent, or a heterocyclic group having 5 to 18 ring-forming atoms and optionally having a substituent.

Examples of the "linear or branched alkyl group having 1 to 10 carbon atoms and optionally having a substituent" represented by $R^{23}$ to $R^{28}$ include those having 1 to 10 carbon atoms, among the above-listed examples of the "linear or branched alkyl group having 1 to 20 carbon atoms and optionally having a substituent" represented by $R^1$ to $R^{20}$.

Examples of the "linear or branched alkenyl group having 2 to 10 carbon atoms and optionally having a substituent" represented by $R^{23}$ to $R^{28}$ include those having 2 to 10 carbon atoms, among the above-listed examples of the "linear or branched alkenyl group having 2 to 20 carbon atoms and optionally having a substituent" represented by $R^1$ to $R^{20}$.

Examples of the "cycloalkyl group having 3 to 10 carbon atoms and optionally having a substituent" represented by $R^{23}$ to $R^{28}$ include those listed above as examples of the "cycloalkyl group having 3 to 10 carbon atoms and optionally having a substituent" represented by $R^1$ to $R^{20}$.

Examples of the "aromatic hydrocarbon group having 6 to 18 carbon atoms and optionally having a sub stituent" represented by $R^{23}$ to $R^{28}$ include those having 6 to 18 carbon atoms, among the above-listed examples of the "aromatic hydrocarbon group having 6 to 36 carbon atoms and optionally having a substituent" represented by $R^1$ to $R^{20}$.

Examples of the "heterocyclic group having 5 to 18 ring-forming atoms and optionally having a substituent" represented by $R^{23}$ to $R^{28}$ include those having 5 to 18 ring-forming atoms, among the above-listed examples of the "heterocyclic group having 5 to 36 ring-forming atoms and optionally having a substituent" represented by $R^1$ to $R^{20}$.

$R^{23}$ and $R^{24}$; $R^{25}$ and $R^{26}$; and $R^{27}$ and $R^{28}$ may be, in each combination, bonded to each other to form a ring via a single bond, an oxygen atom, a sulfur atom, a selenium atom, or a nitrogen atom.

Z in the general formula (2) represents an oxygen atom, a sulfur atom, or a selenium atom.

In the present invention, Z is preferably a sulfur atom.

m and n in the general formula (2) represent integers of 0 to 2; with the proviso that, when m is 0, n is 1 or 2, and when n is 0, m is 1 or 2. In other words, cases where both m and n are 0 are excluded. m is preferably 1. n is preferably 0 or 1. The group represented by the general formula (2) may be bonded, at its moiety of the phenyl group or at its moiety of the five-membered heterocyclic group, to the fluorenone moiety serving as the central skeleton of the general formula (1).

Specific examples of the compound represented by the general formula (1) of the present invention are given below, but the present invention is not limited to these examples. The compounds illustrated below are shown with a plurality of hydrogen atoms, carbon atoms, and others omitted. The compounds illustrated below each merely represent an exemplar among possible isomers and should be construed to encompass all of the other isomers. The compounds each may be a mixture of two or more isomers.

[Chem. 3]
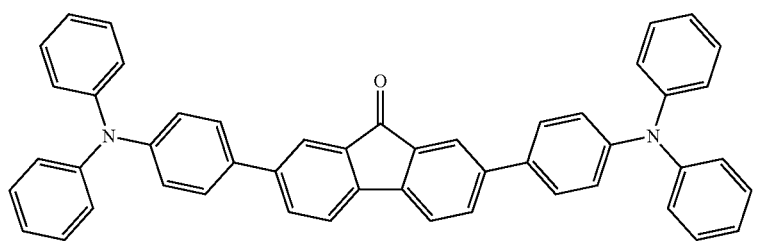
(A-1)
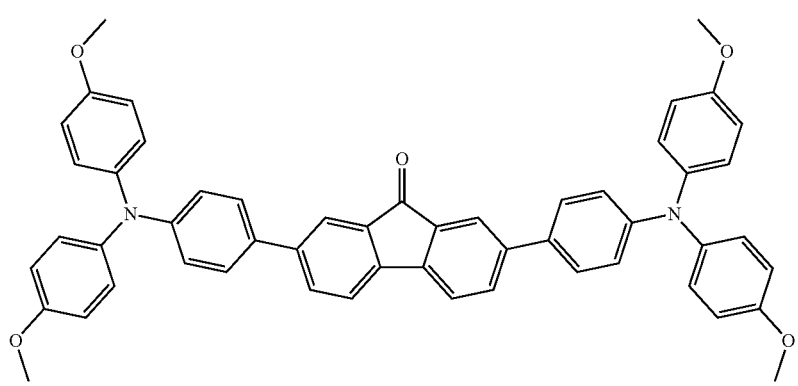
(A-2)
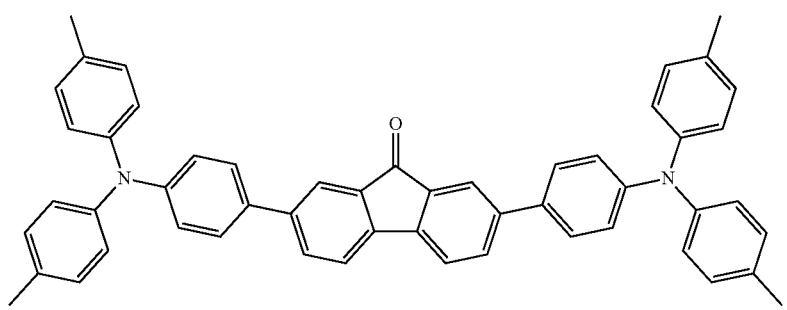
(A-3)
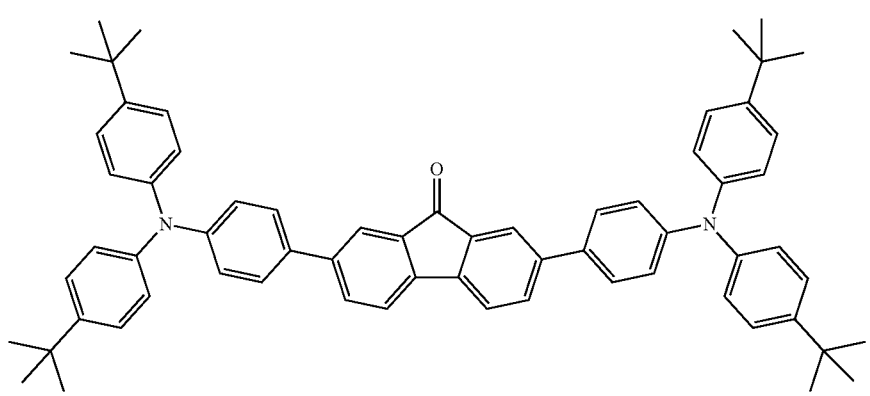
(A-4)

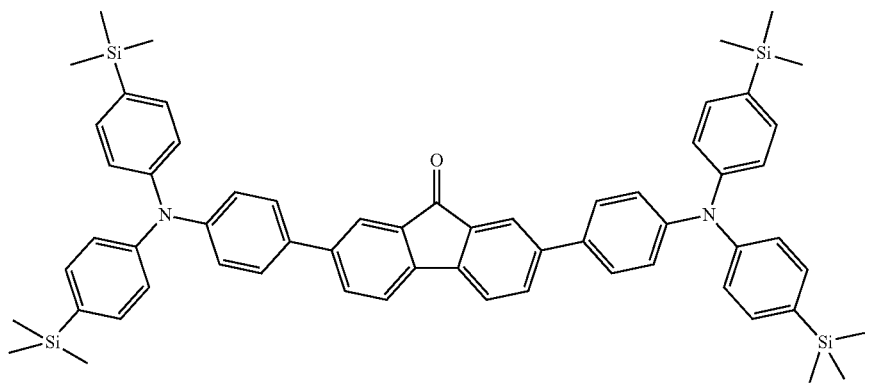
(A-5)
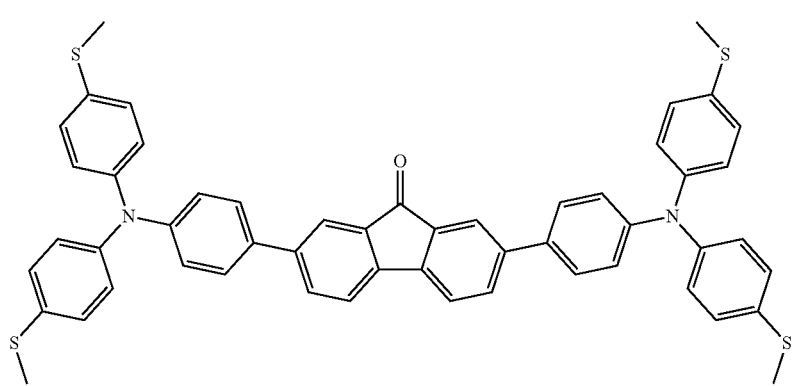
(A-6)
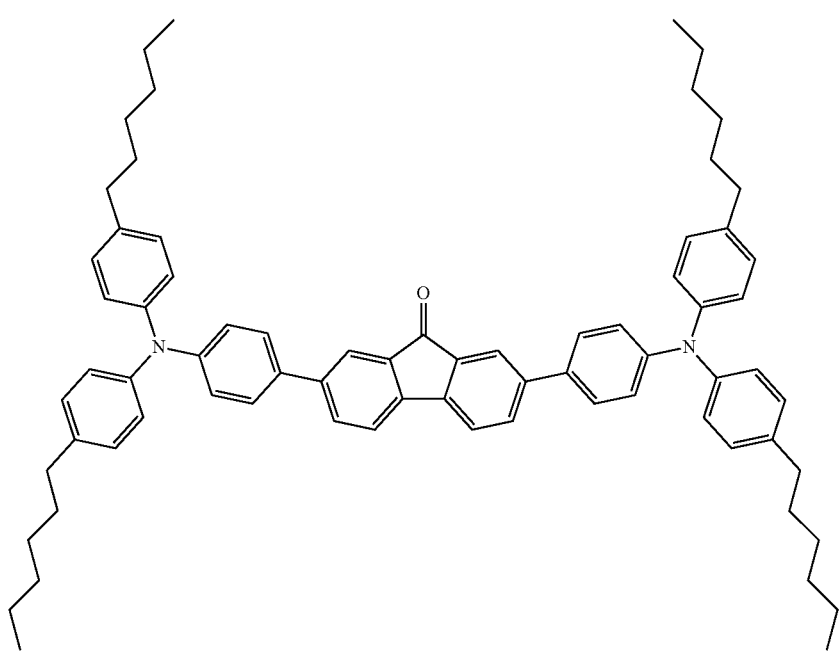
(A-7)

-continued
(A-8)
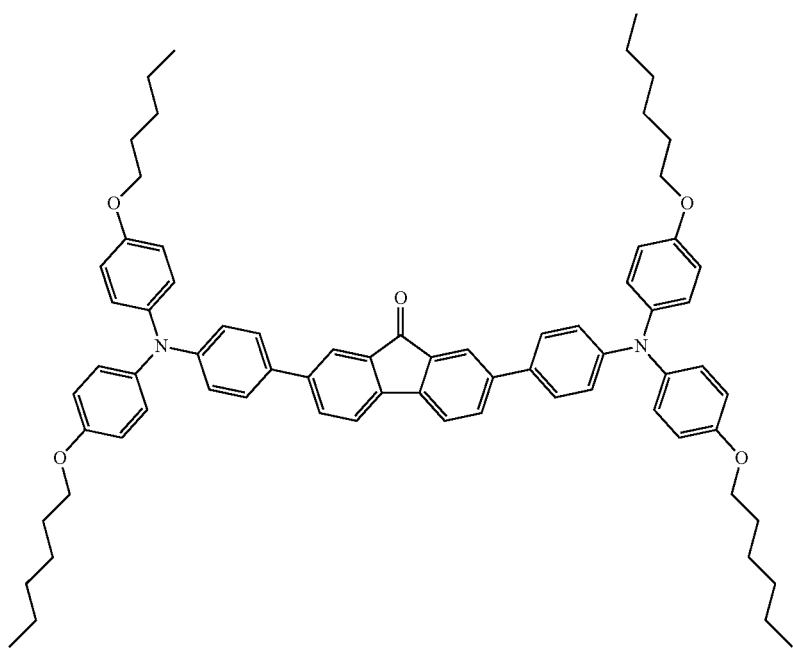
(A-9)
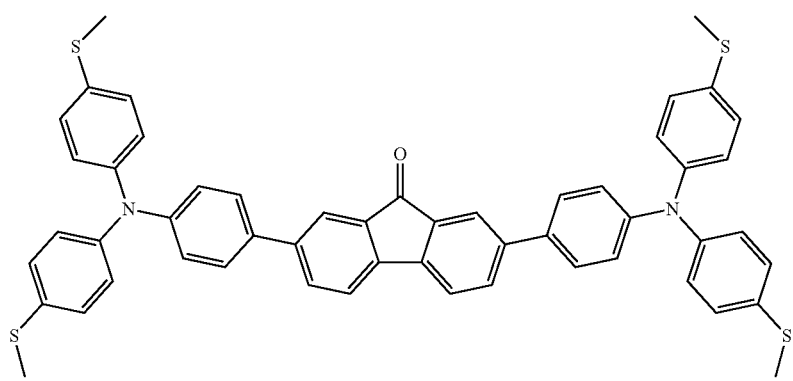
(A-10)
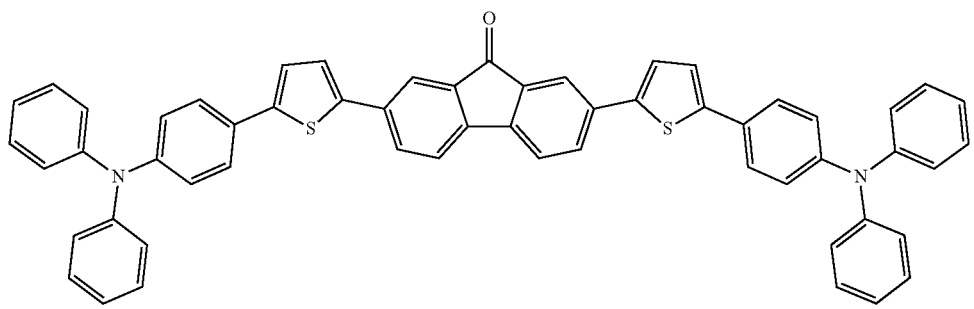

-continued
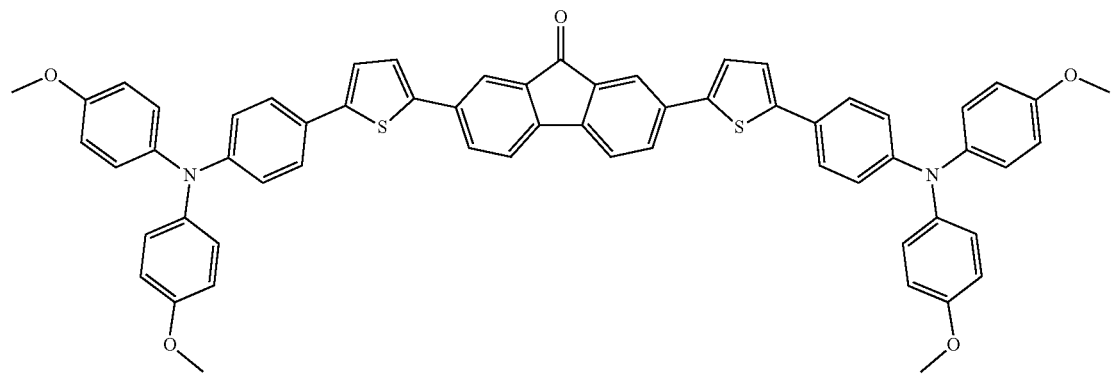
(A-11)
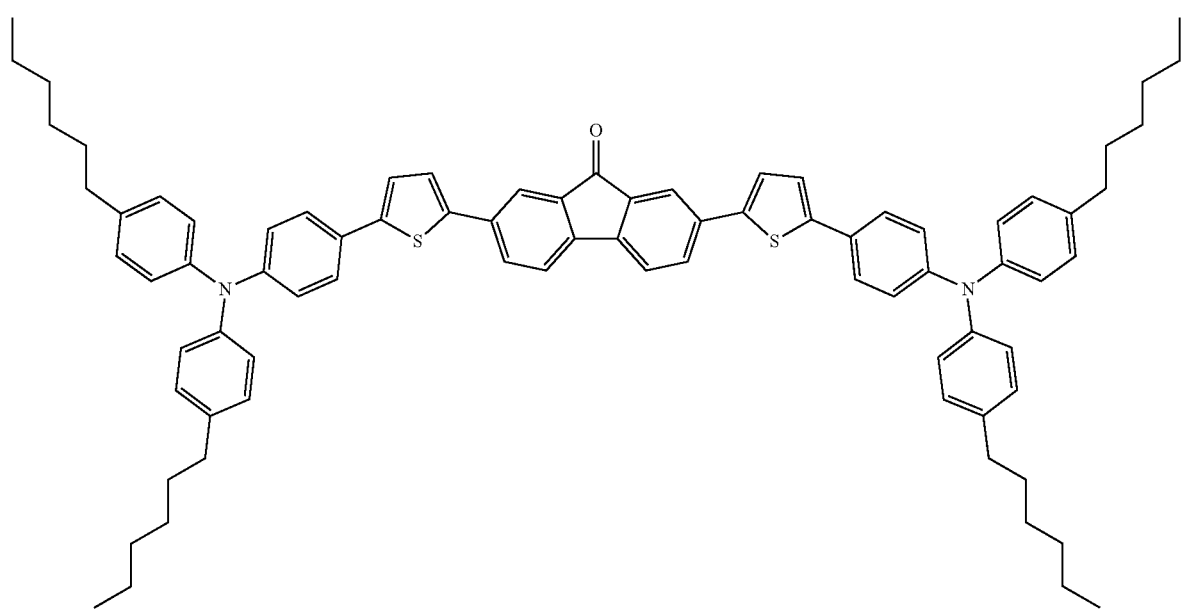
(A-12)
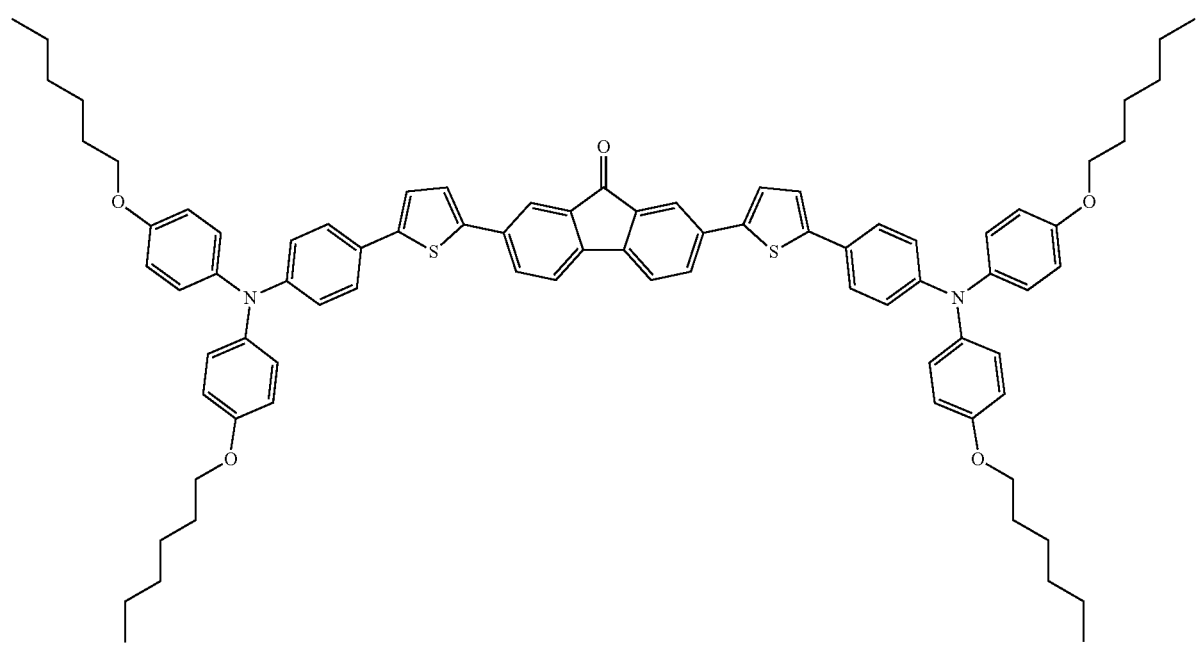
(A-13)

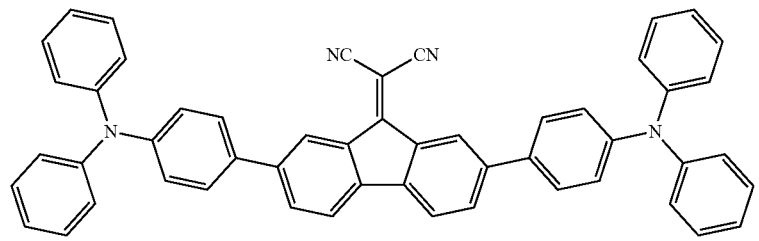
(A-14)
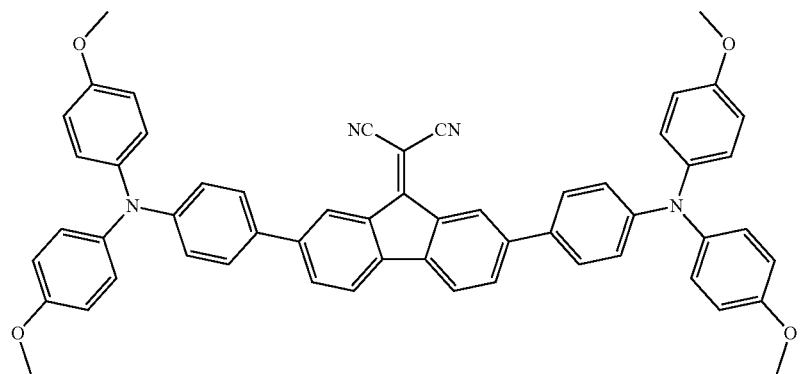
(A-15)
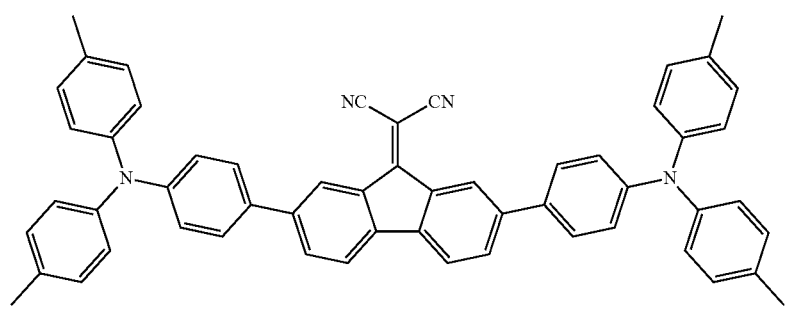
(A-16)
[Chem. 4]
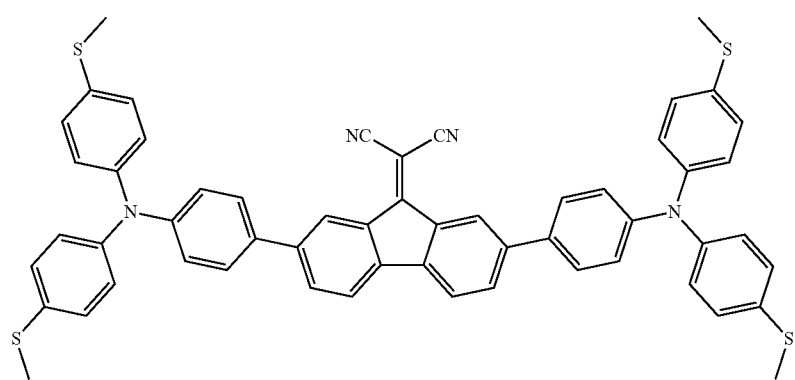
(A-17)

-continued
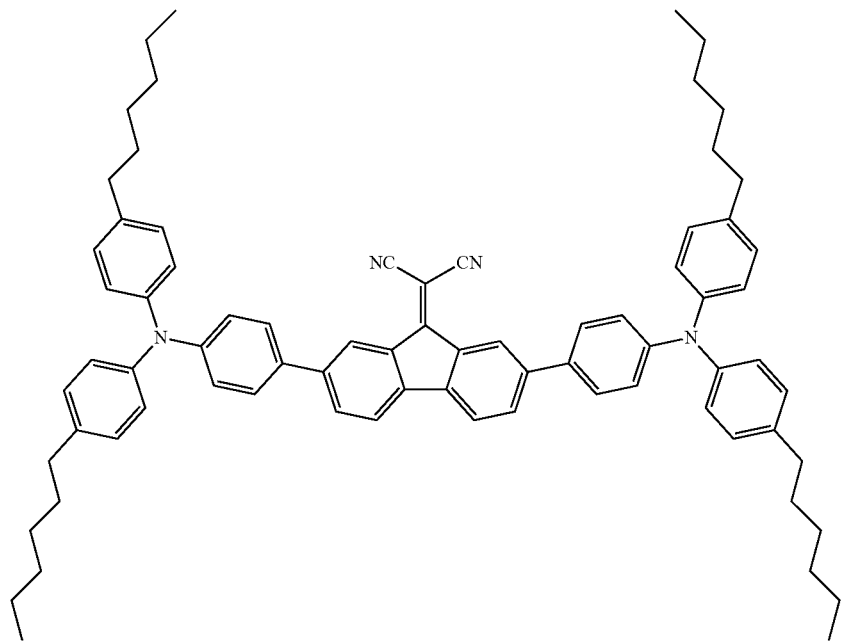
(A-18)
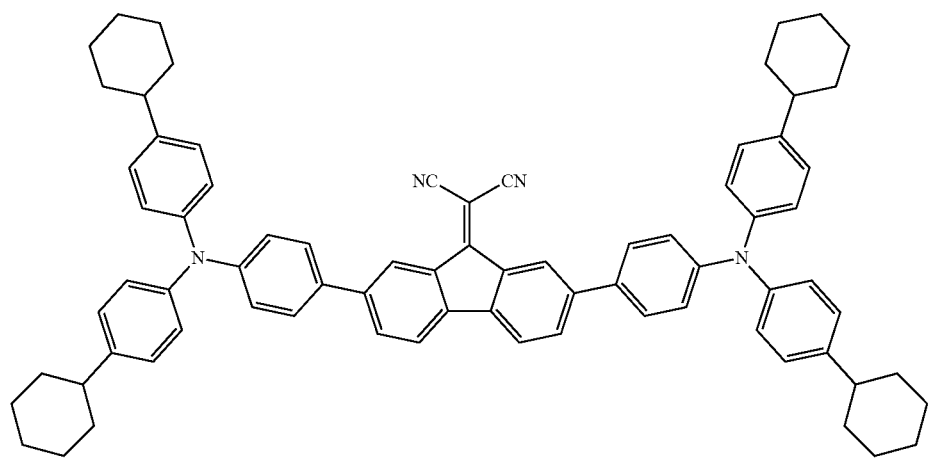
(A-19)

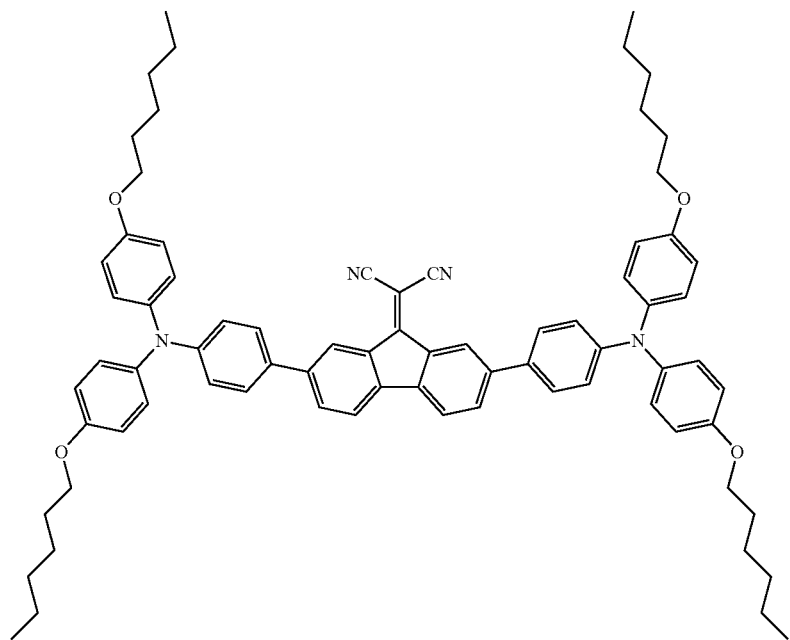
(A-20)
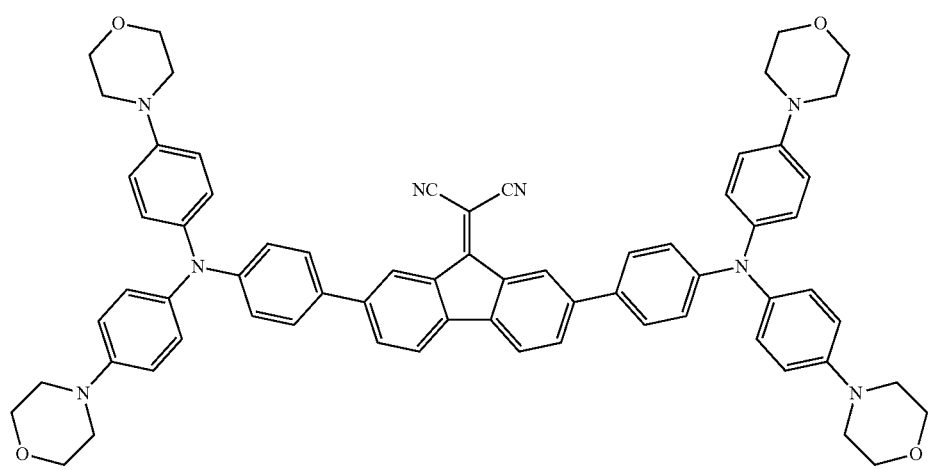
(A-21)
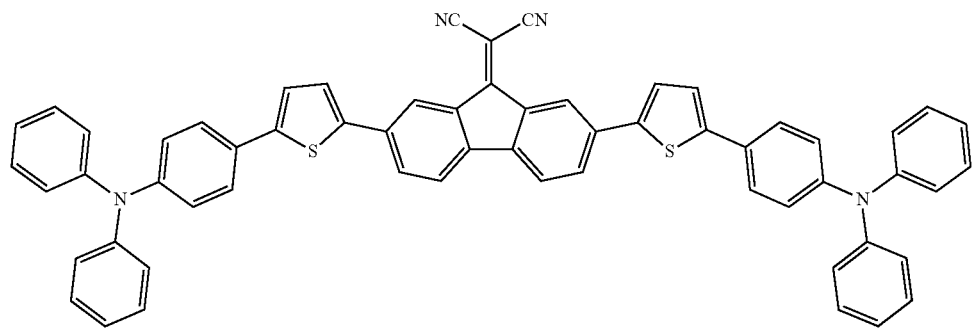
(A-22)

-continued
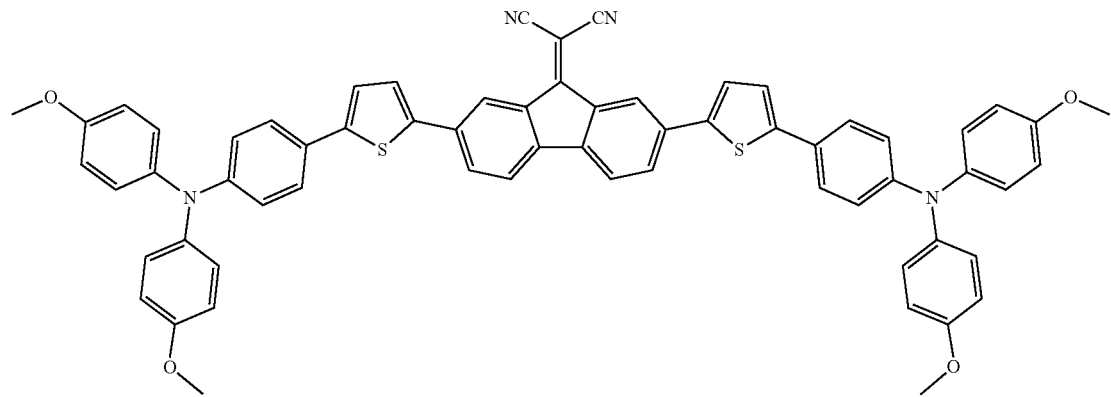
(A-23)
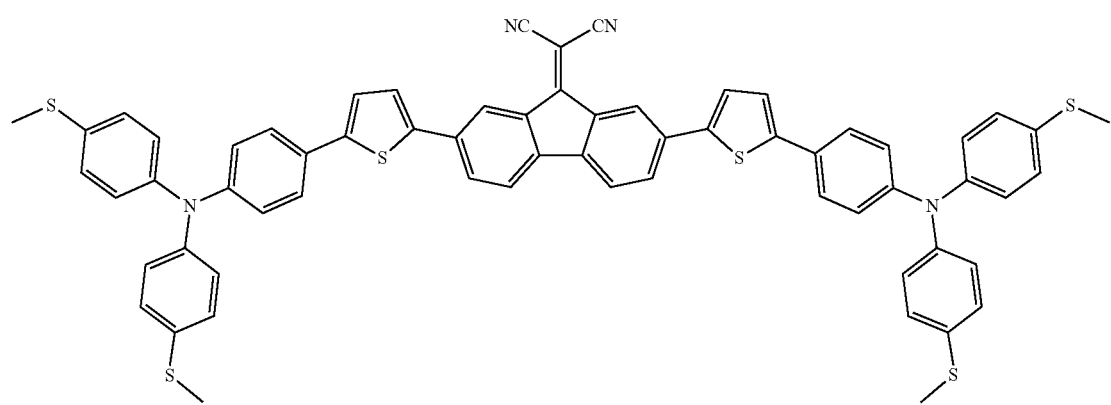
(A-24)
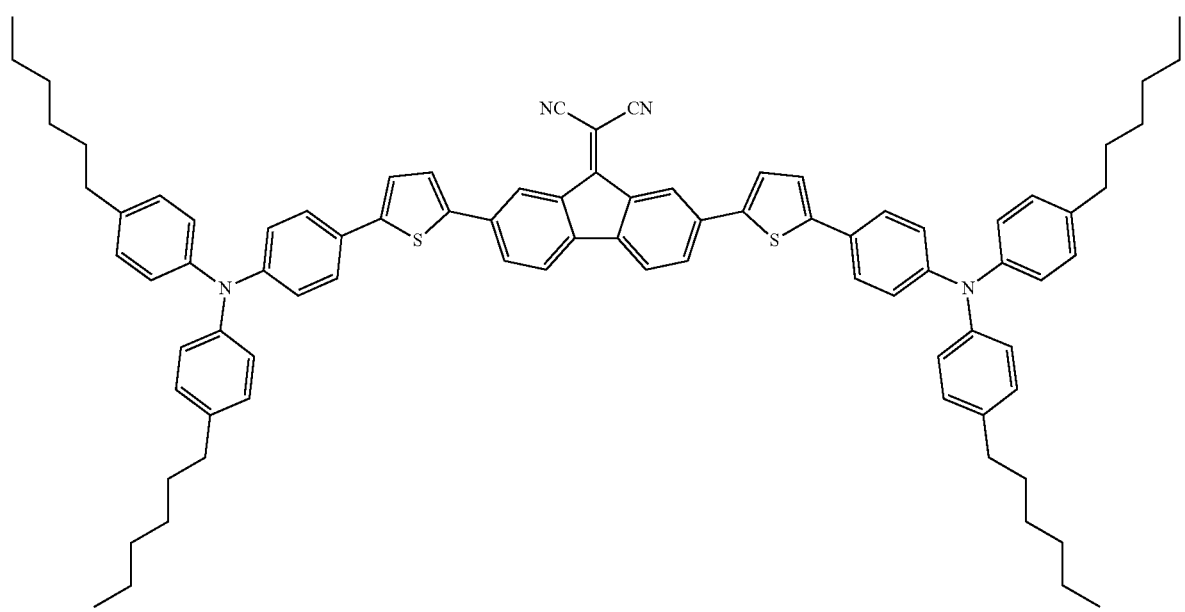
(A-25)

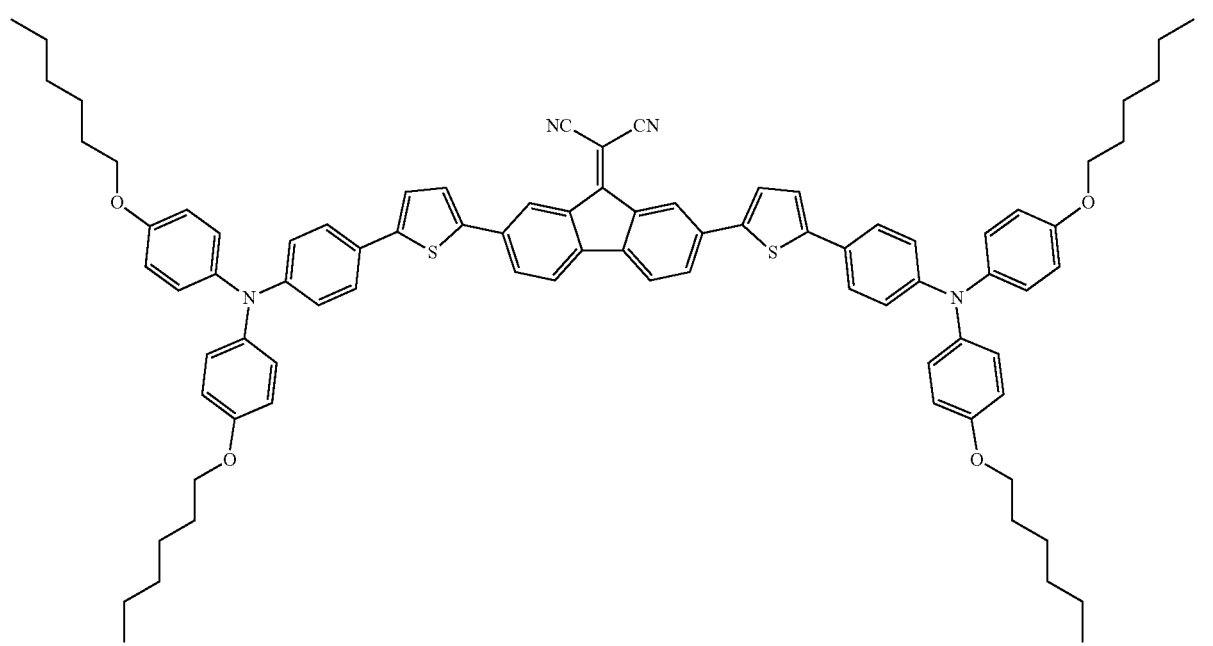
(A-26)
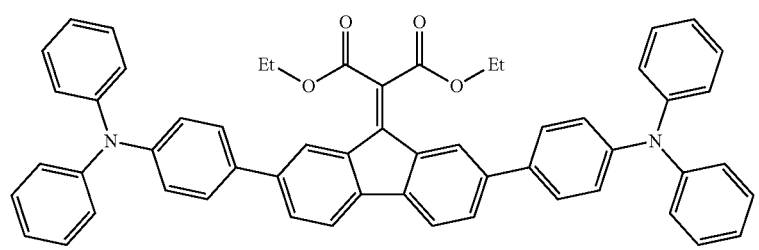
(A-27)
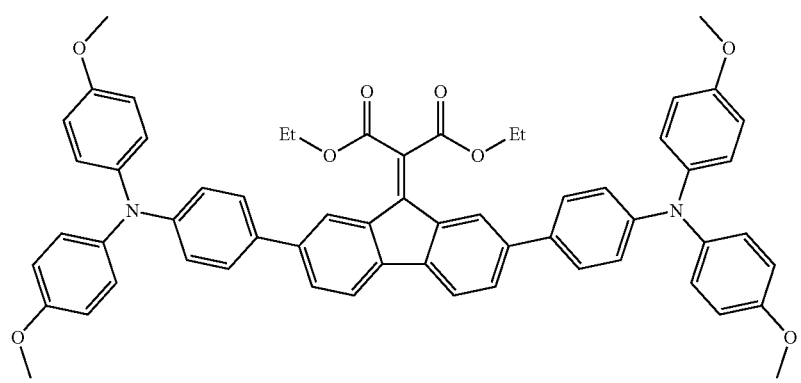
(A-28)
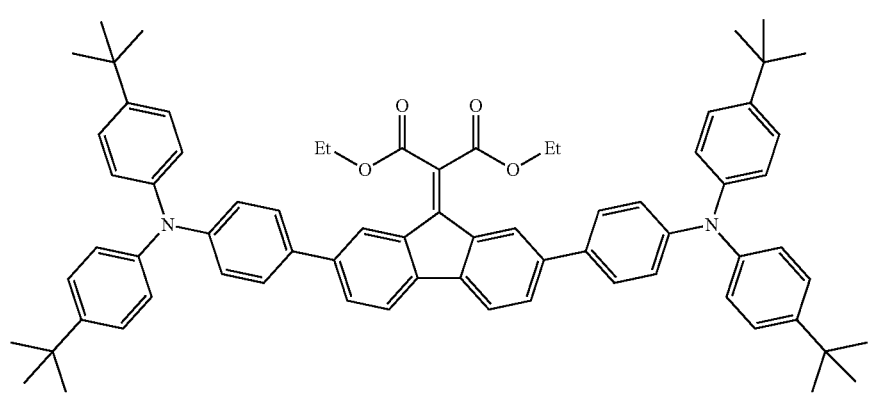
(A-29)

(A-30)
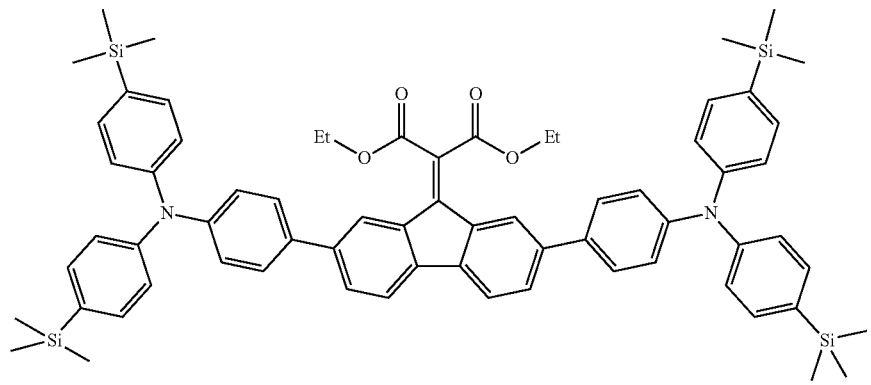
(A-31)
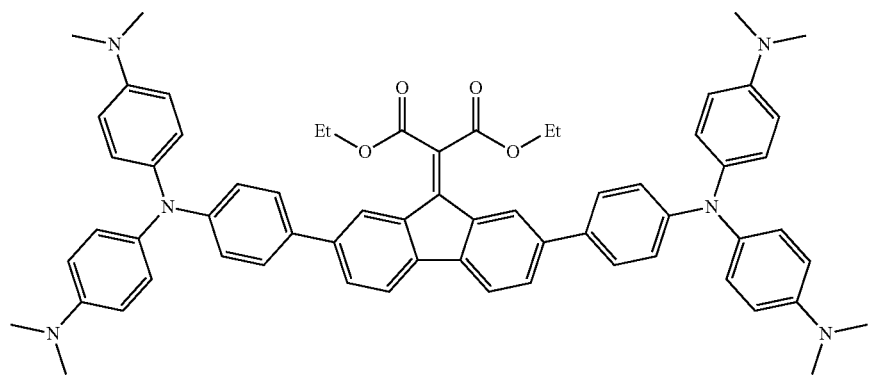
(A-32)
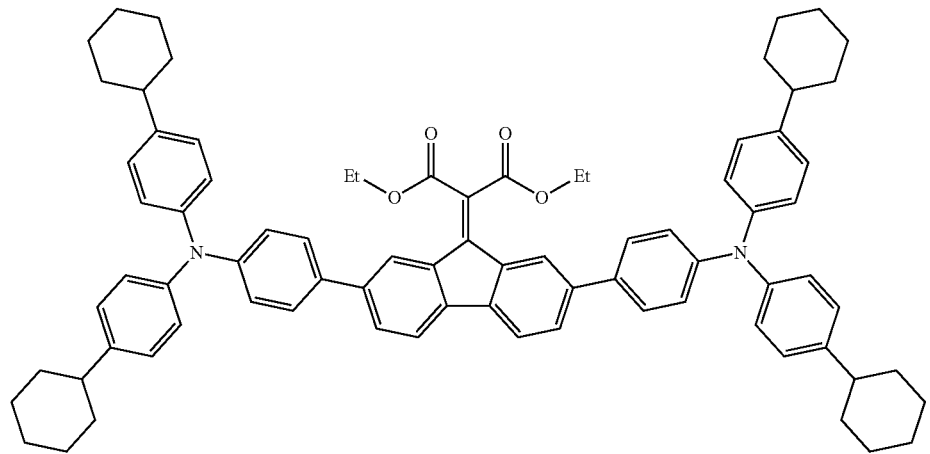
[Chem. 5]
(A-33)
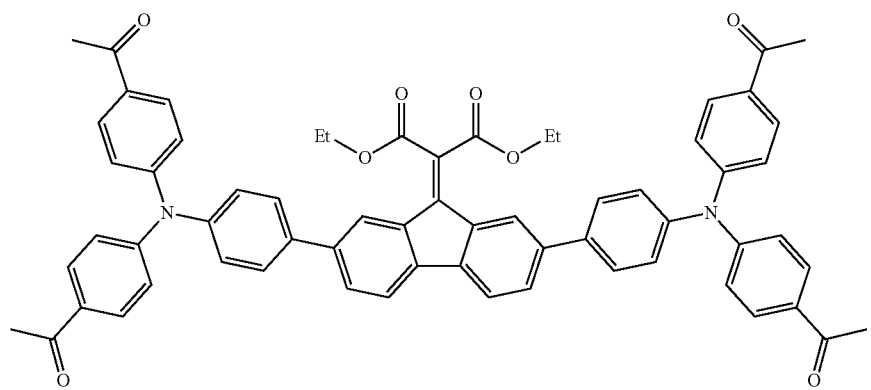

(A-34)
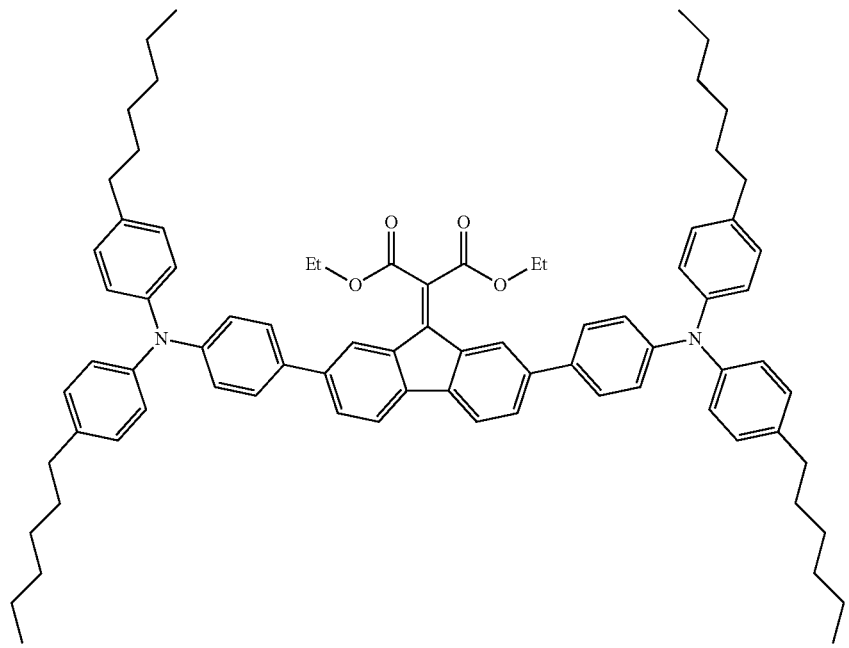
(A-35)
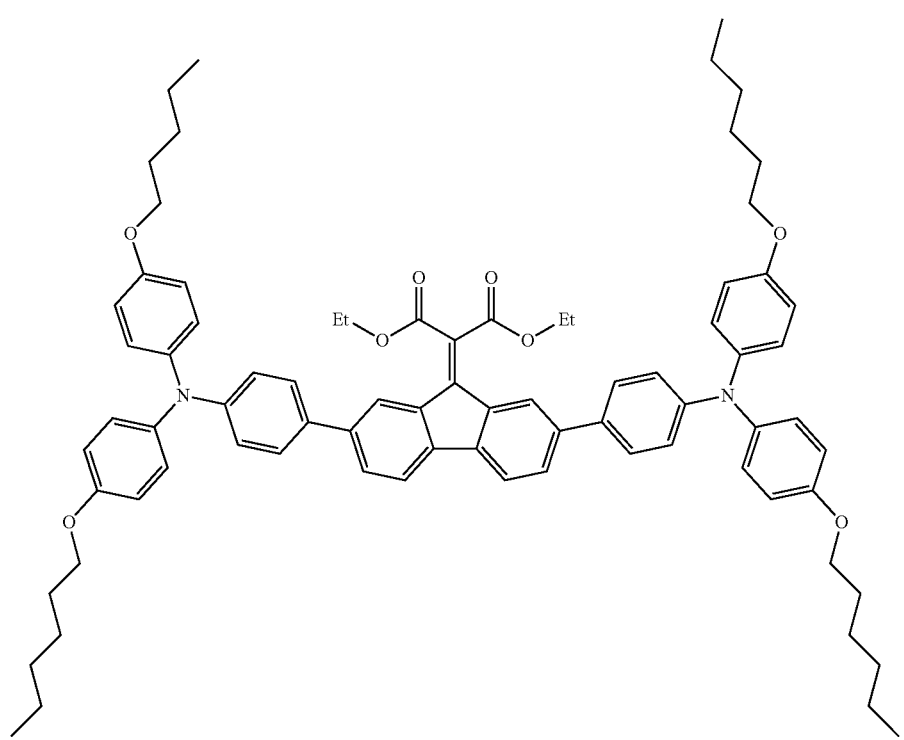

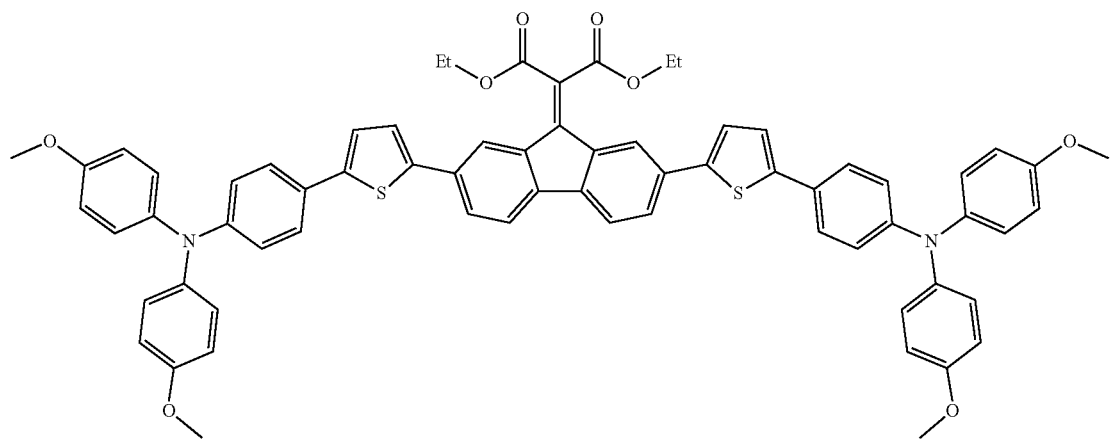
(A-36)
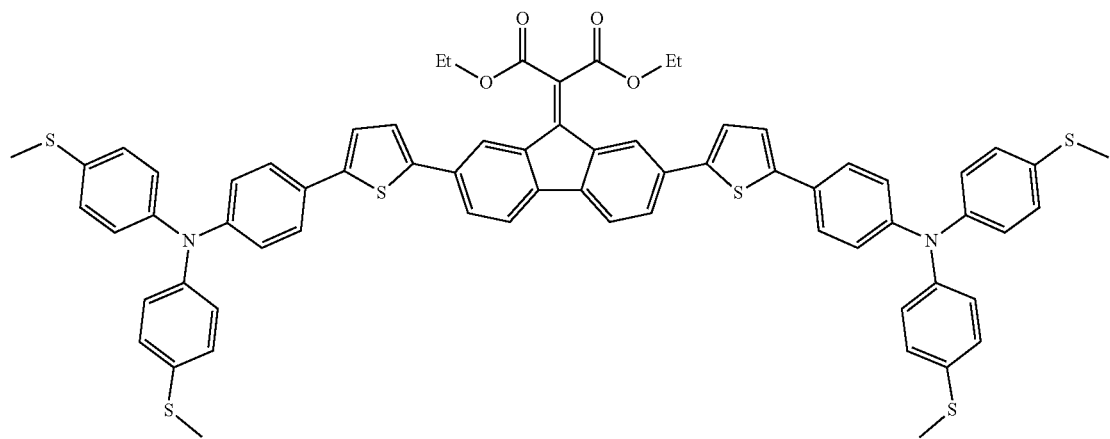
(A-37)
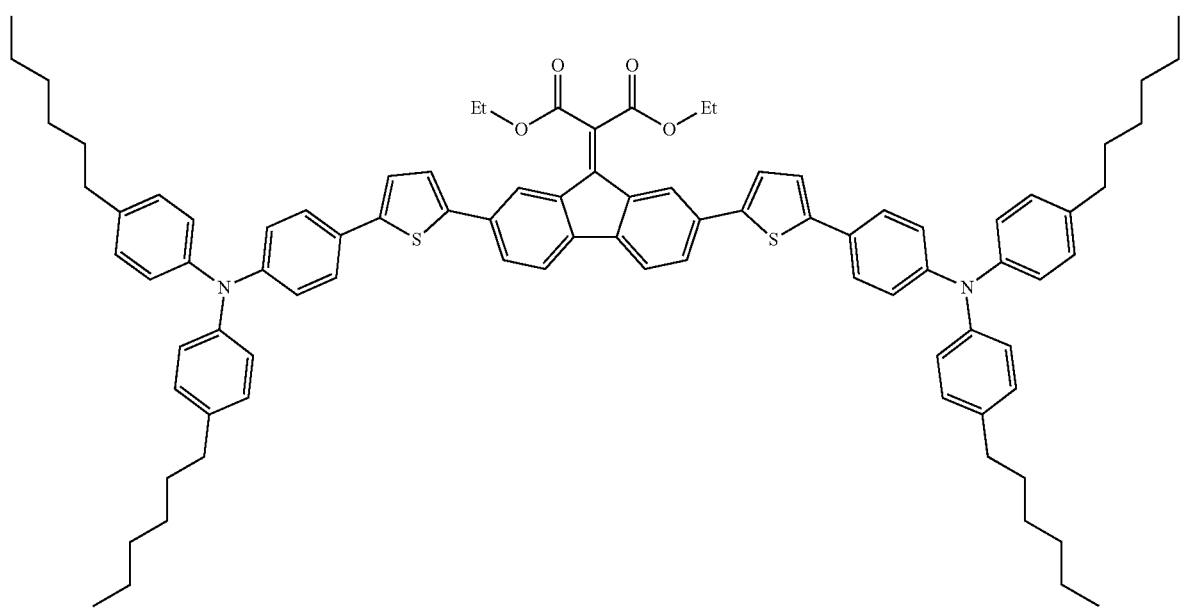
(A-38)

-continued
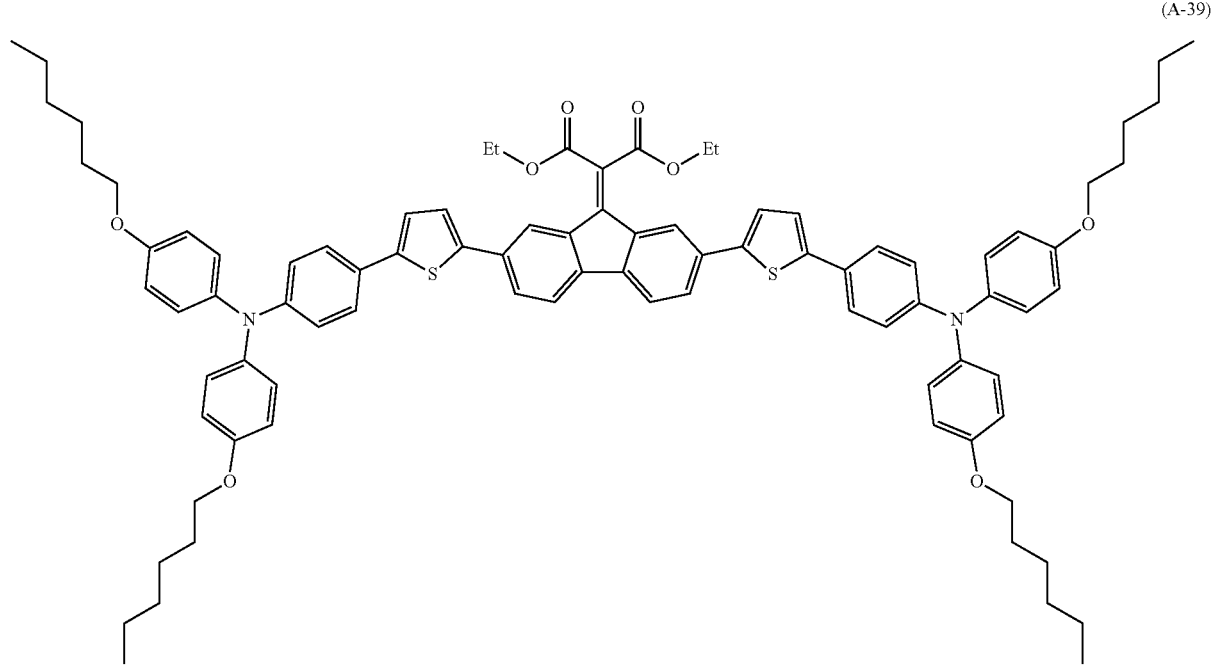 [SMILES: CCCCCCOc1ccc(N(c2ccc(OCCCCCC)cc2)c2ccc(-c3ccc(-c4ccc5c(c4)C(=C(C(=O)OCC)C(=O)OCC)c4cc(-c6ccc(-c7ccc(N(c8ccc(OCCCCCC)cc8)c8ccc(OCCCCCC)cc8)cc7)s6)ccc4-5)s3)cc2)cc1]
(A-39)
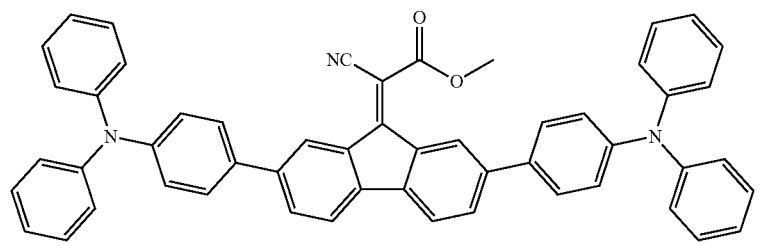
(A-40)
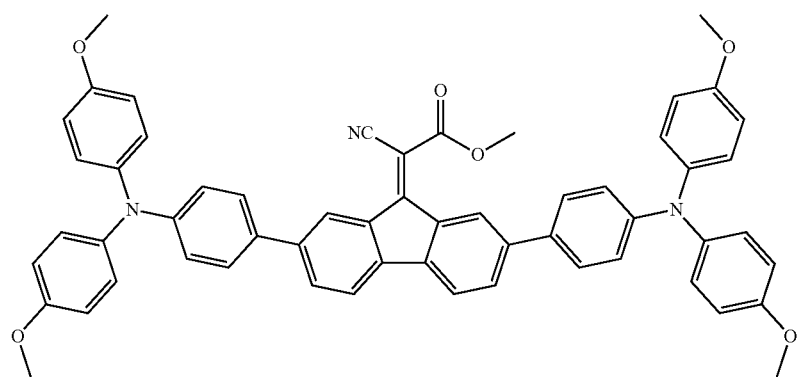
(A-41)
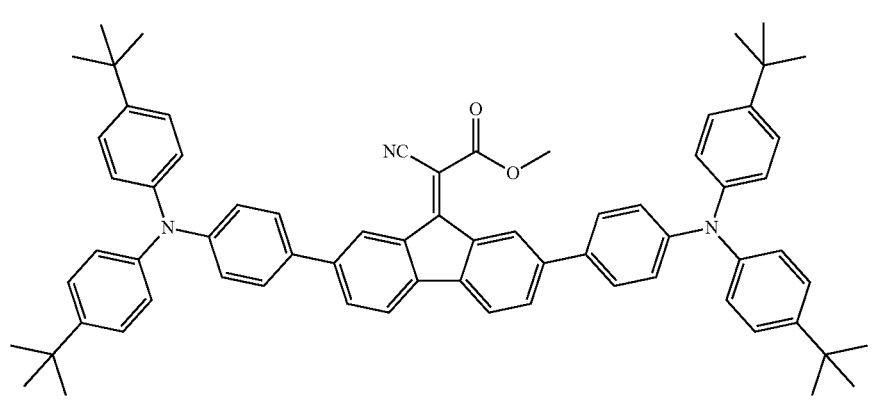
(A-42)

-continued
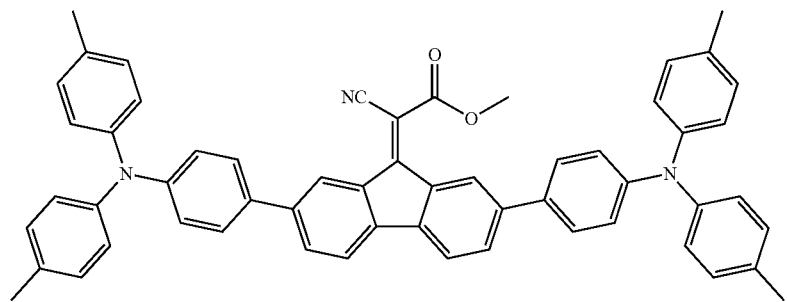
(A-43)
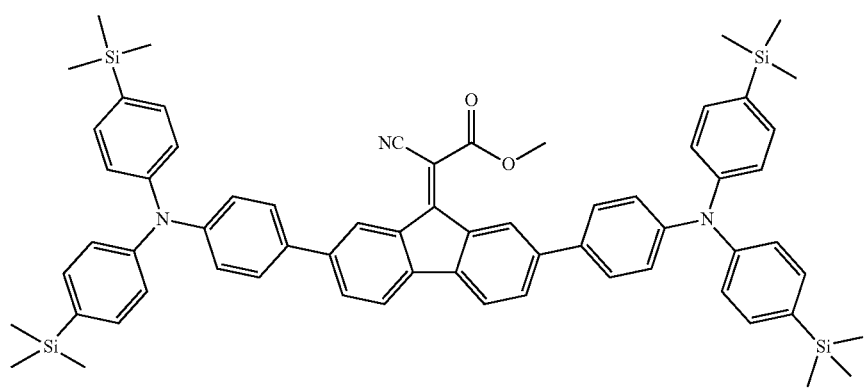
(A-44)
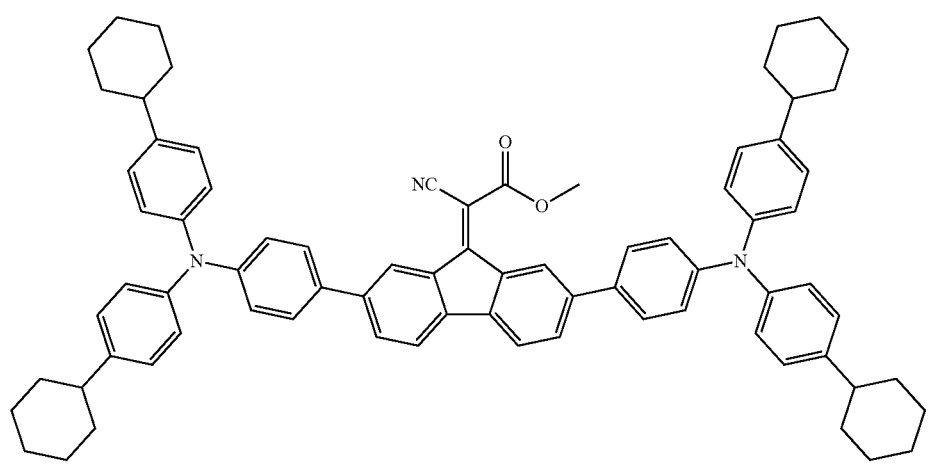
(A-45)

[Chem. 6]
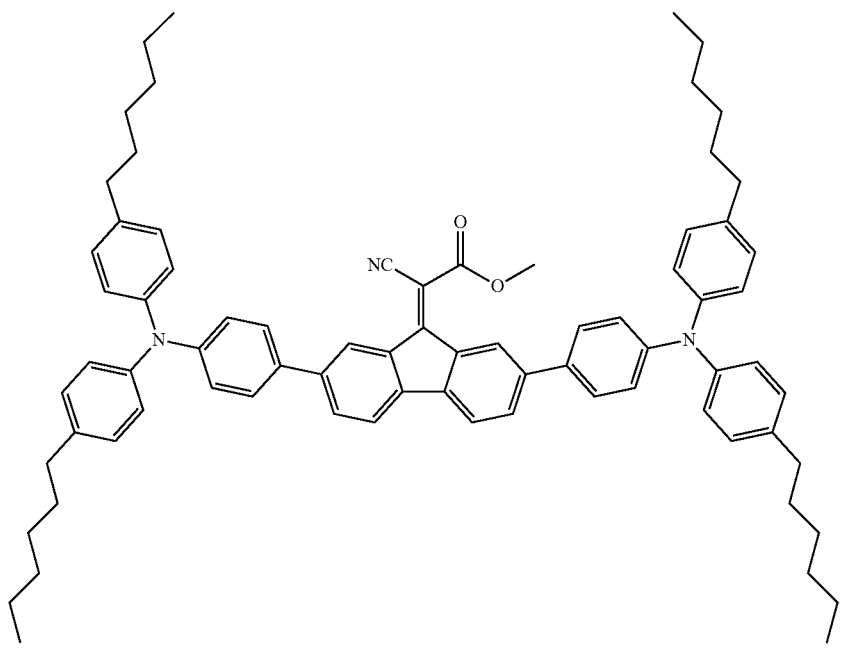
(A-46)
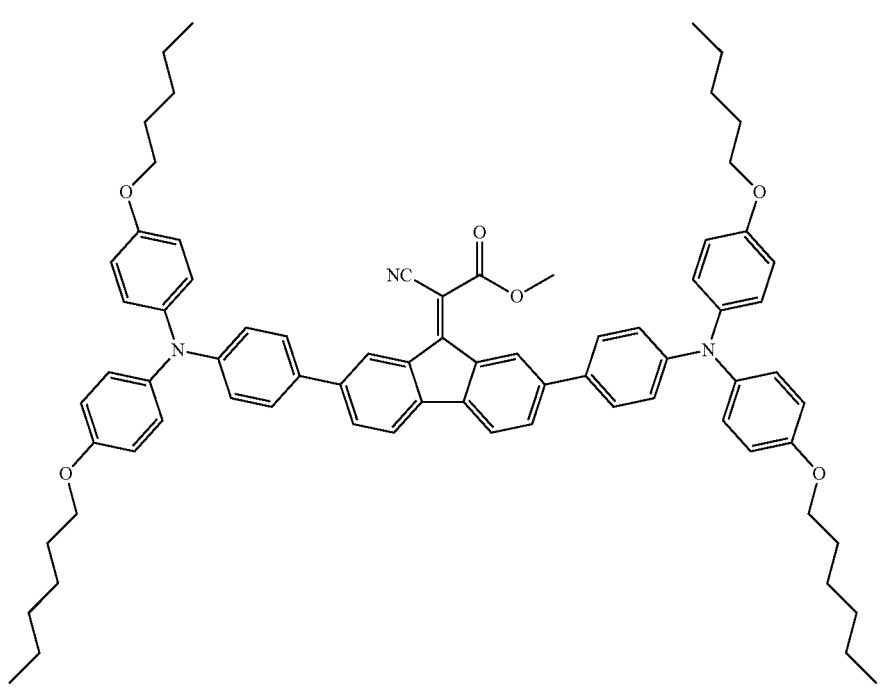
(A-47)

(A-48)
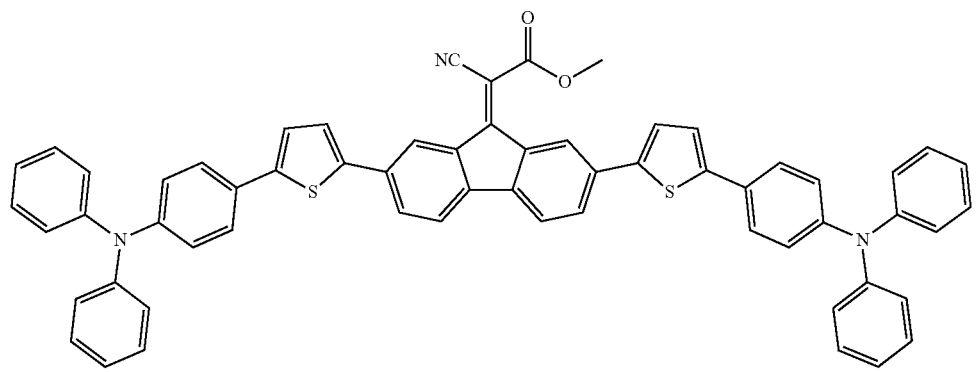
(A-49)
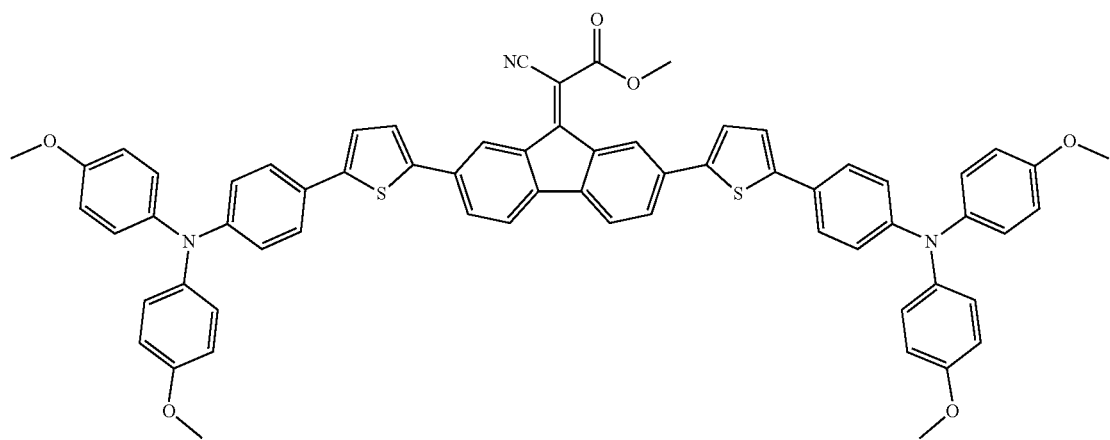
(A-50)
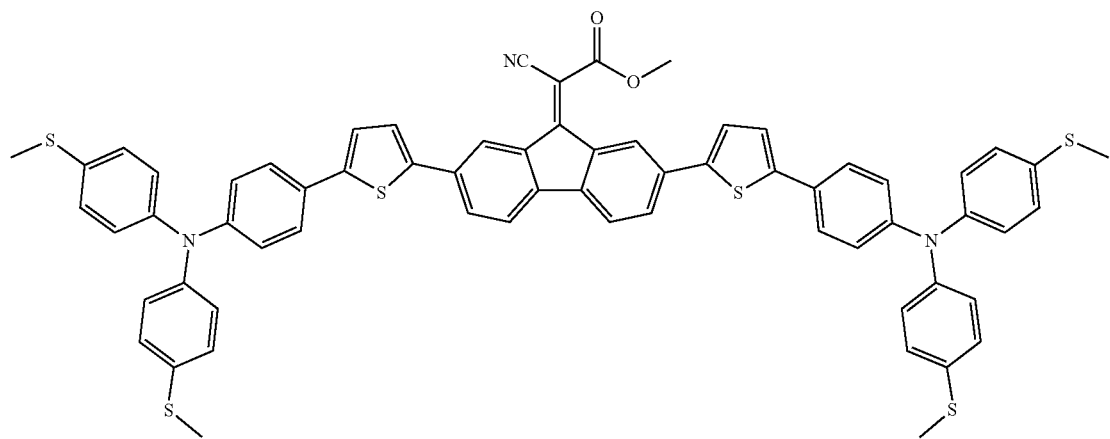

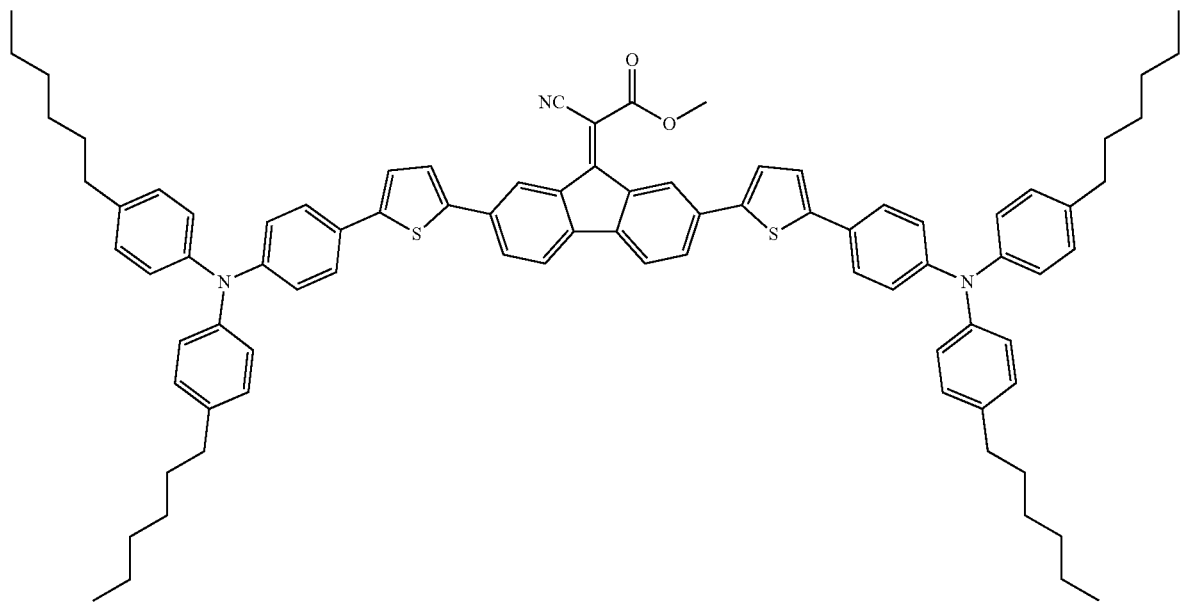
(A-51)
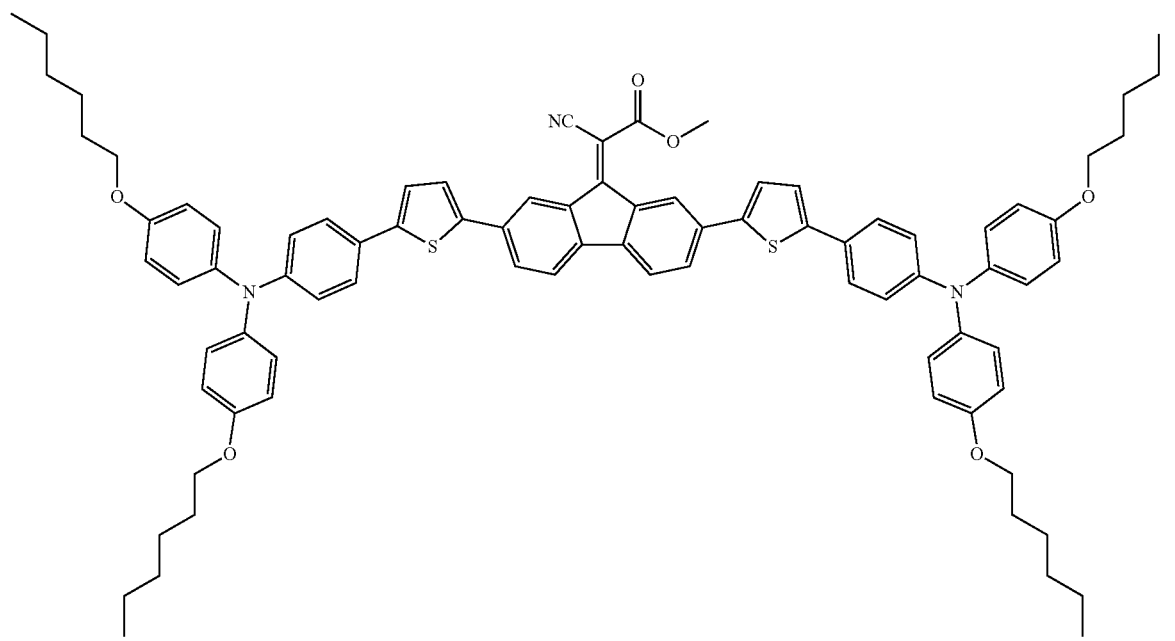
(A-52)
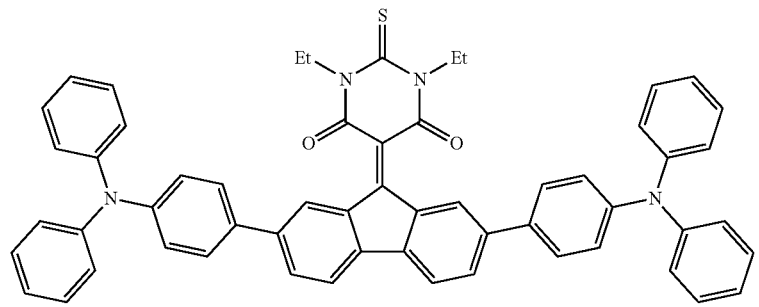
(A-53)

(A-54)
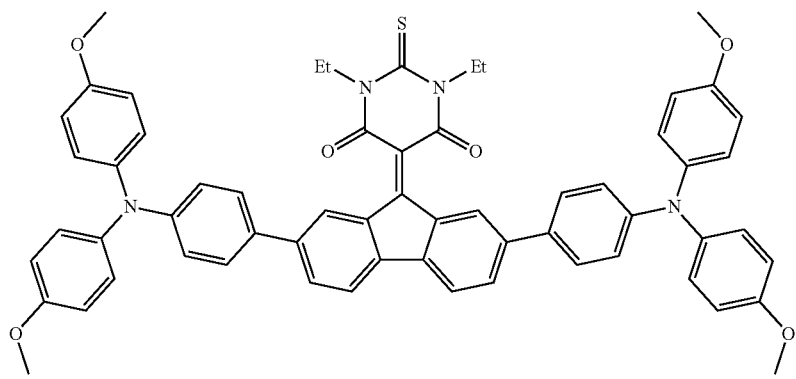
(A-55)
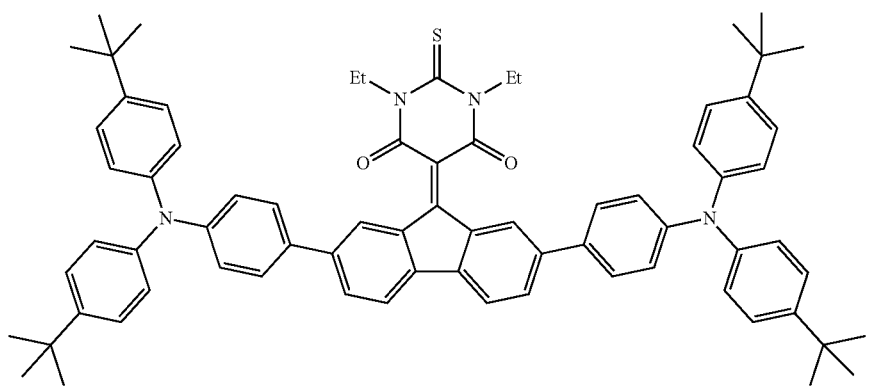
(A-56)
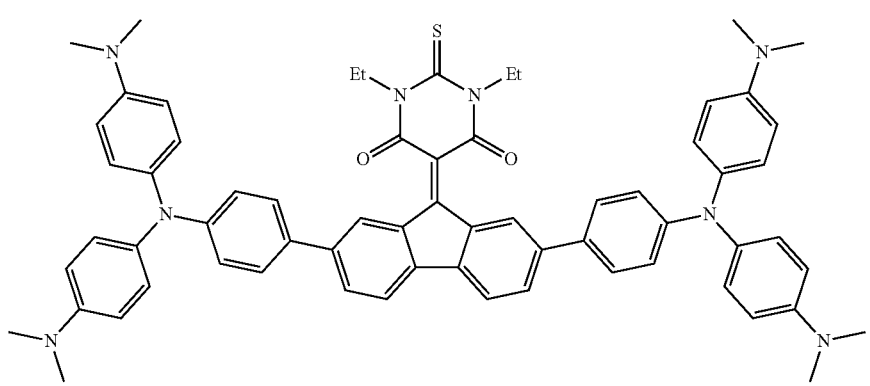
(A-57)
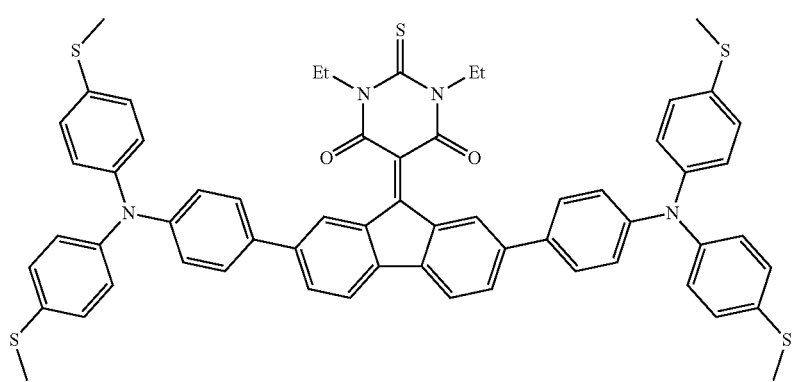

-continued
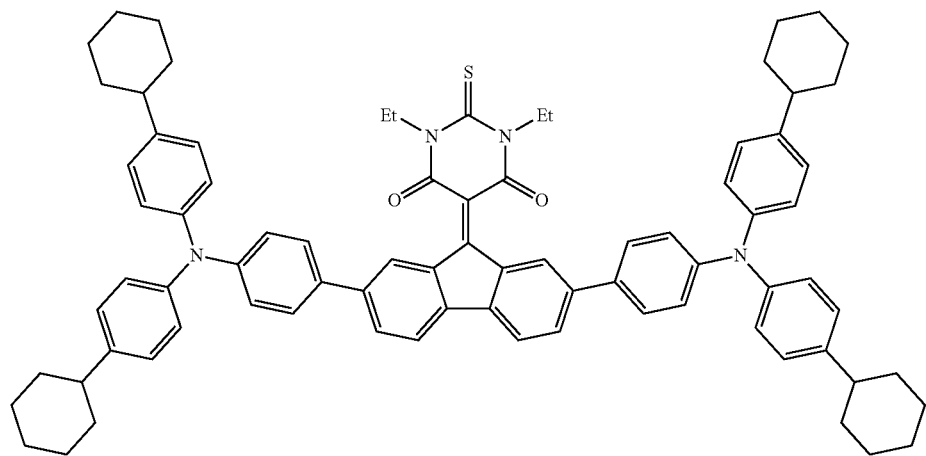
(A-58)
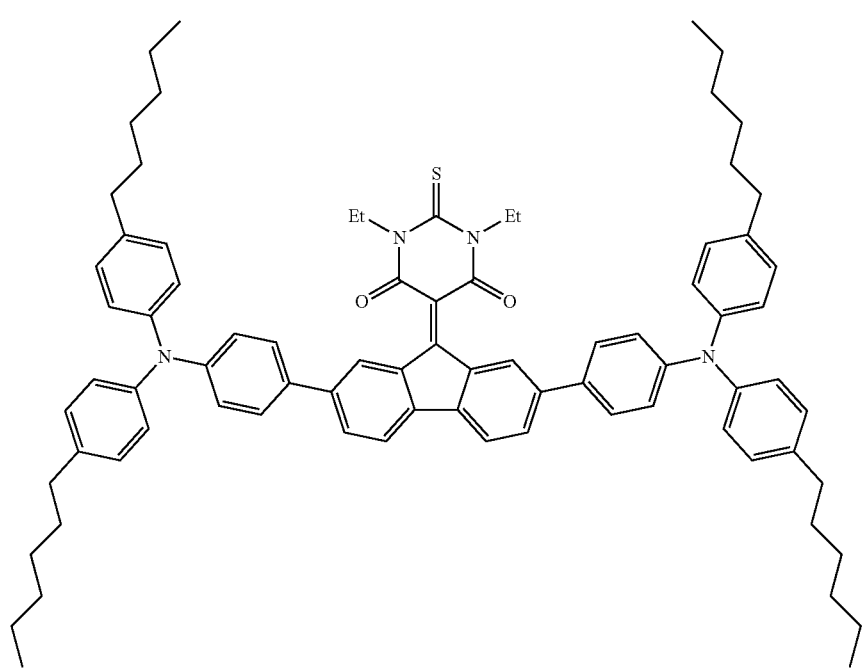
(A-59)

-continued
(A-60)
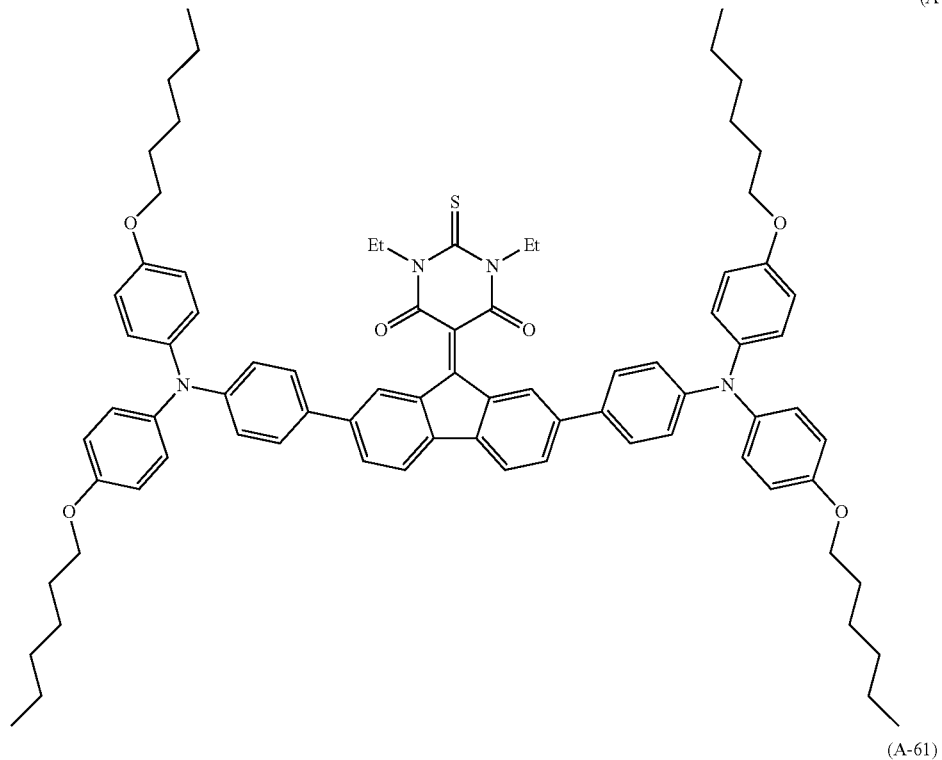
(A-61)
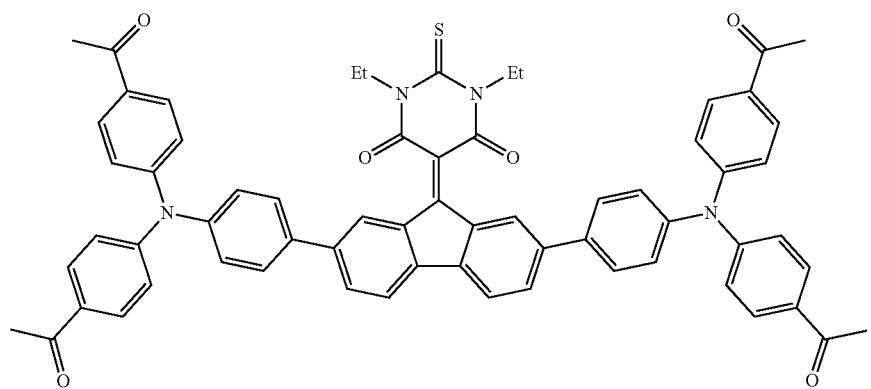
[Chem. 7]
(A-62)
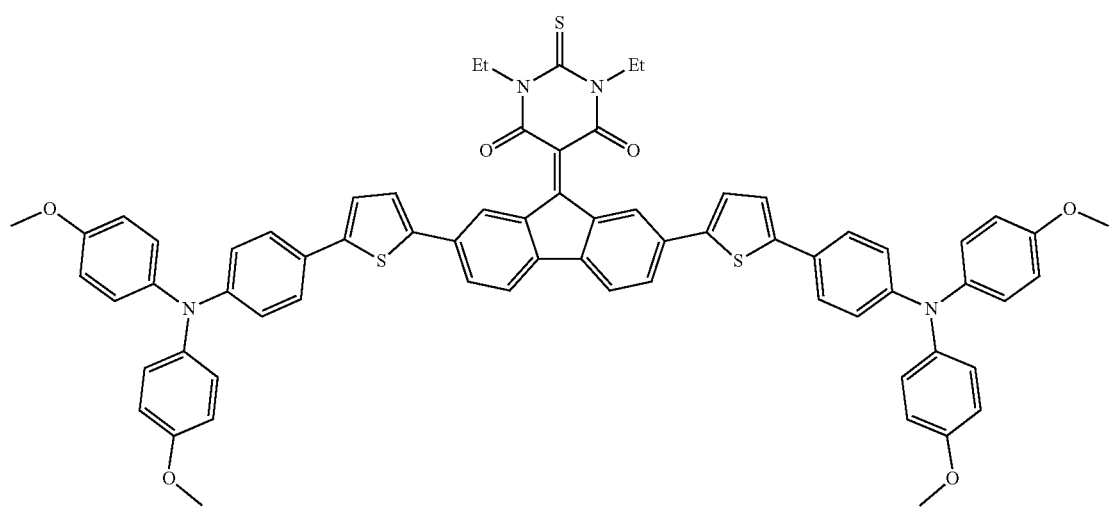

-continued
(A-63)
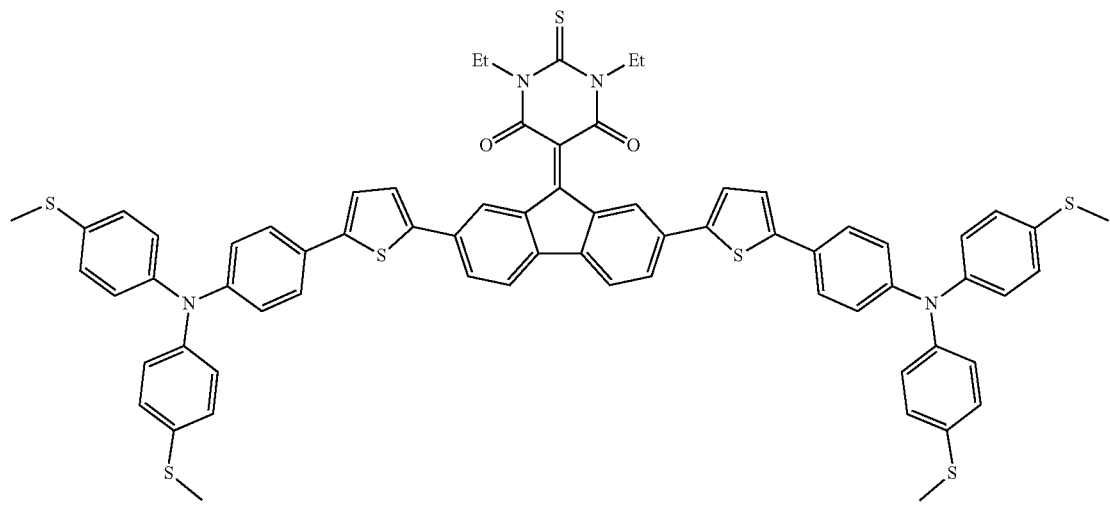
(A-64)
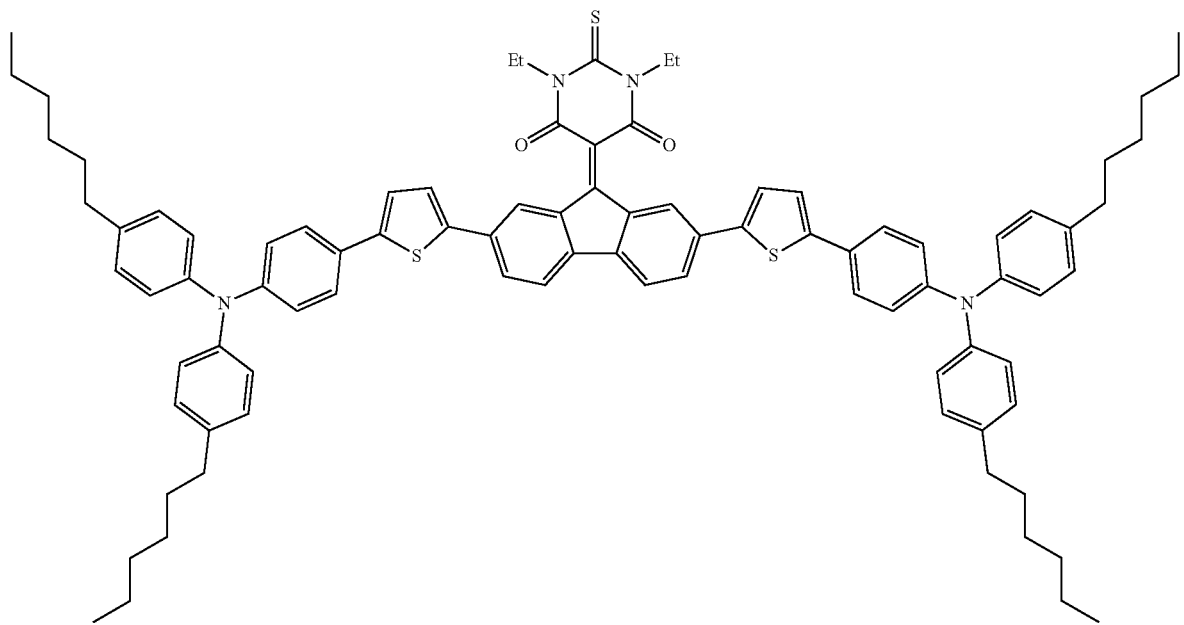

-continued
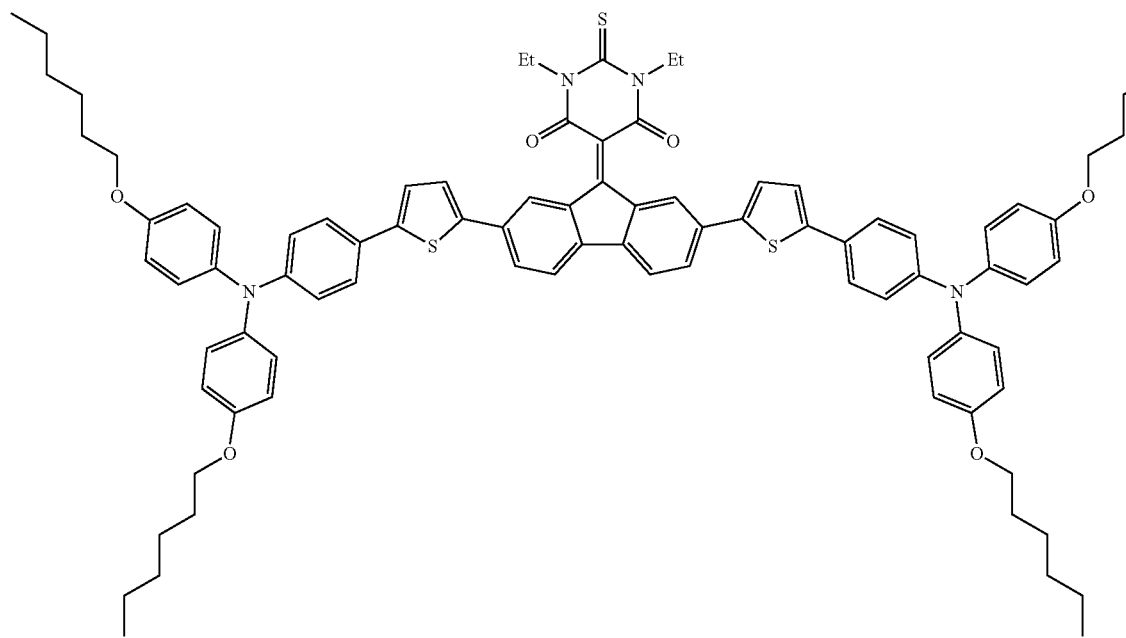
(A-65)
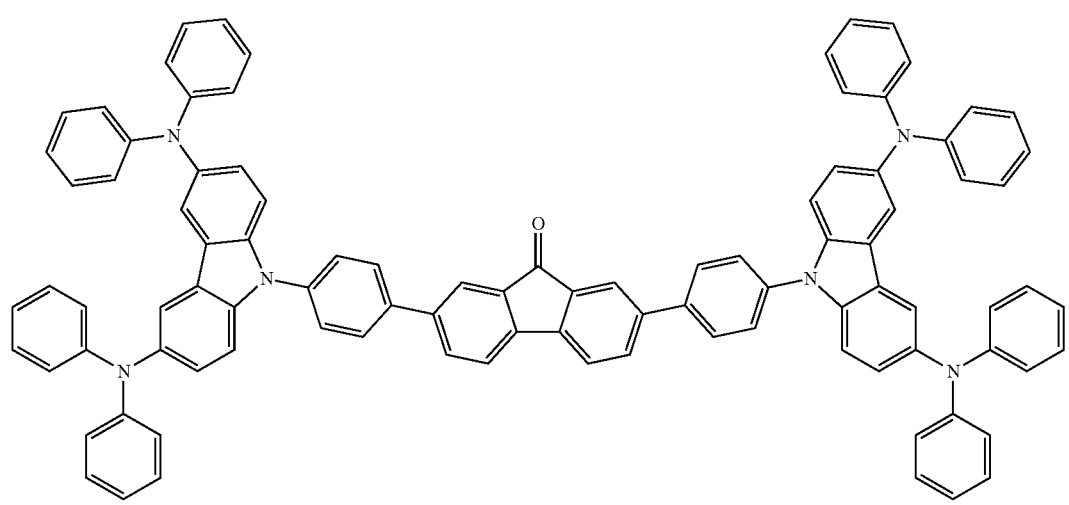
(A-66)

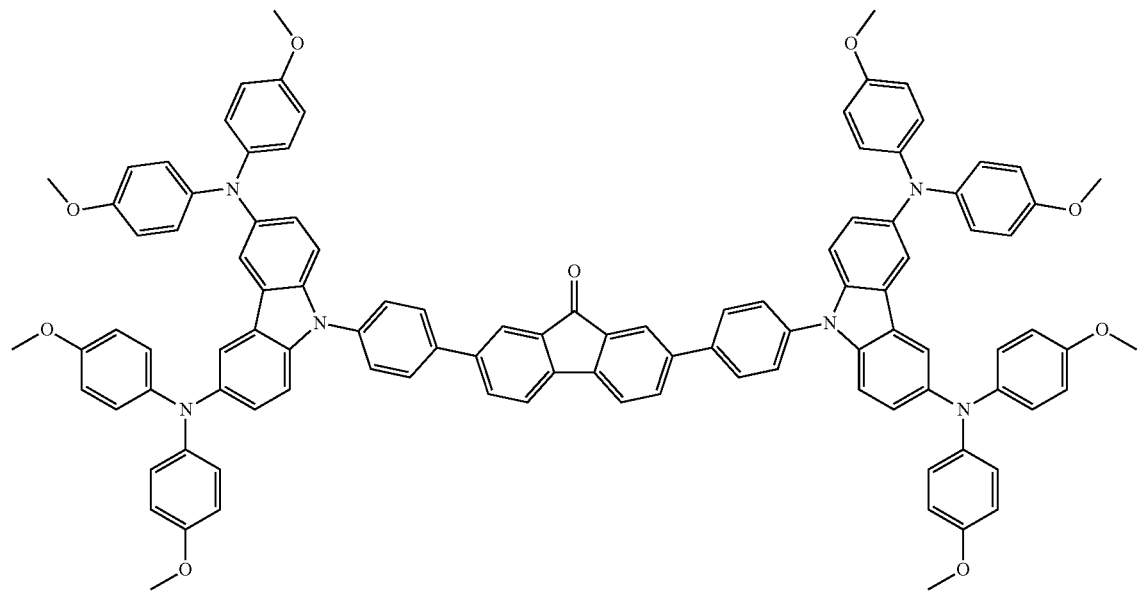
(A-67)
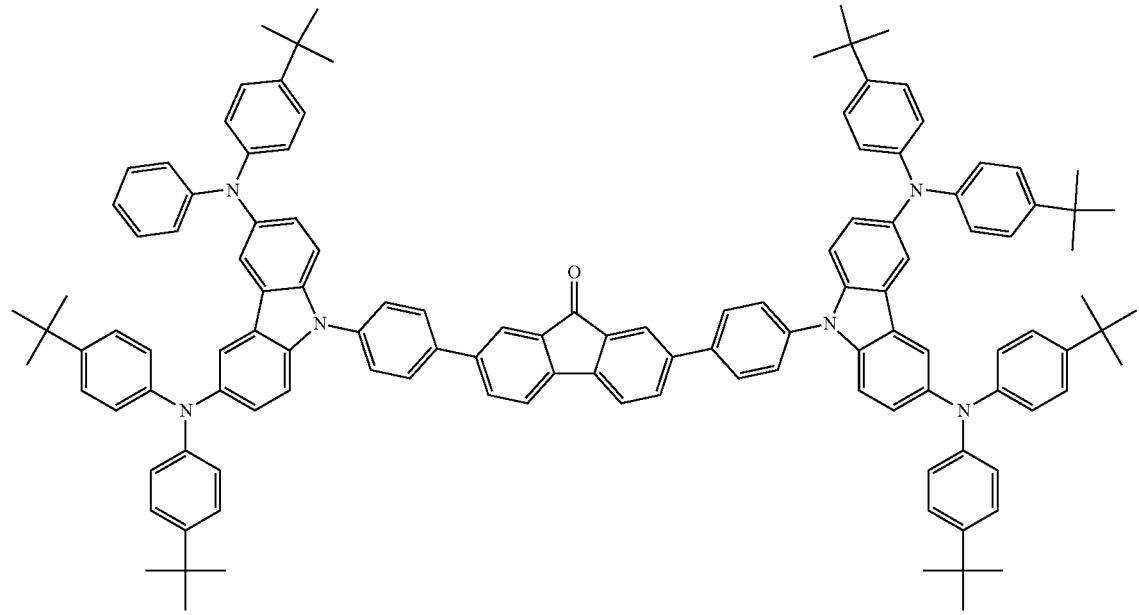
(A-68)

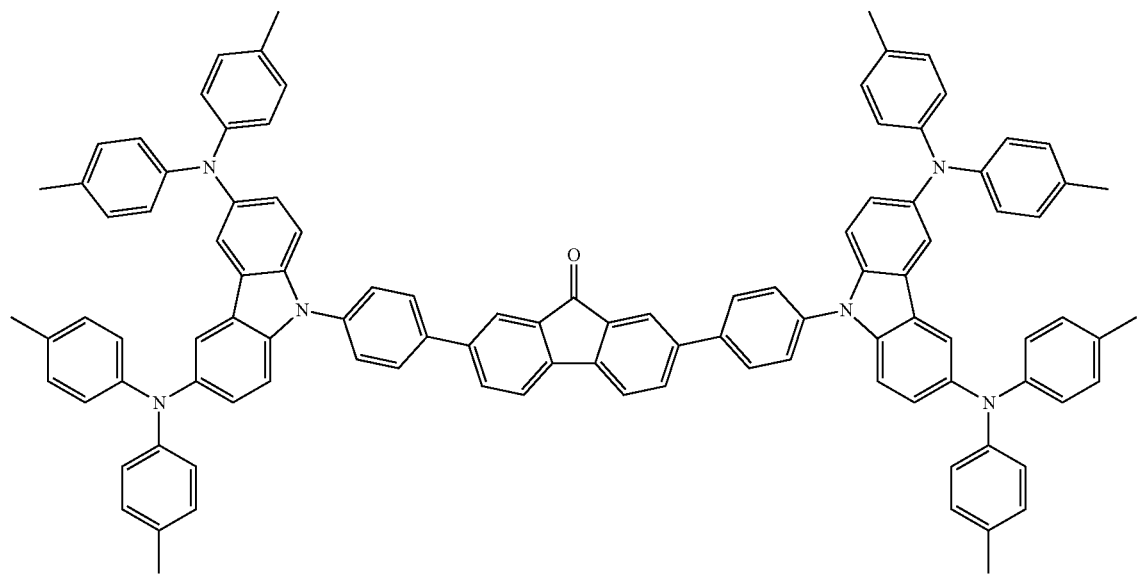
(A-69)
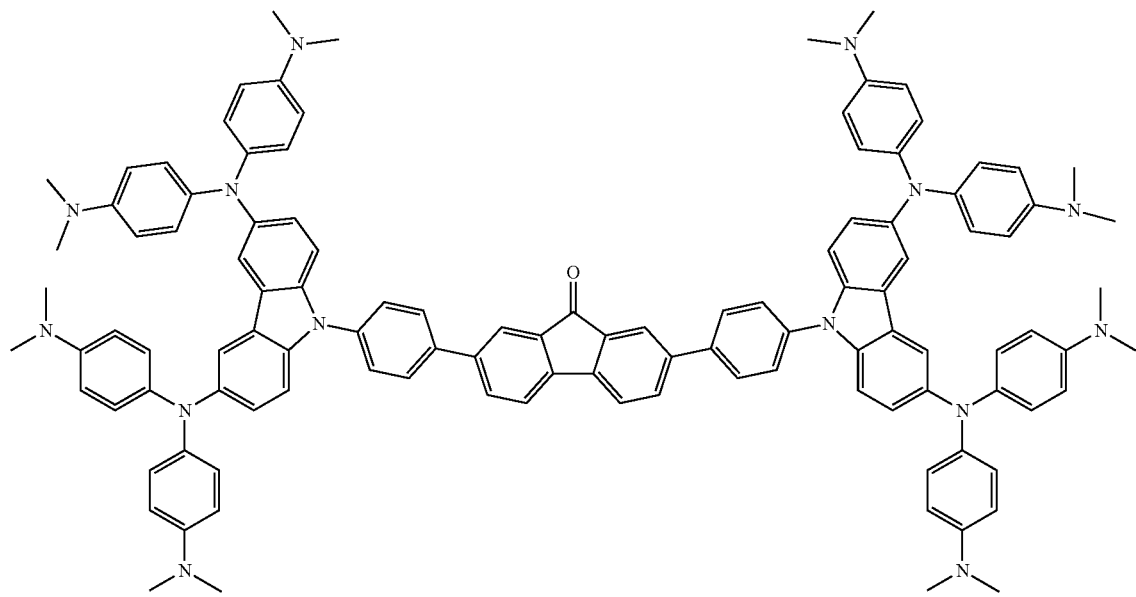
(A-70)

(A-71)
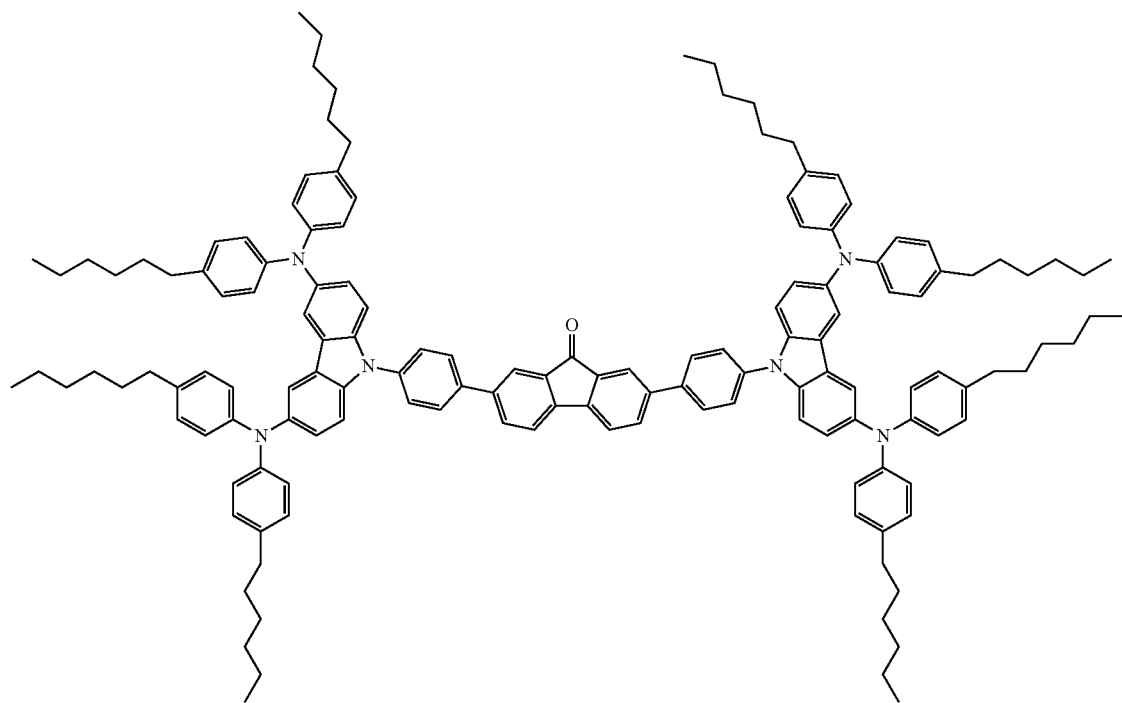
[Chem. 8]
(A-72)
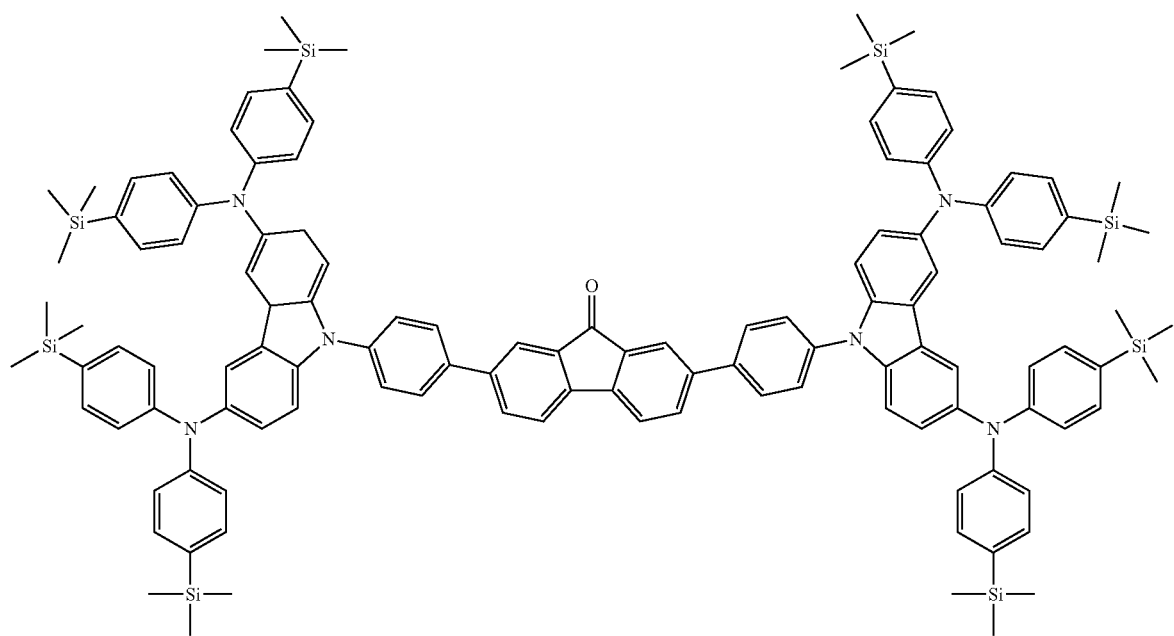

-continued
(A-73)
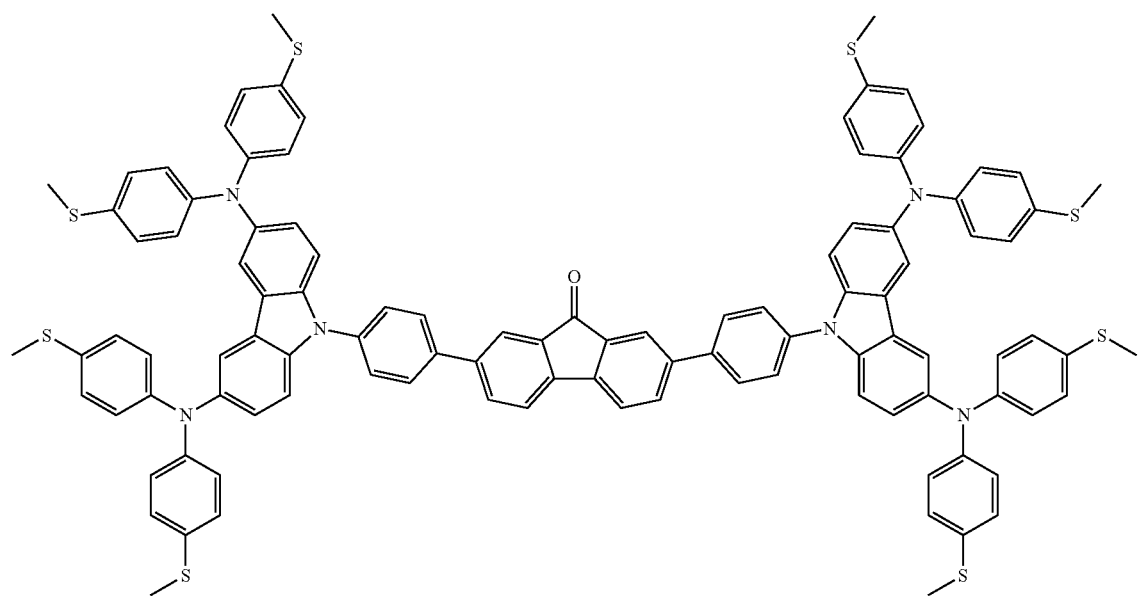
(A-74)
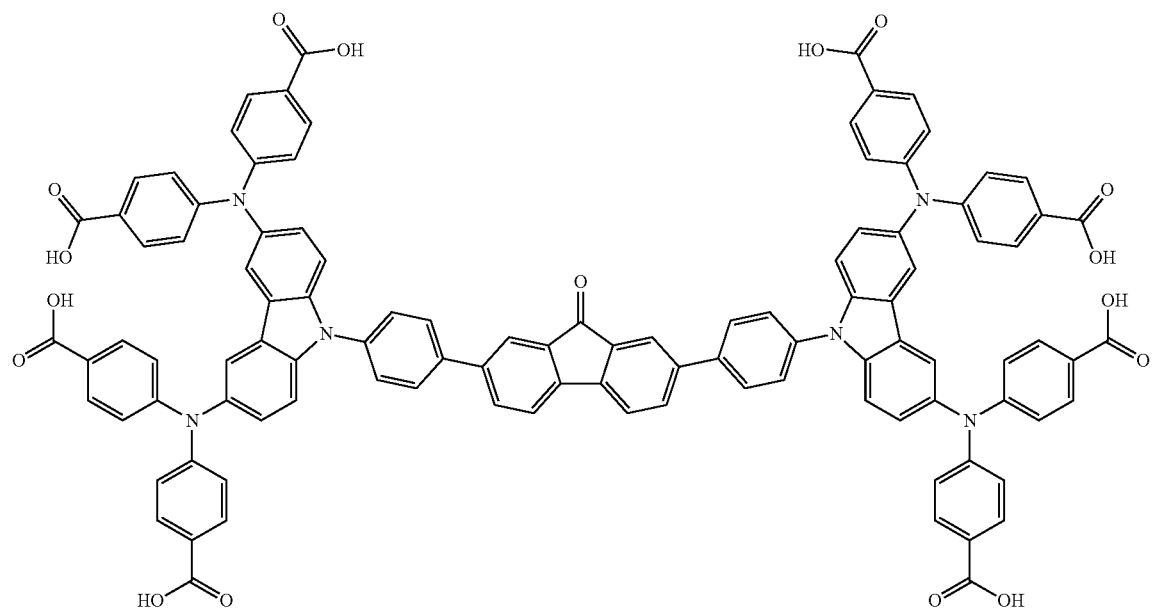

(A-75)
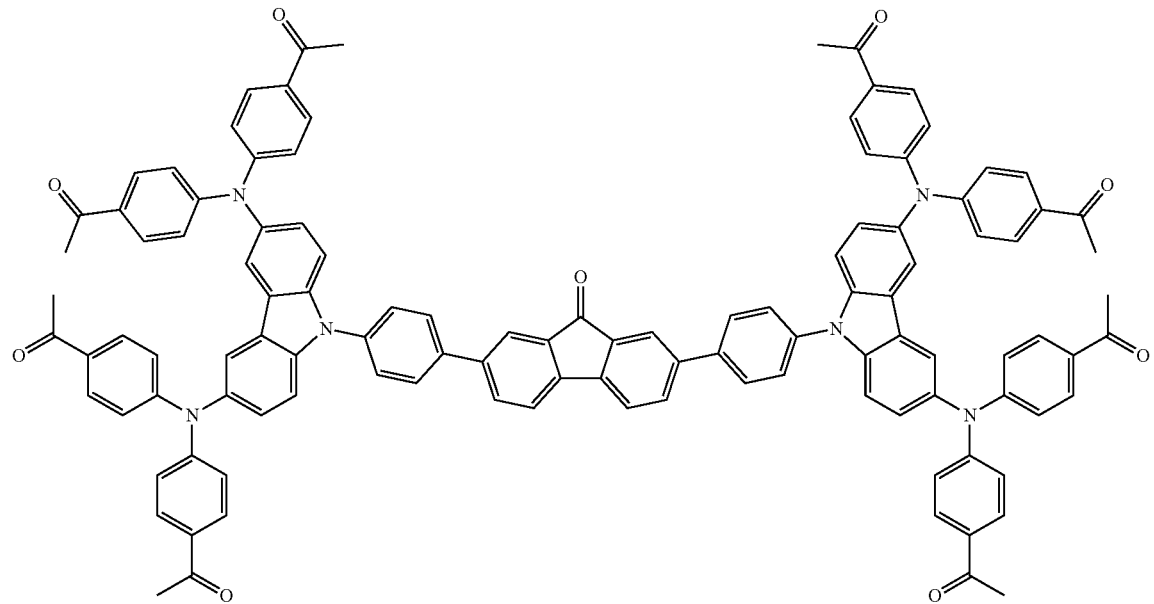
(A-76)
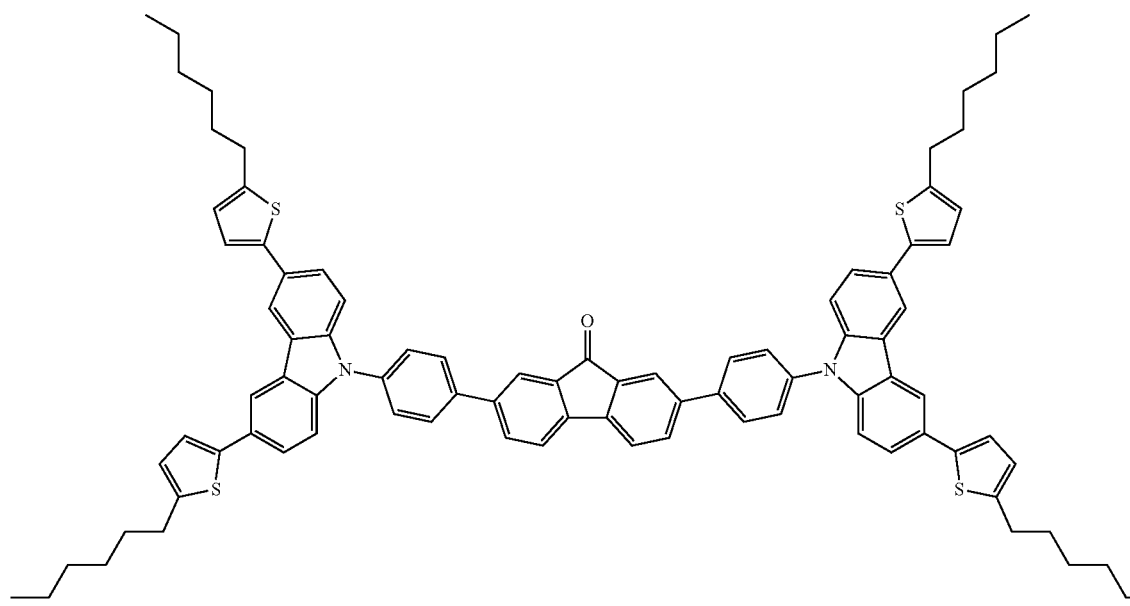
(A-77)
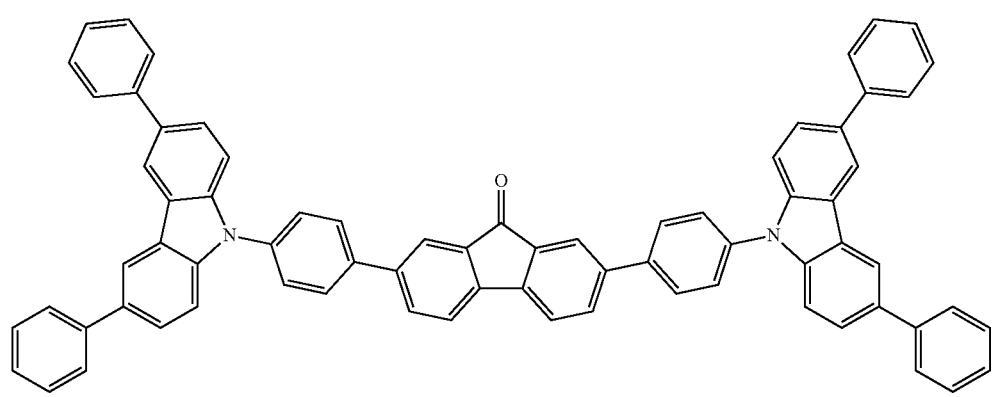

(A-78)
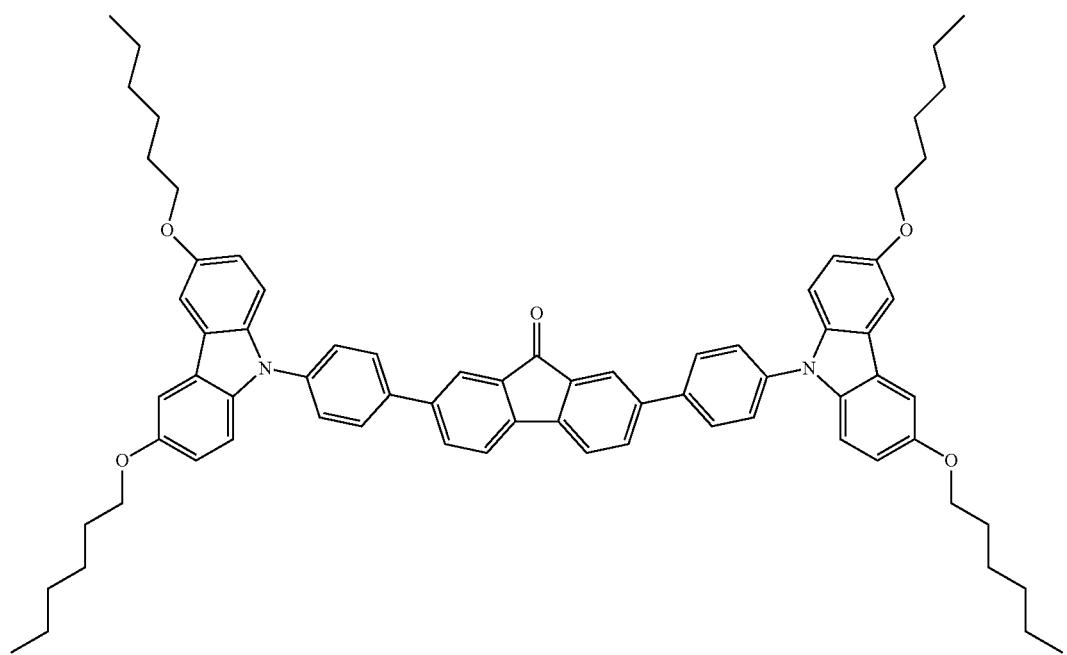
(A-79)
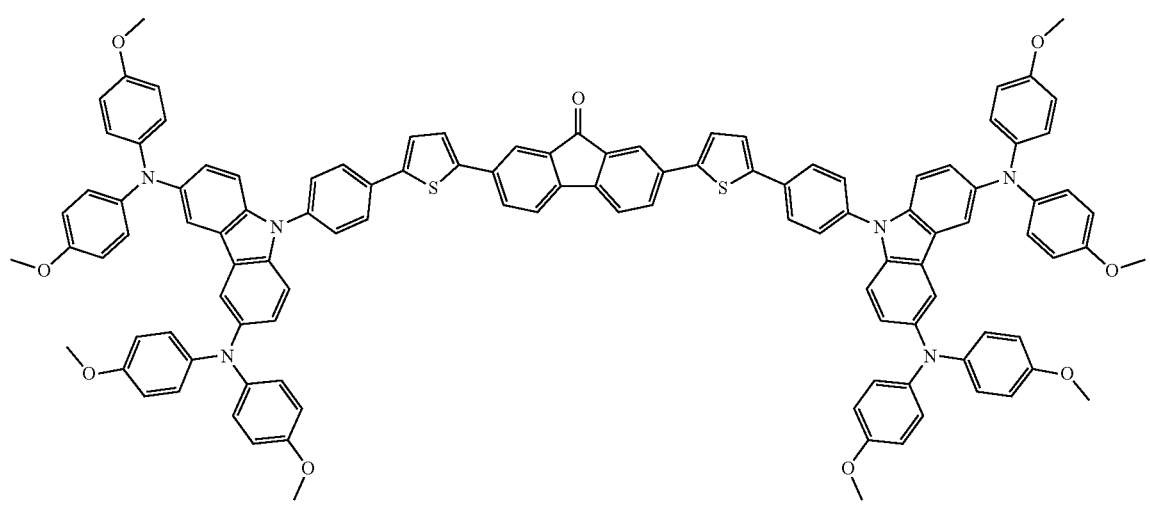
(A-80)
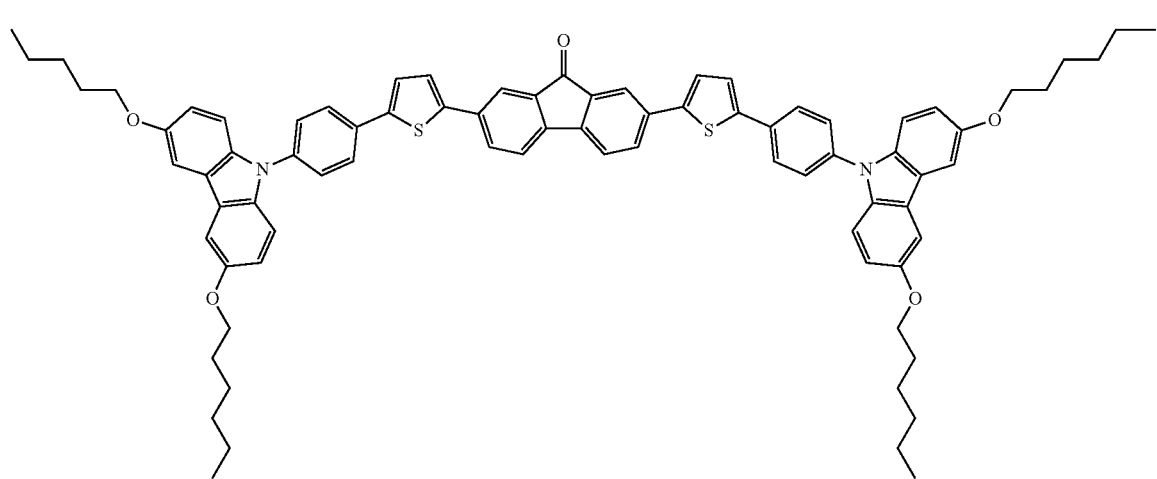

(A-81)
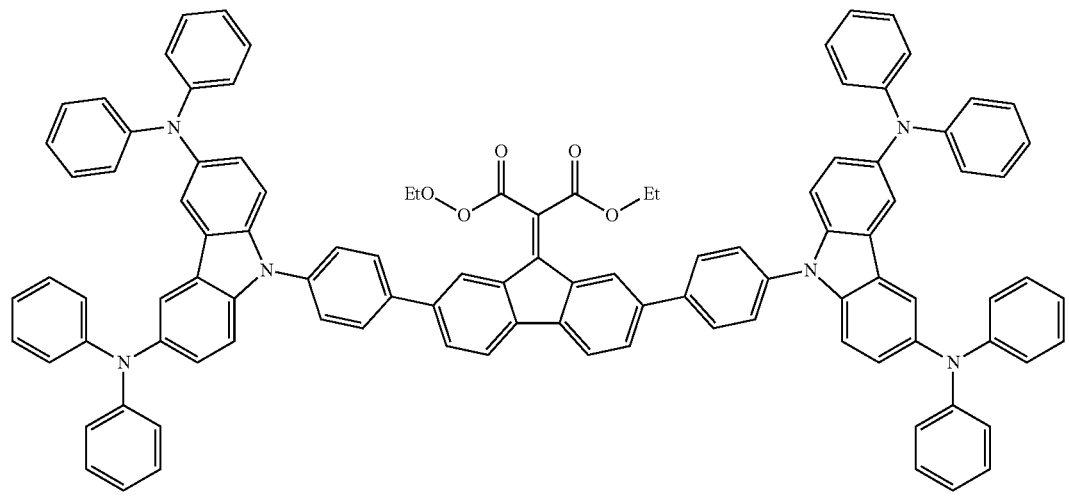
[Chem. 9]
(A-82)
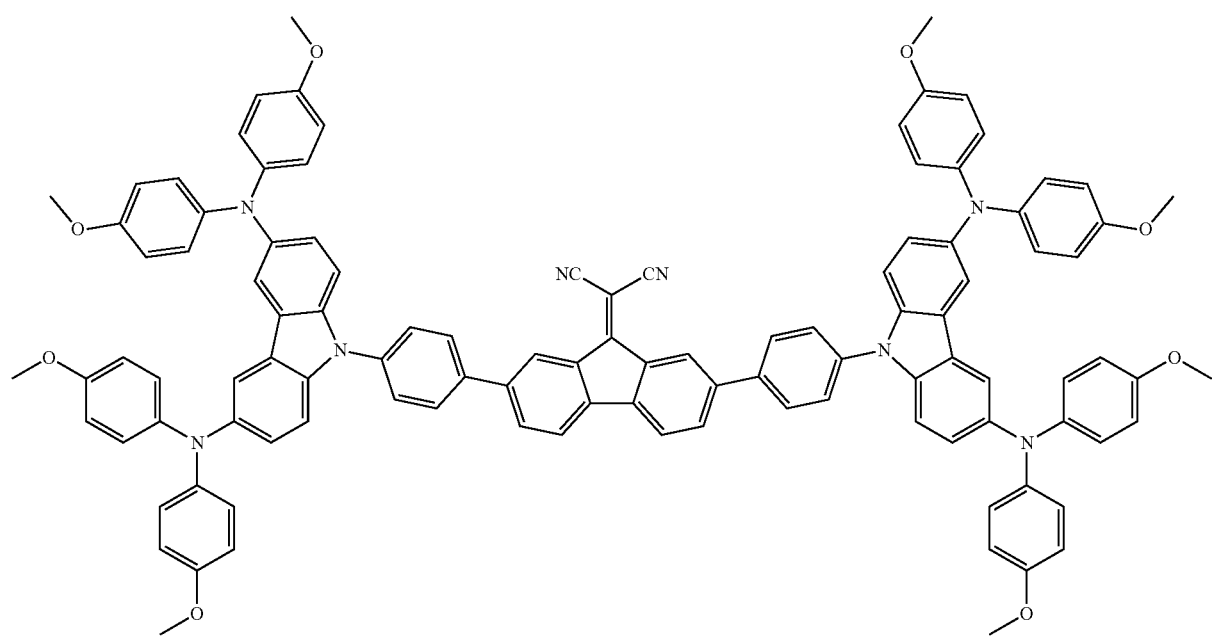

-continued
(A-83)
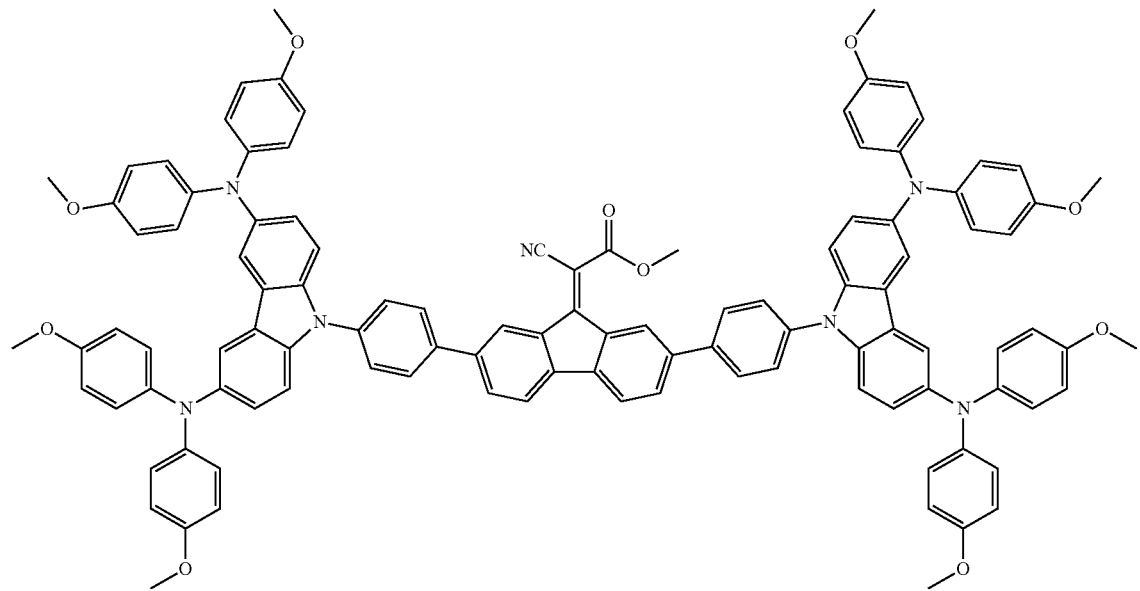
(A-84)
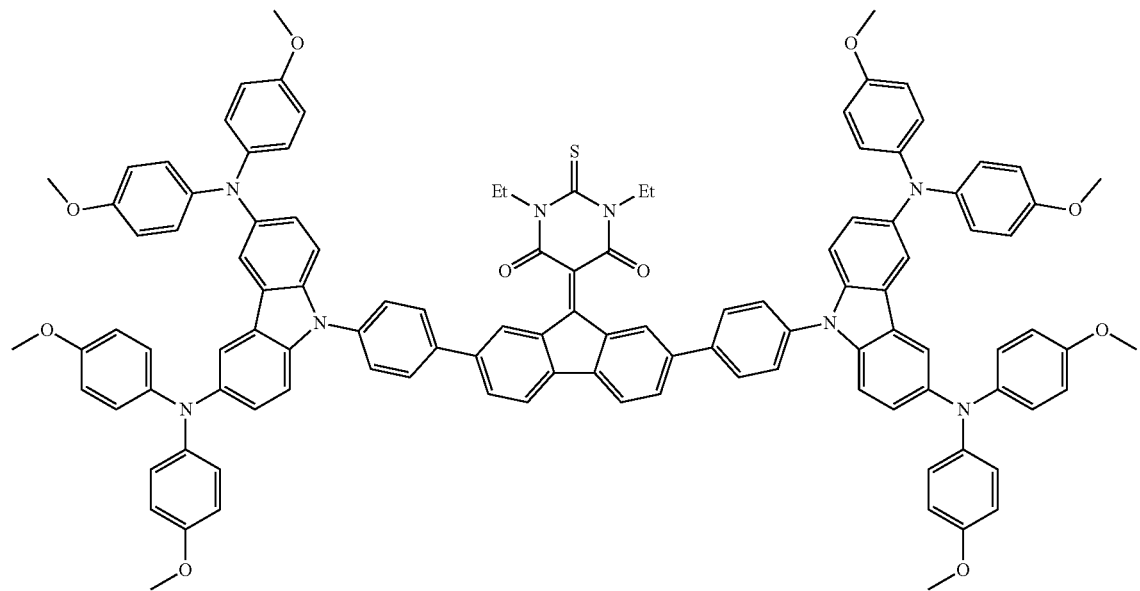

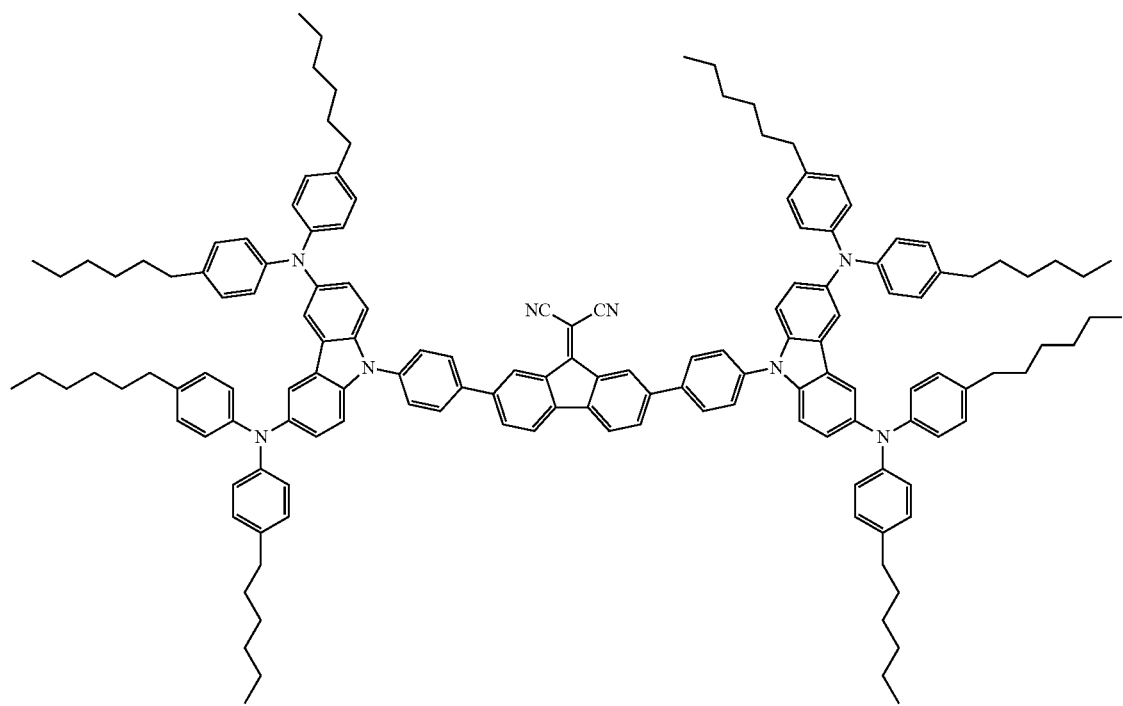
(A-85)
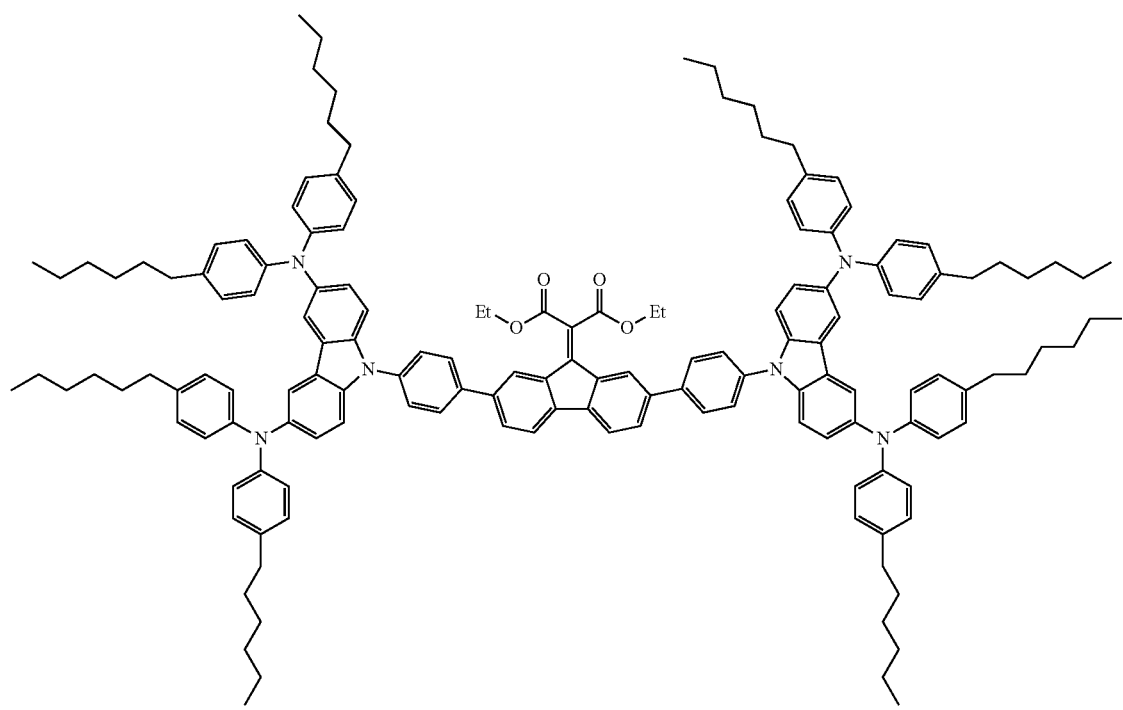
(A-86)

(A-87)
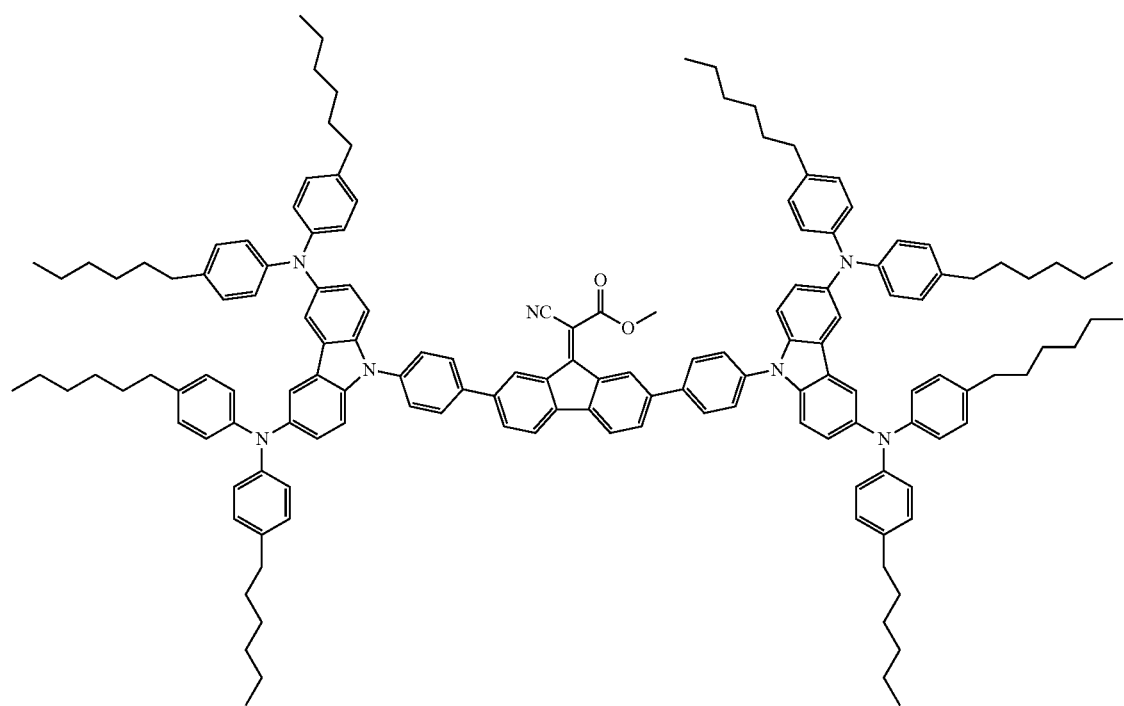
(A-88)
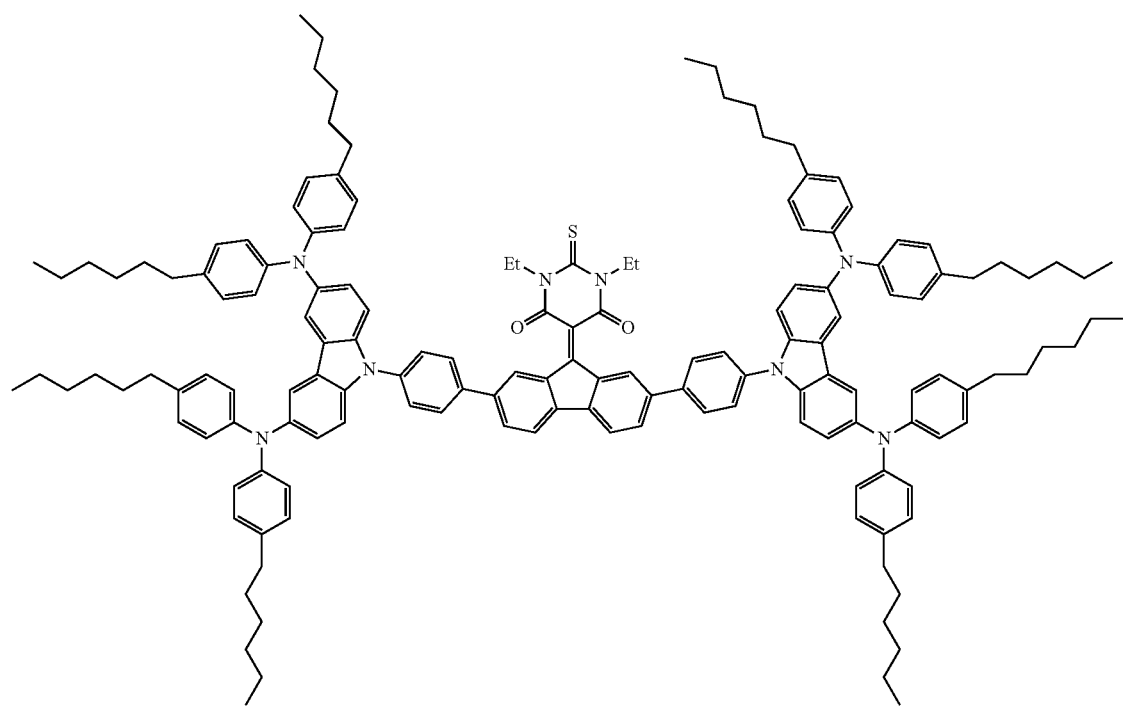

(A-89)
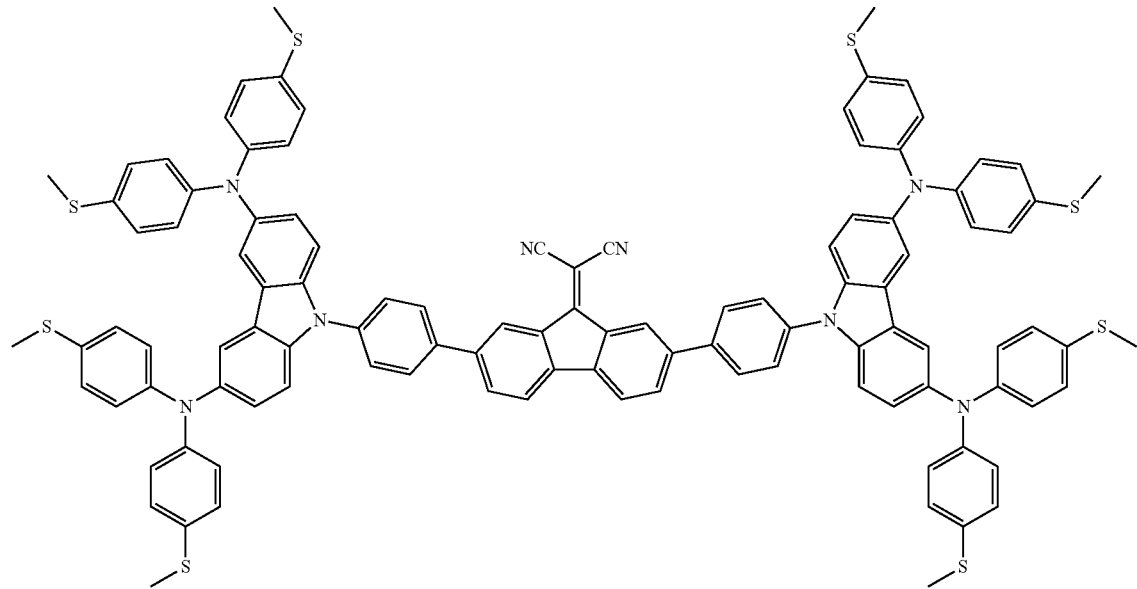
[Chem. 10]
(A-90)
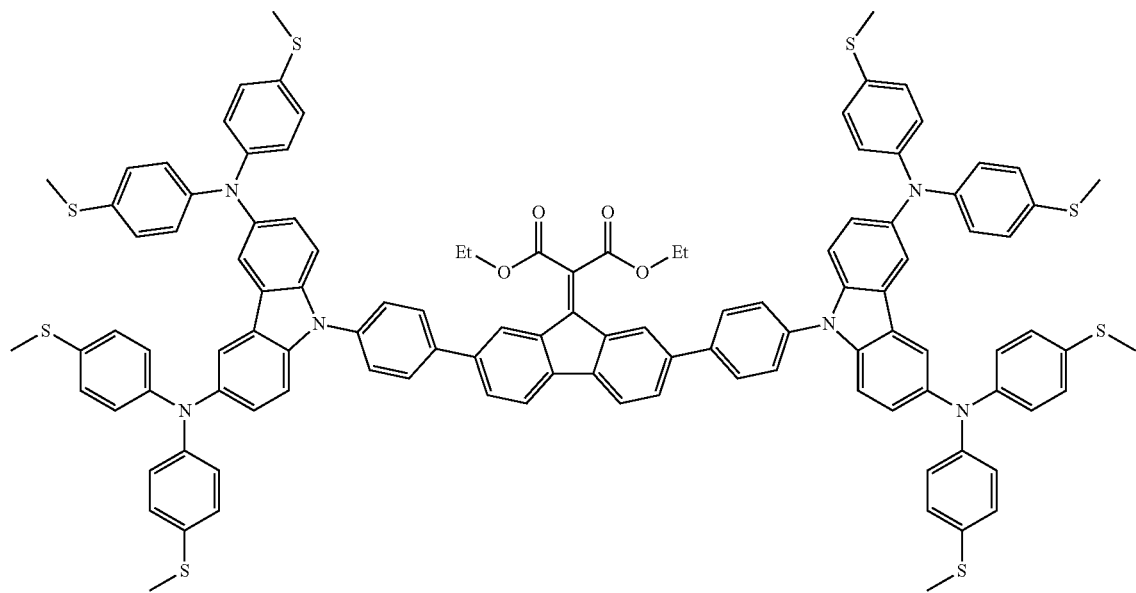

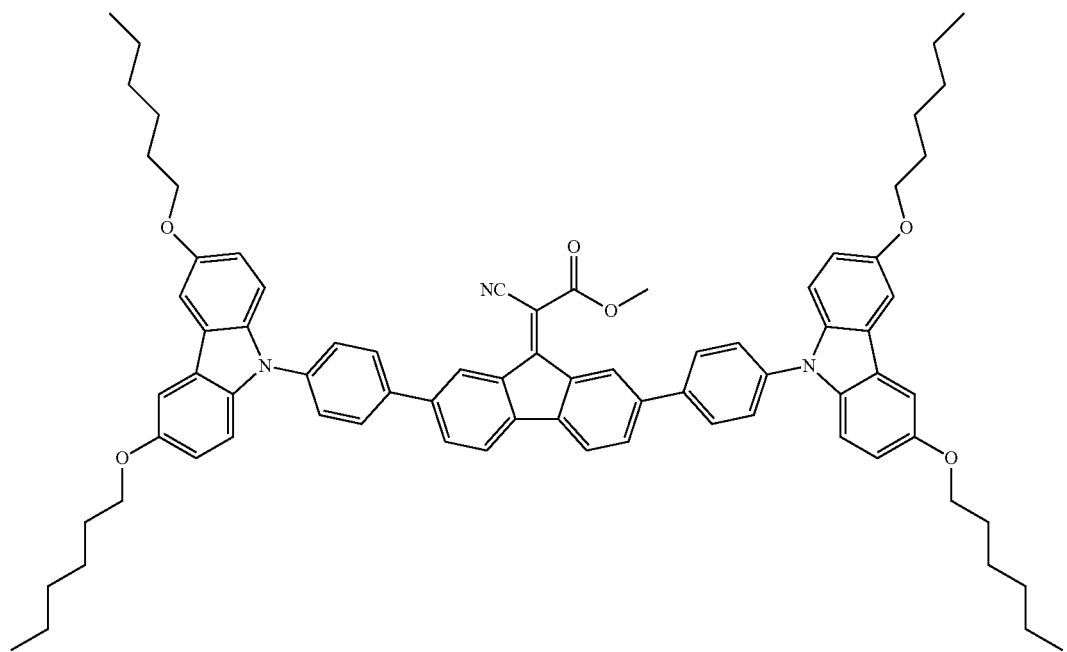
(A-91)
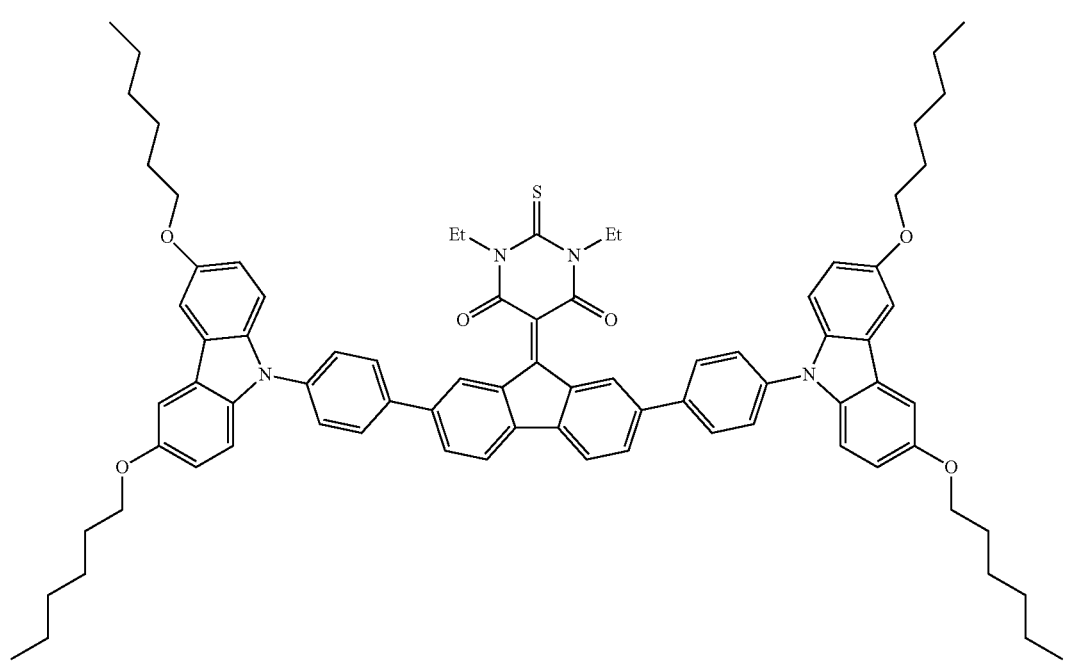
(A-92)

-continued
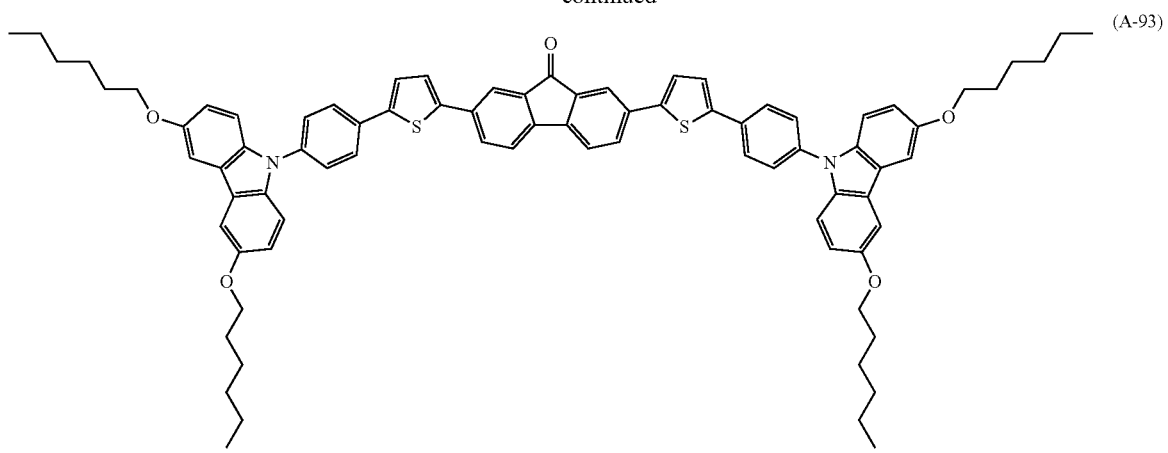
(A-93)
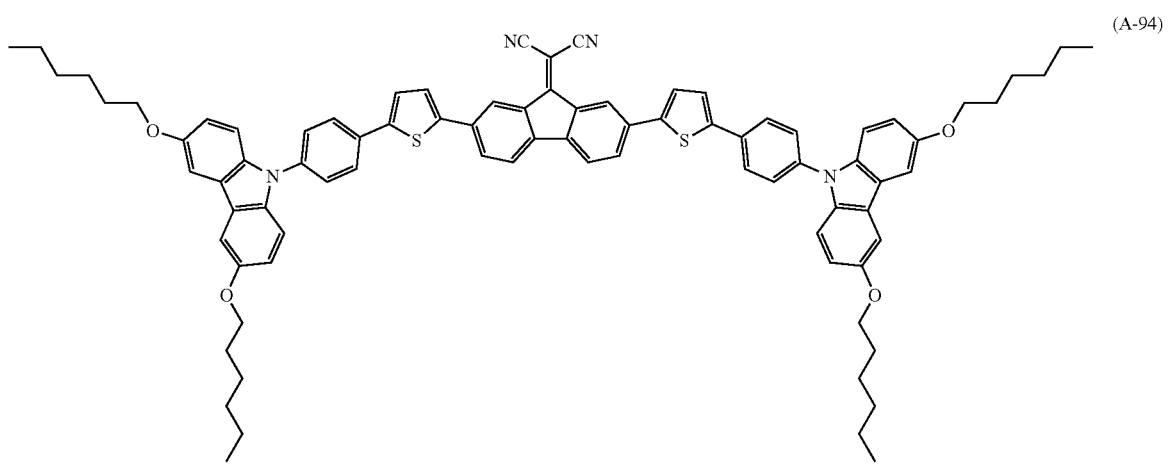
(A-94)
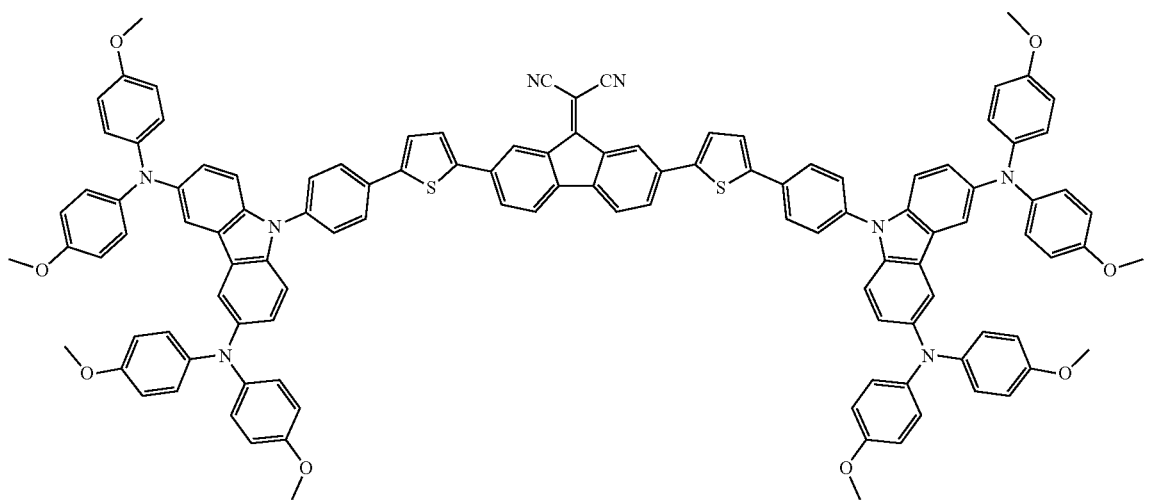
(A-95)

-continued
(A-96)
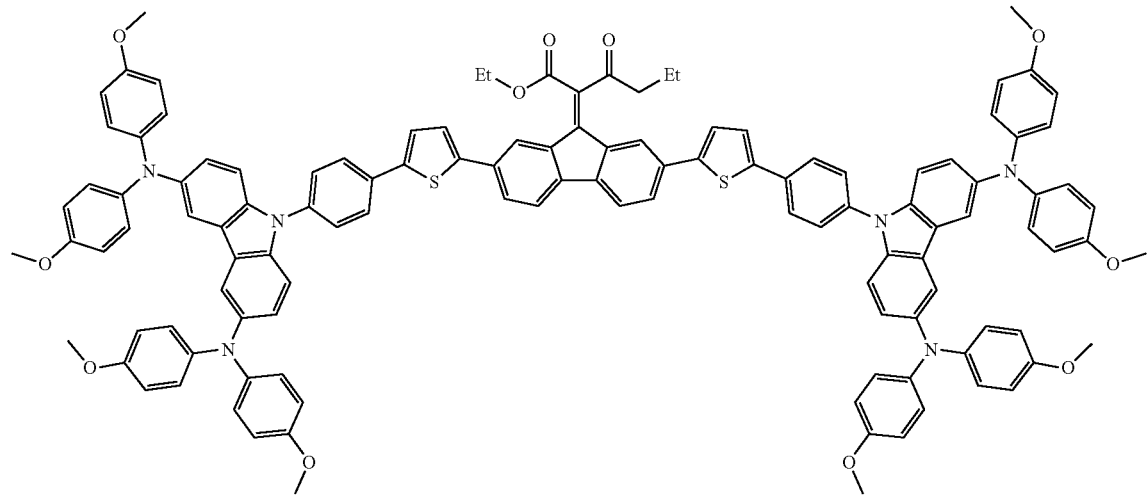
(A-97)
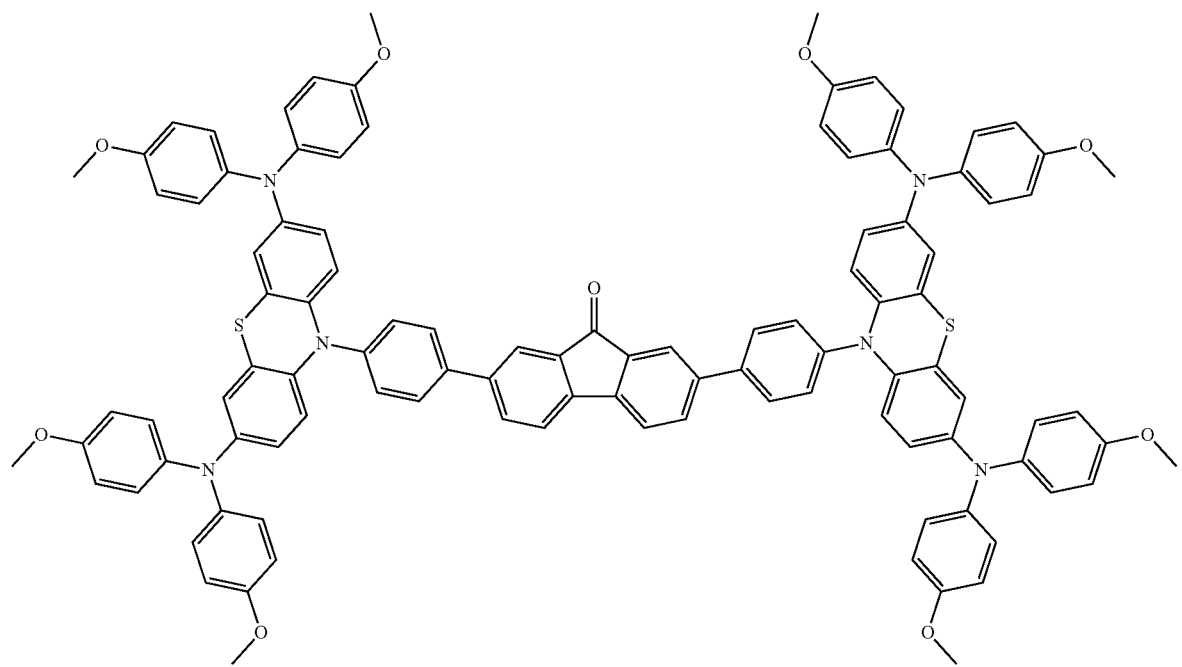

-continued
(A-98)
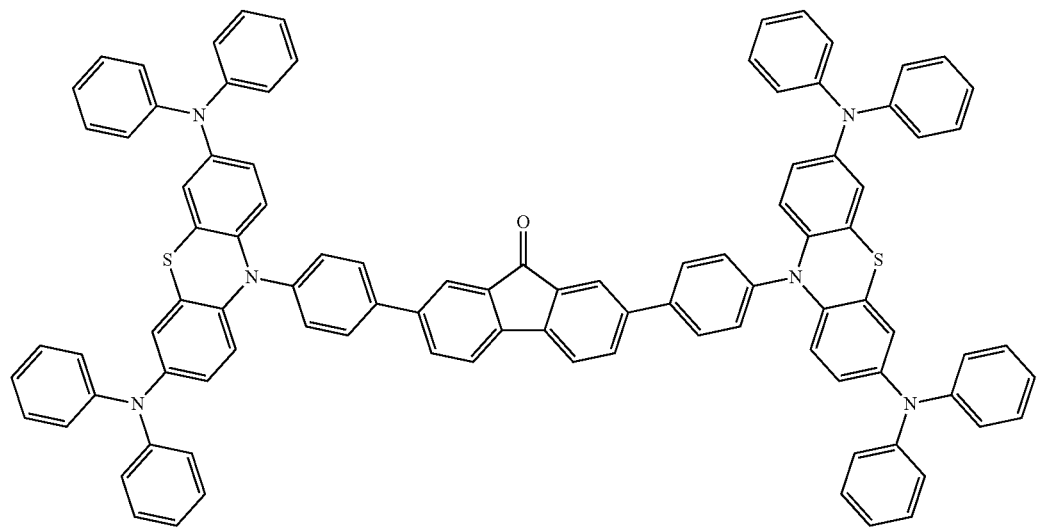
(A-99)
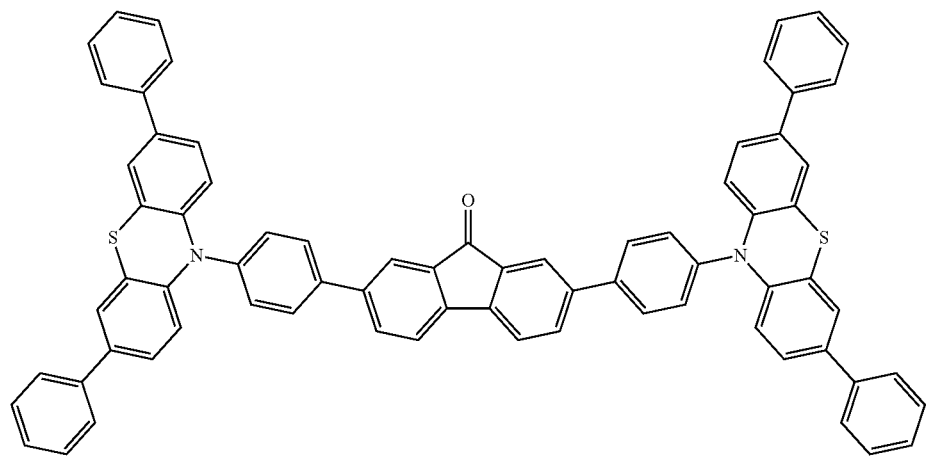
(A-100)
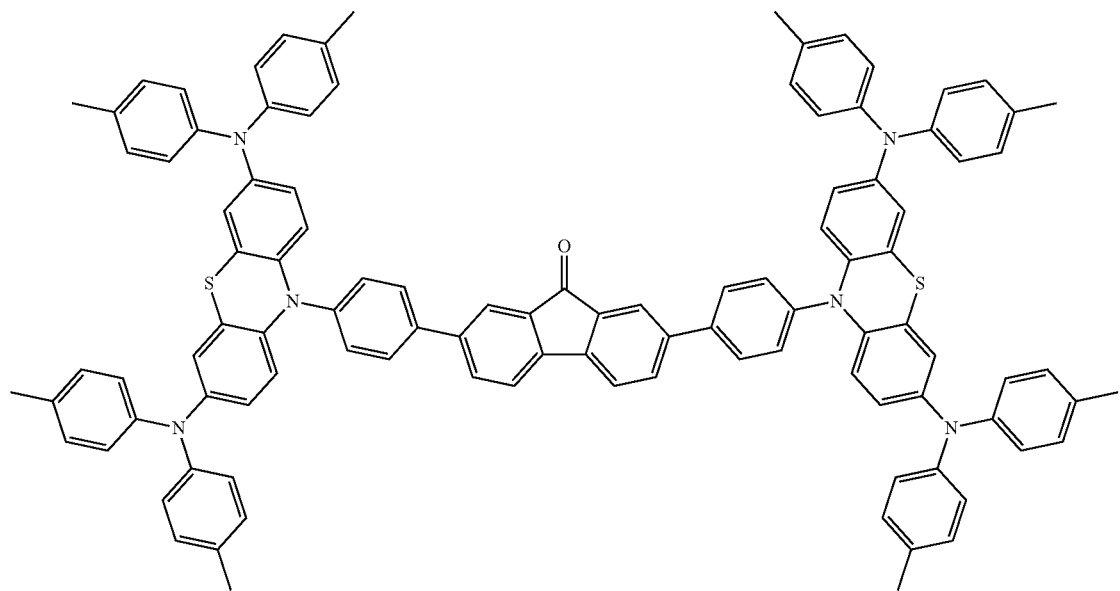

[Chem. 11]
(A-101)
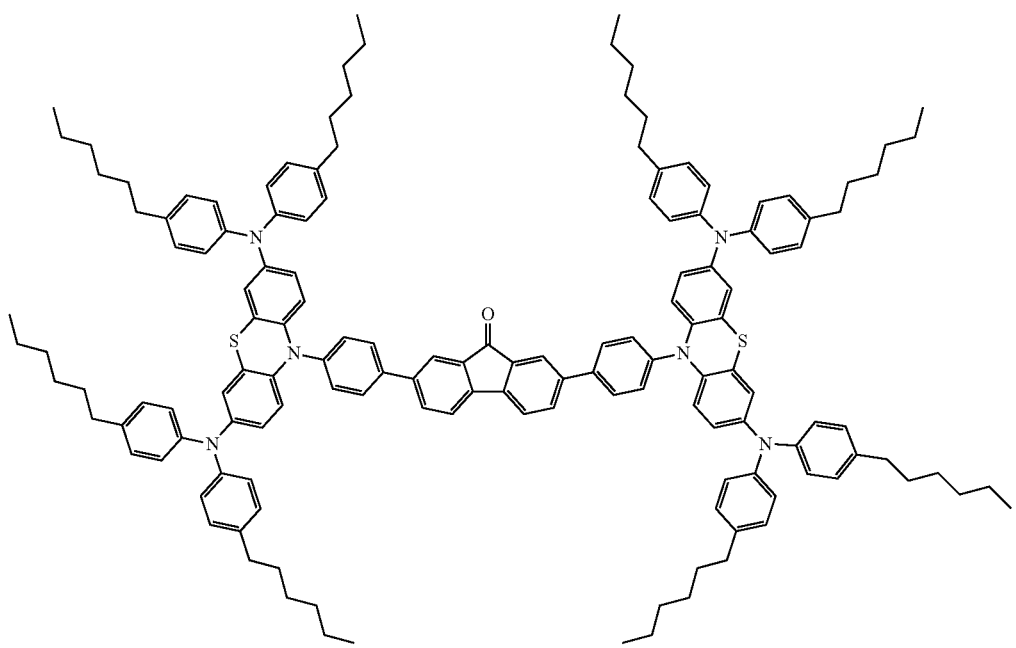
(A-102)
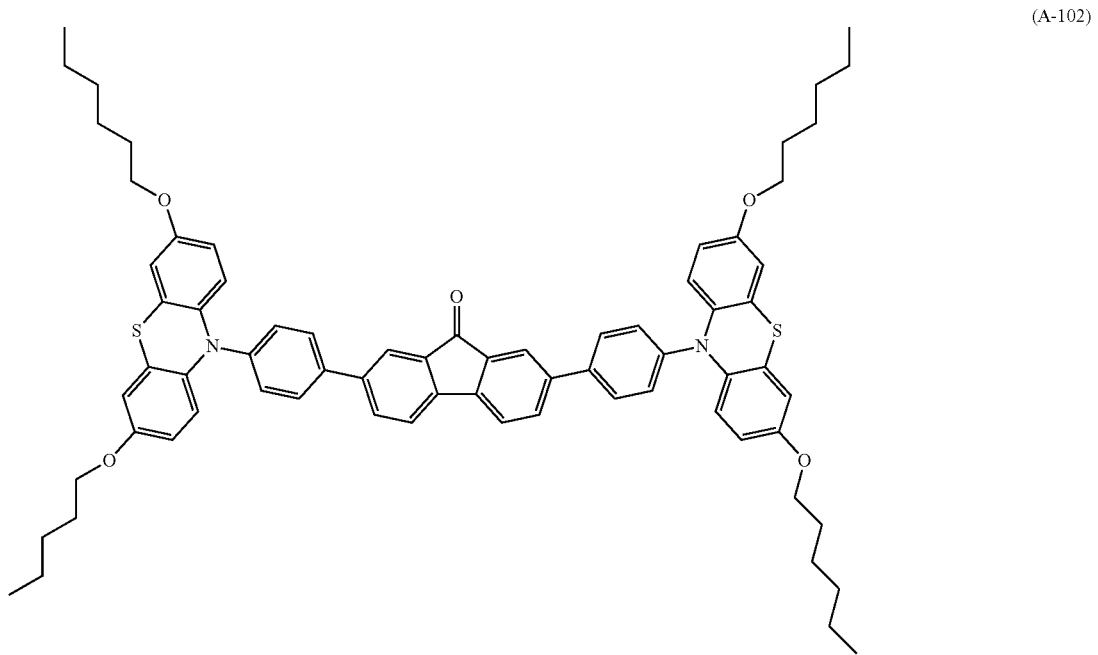

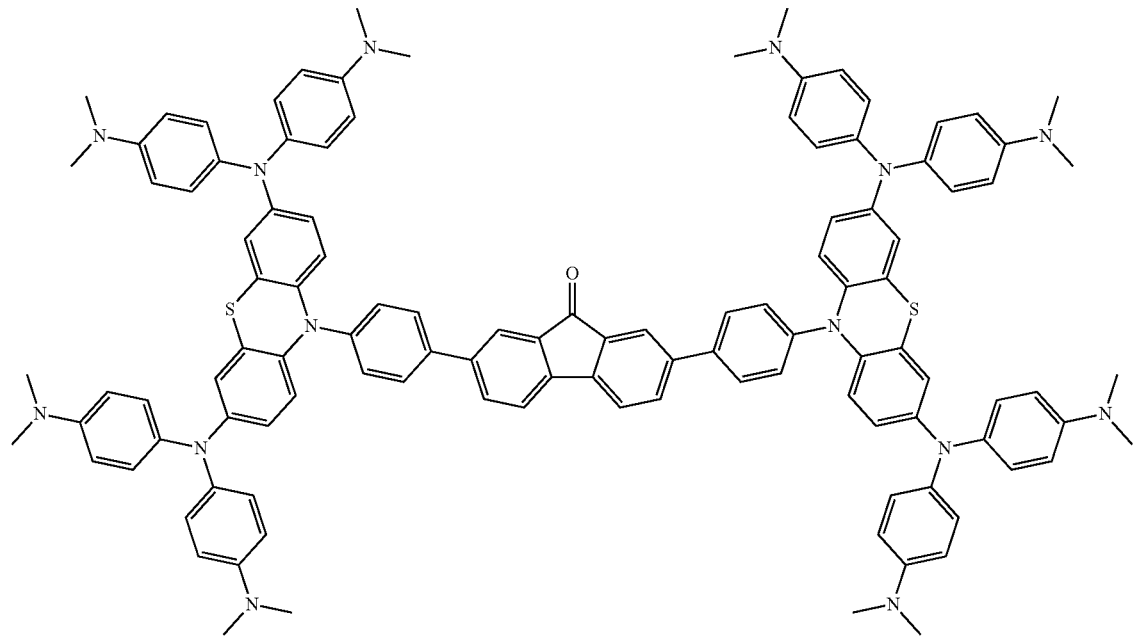
(A-103)
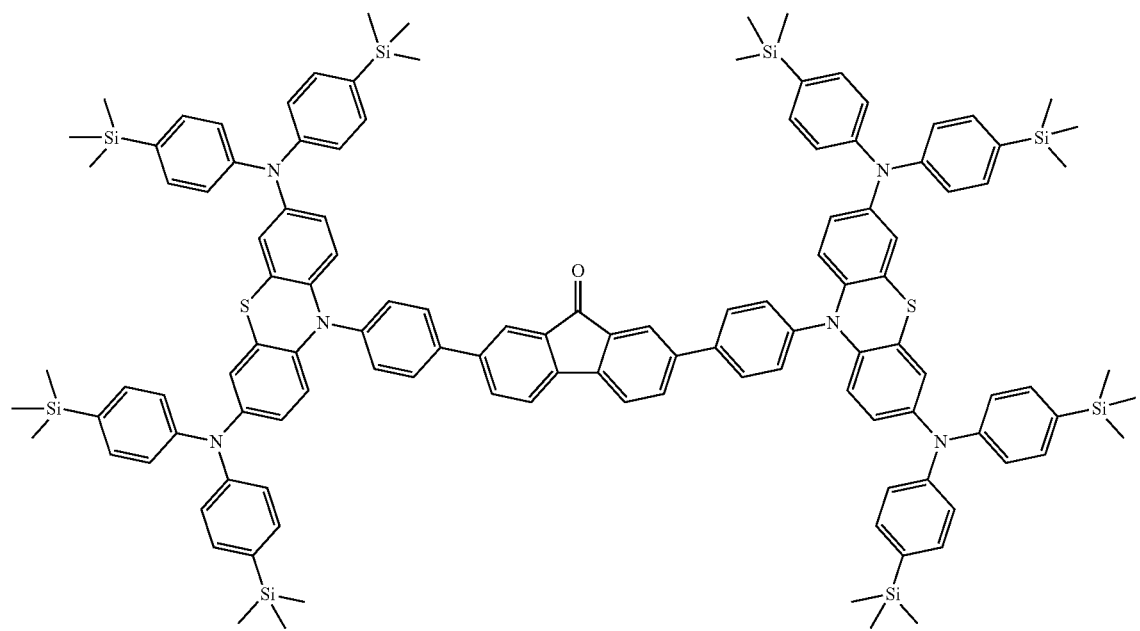
(A-104)

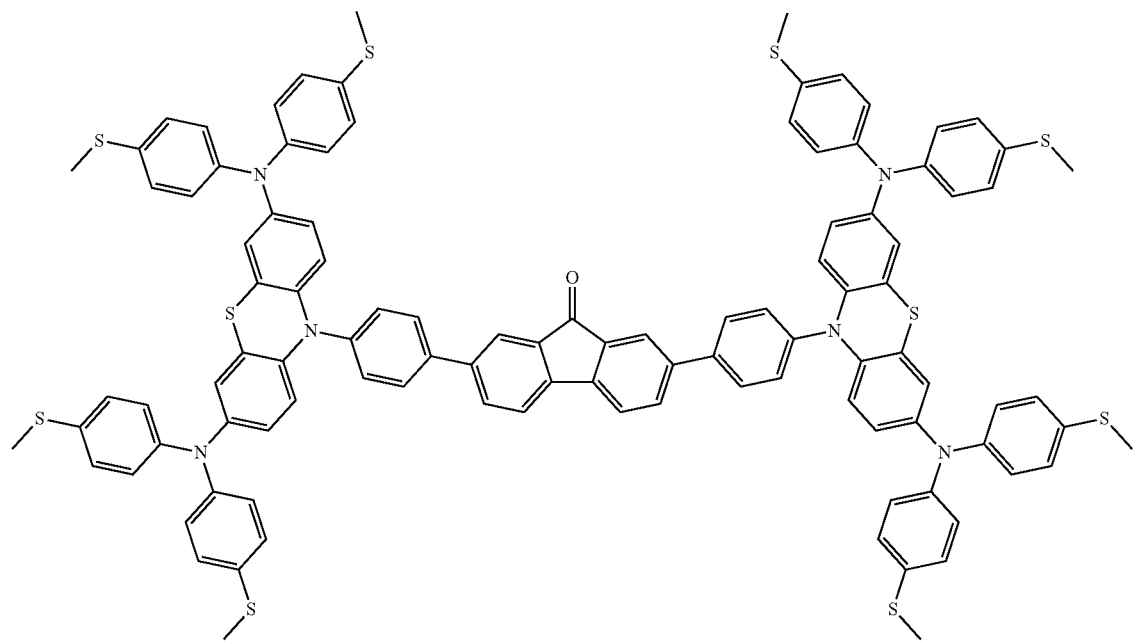
(A-105)
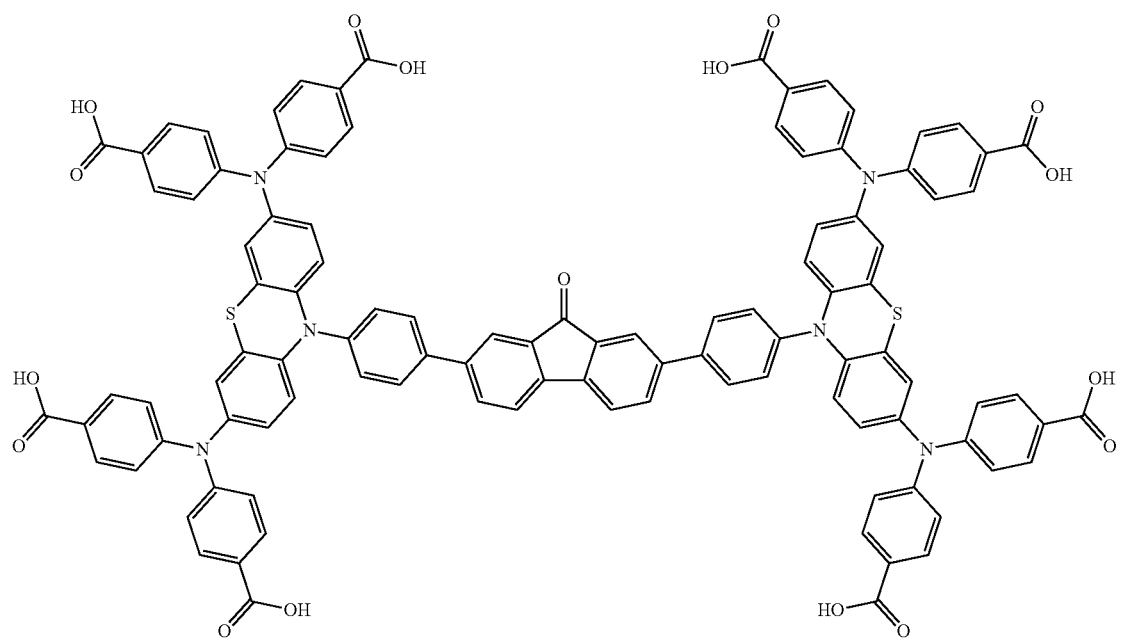
(A-106)

(A-107)
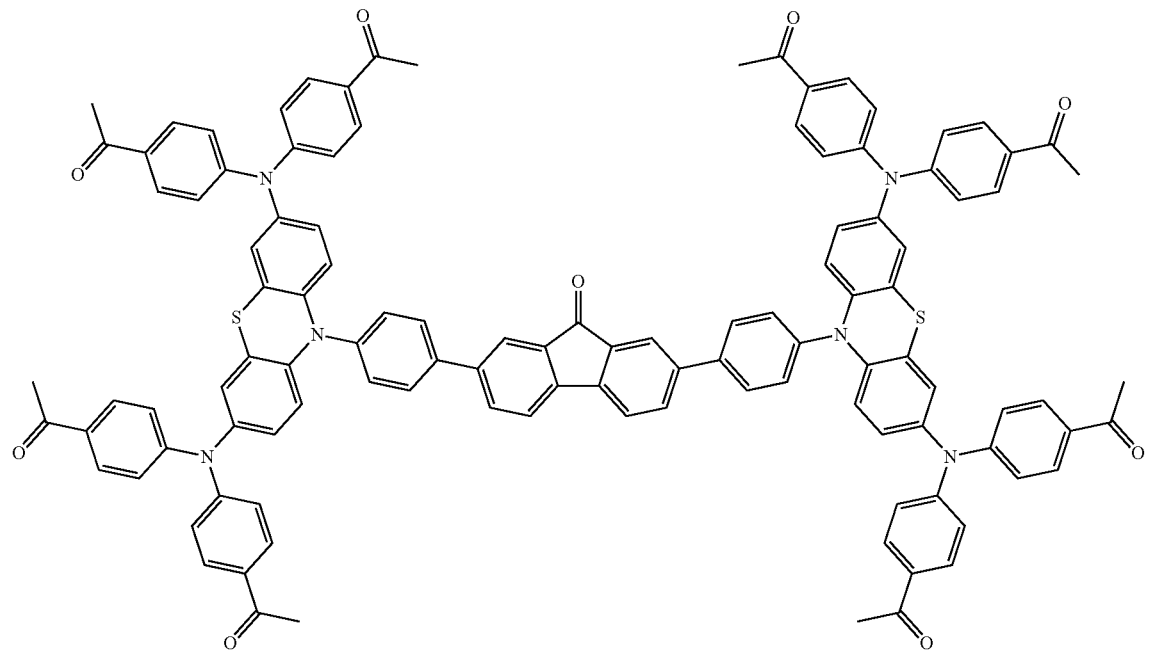
(A-108)
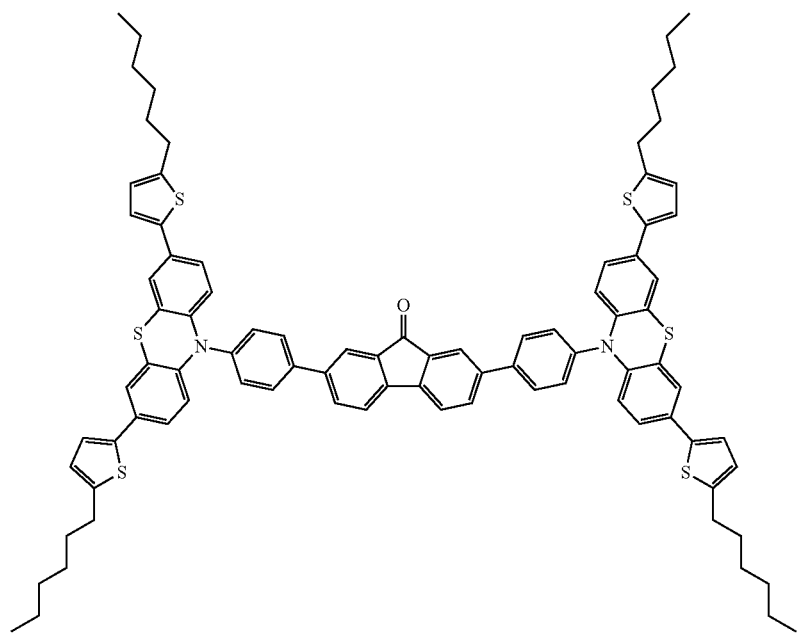

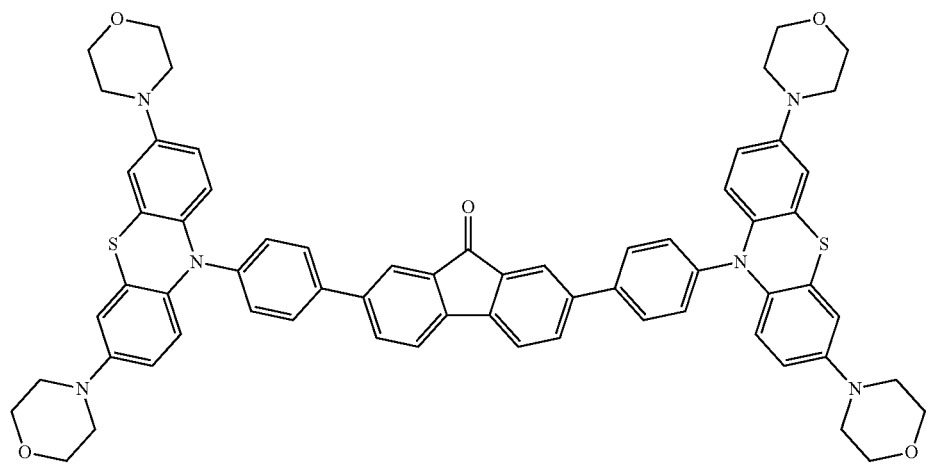
(A-109)
[Chem. 12]
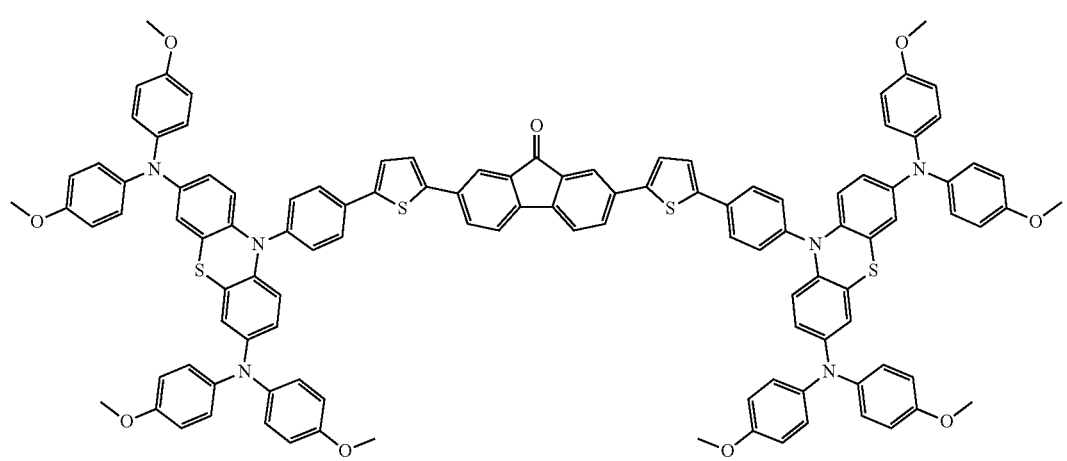
(A-110)
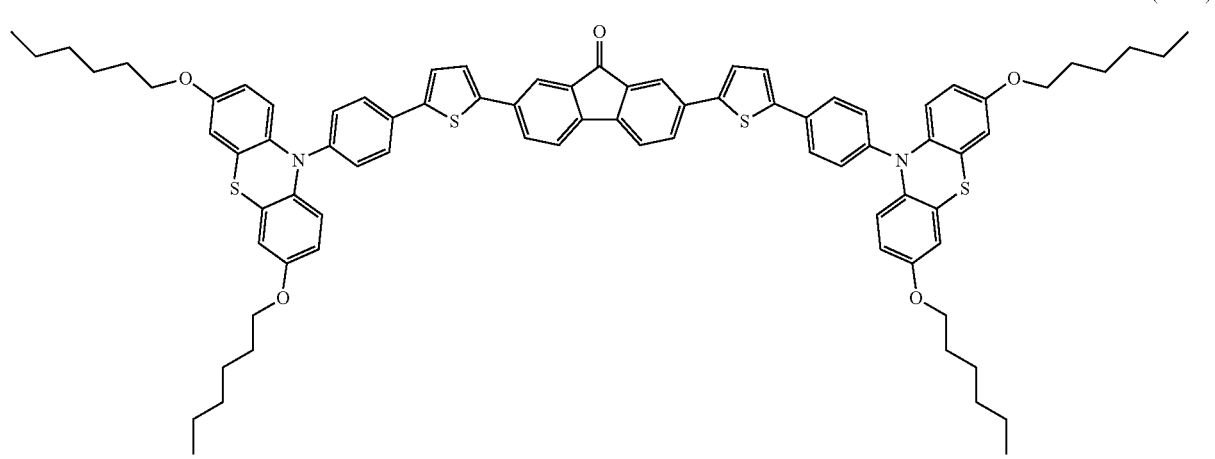
(A-111)

(A-112)
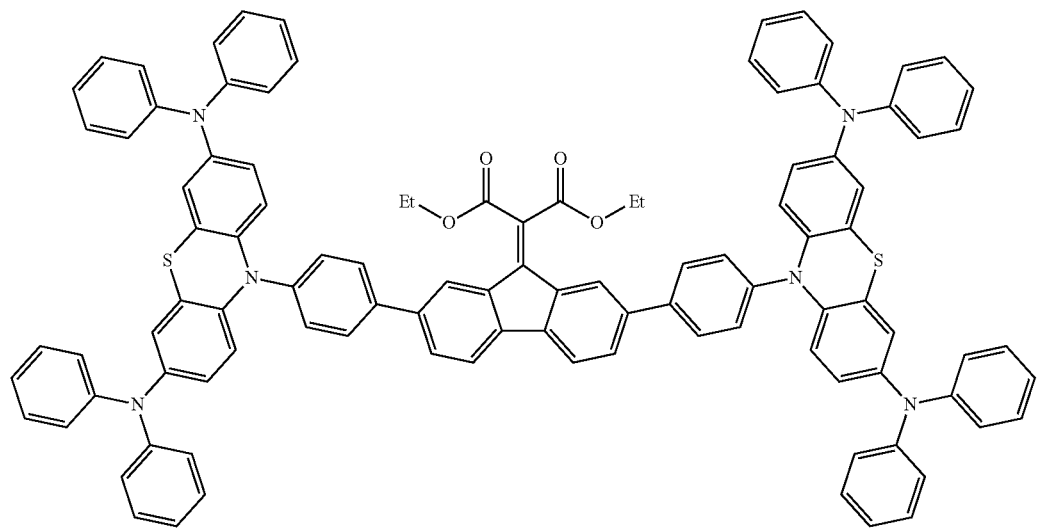
(A-113)
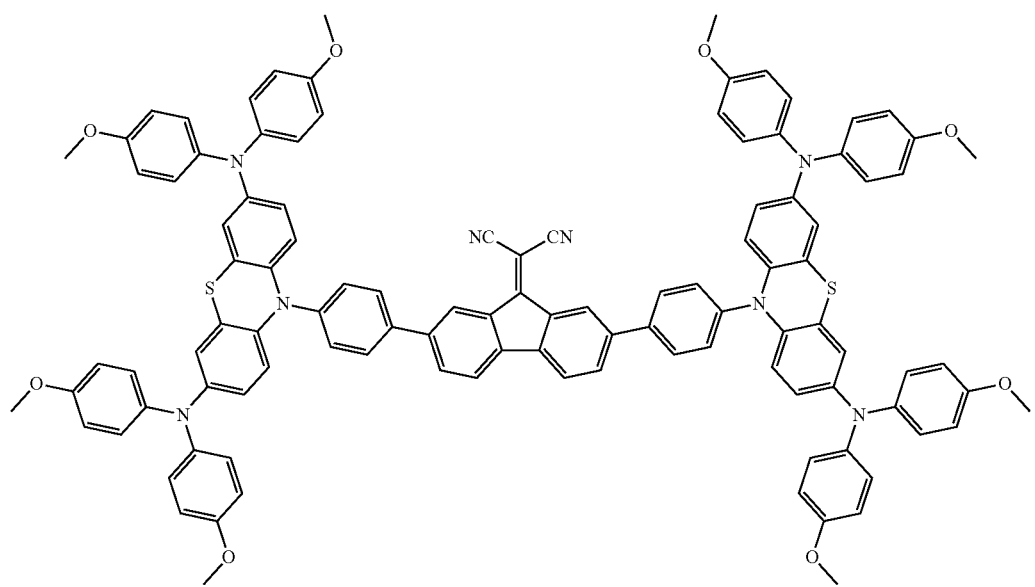

-continued
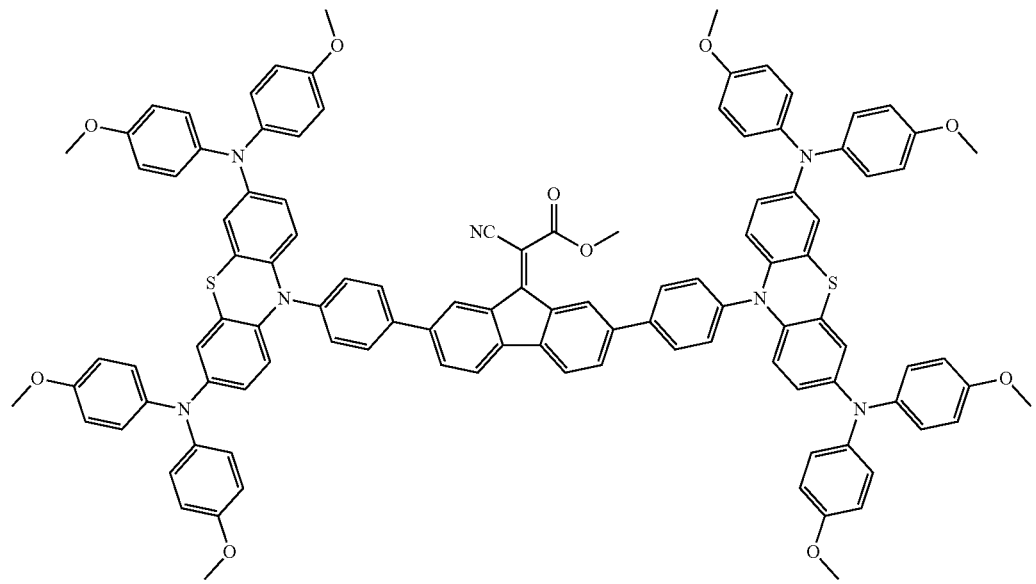
(A-114)
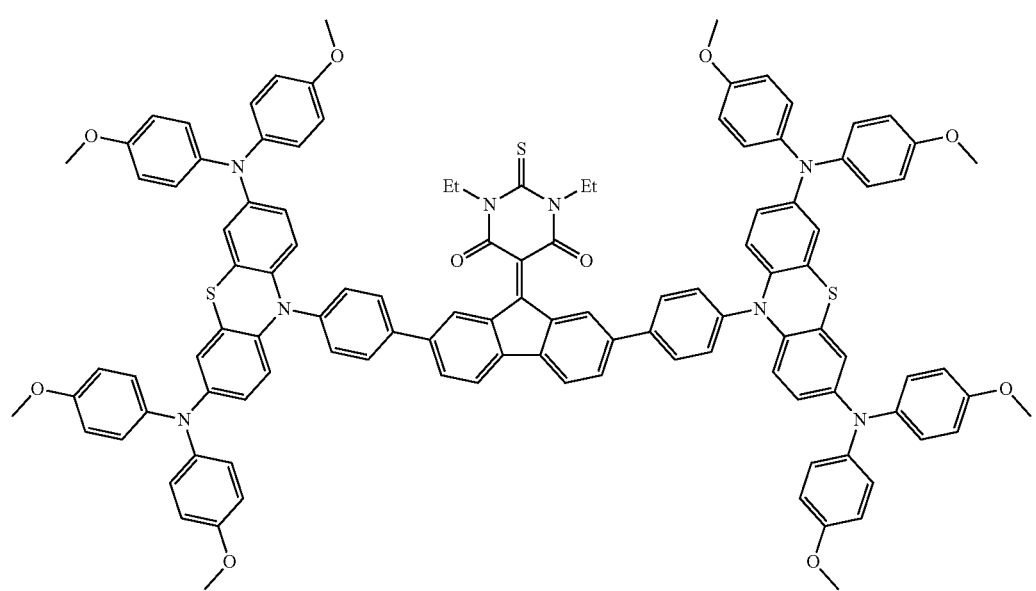
(A-115)

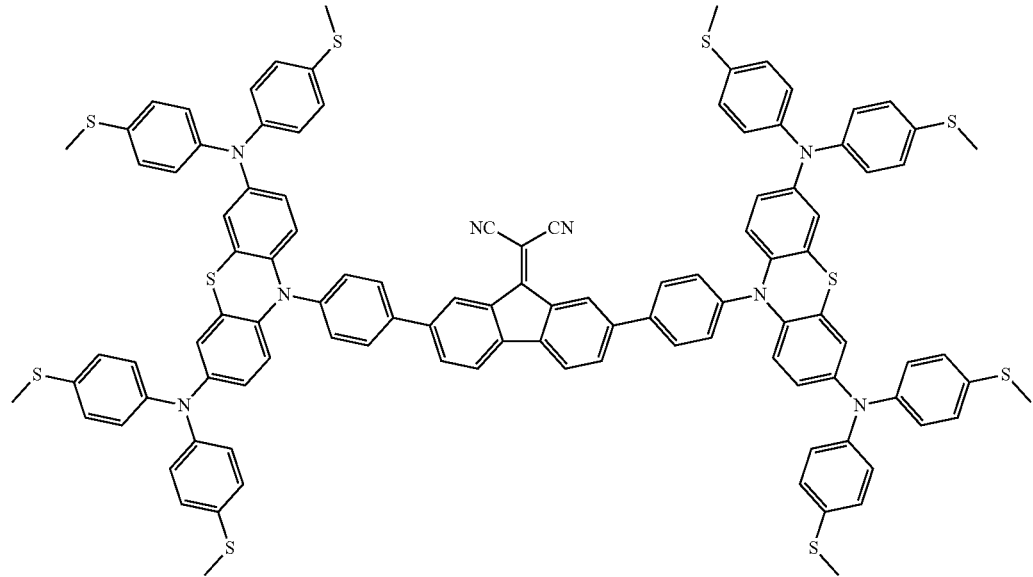
(A-116)
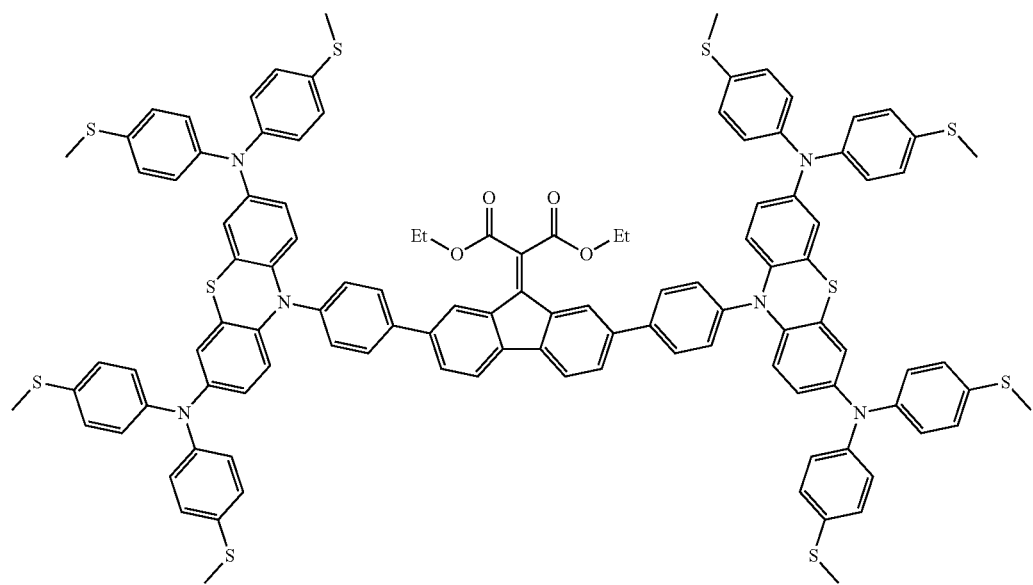
(A-117)

-continued
(A-118)
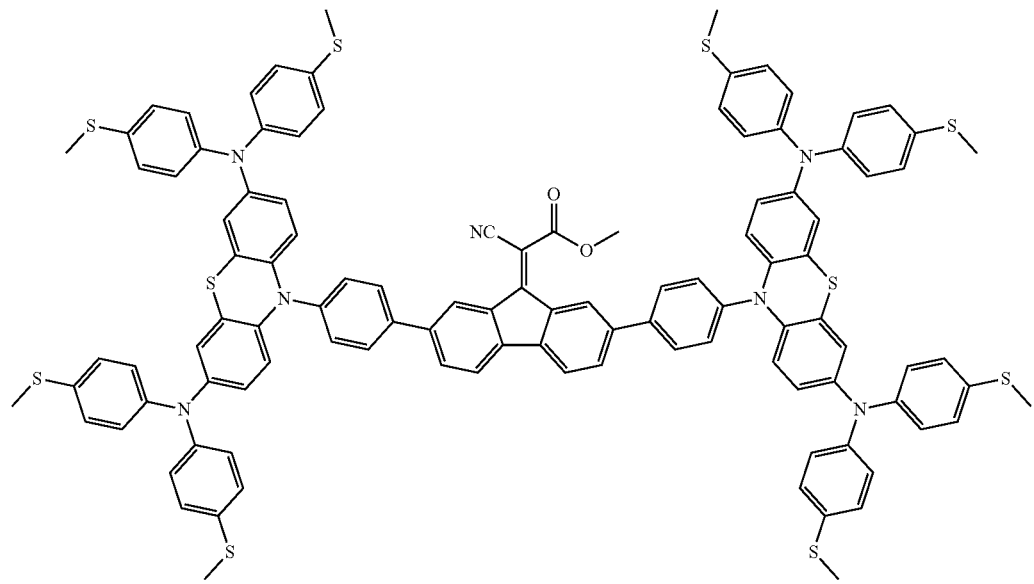
(A-119)
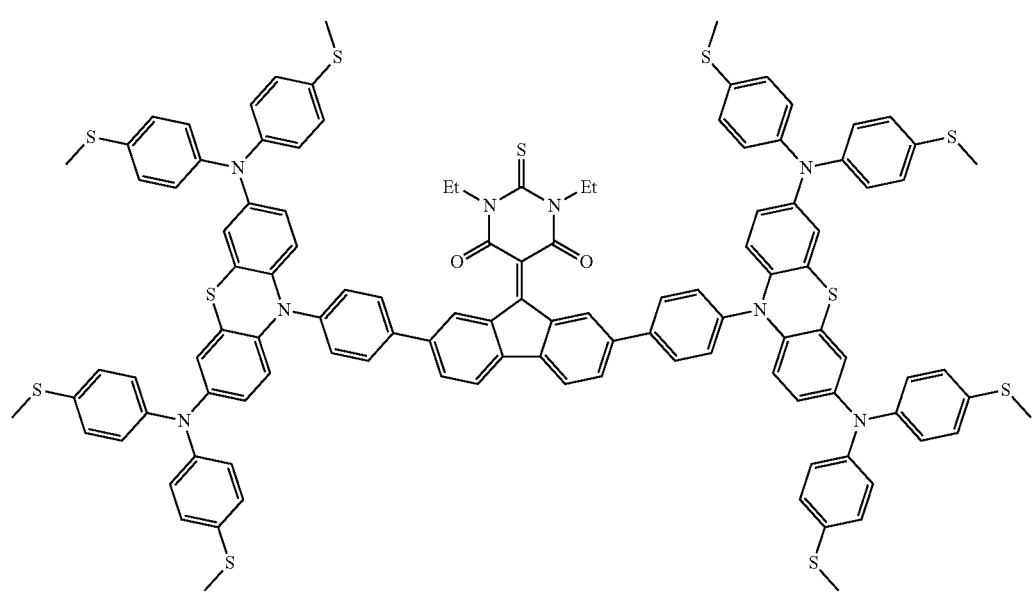
[Chem. 13]
(A-120)
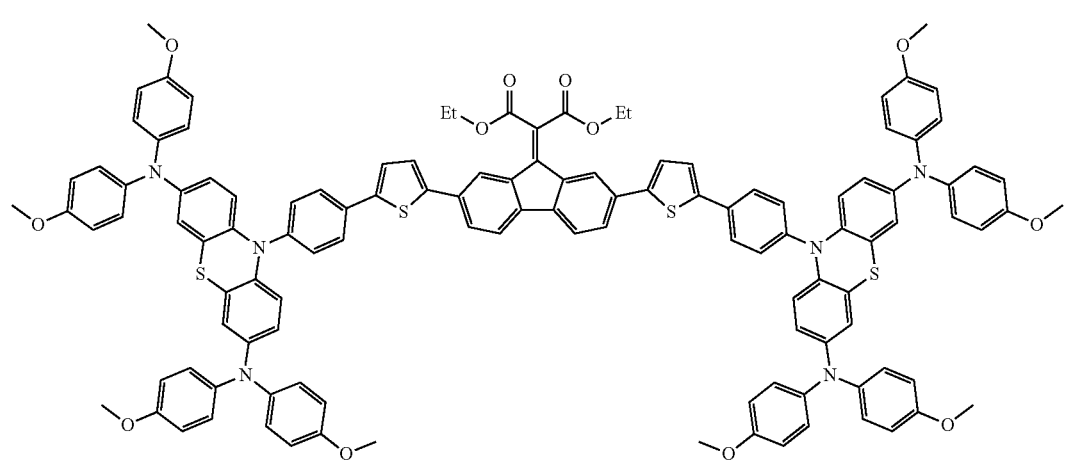

-continued
(A-121)
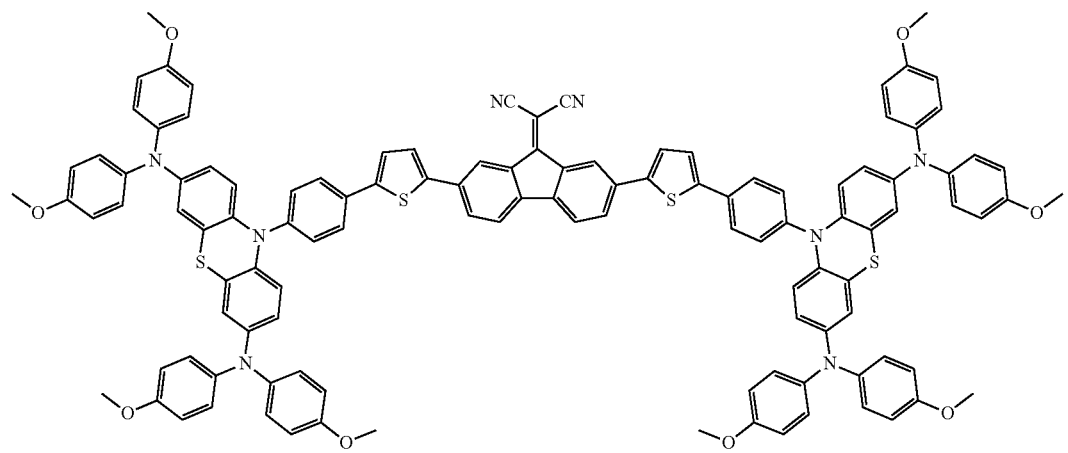
(A-122)
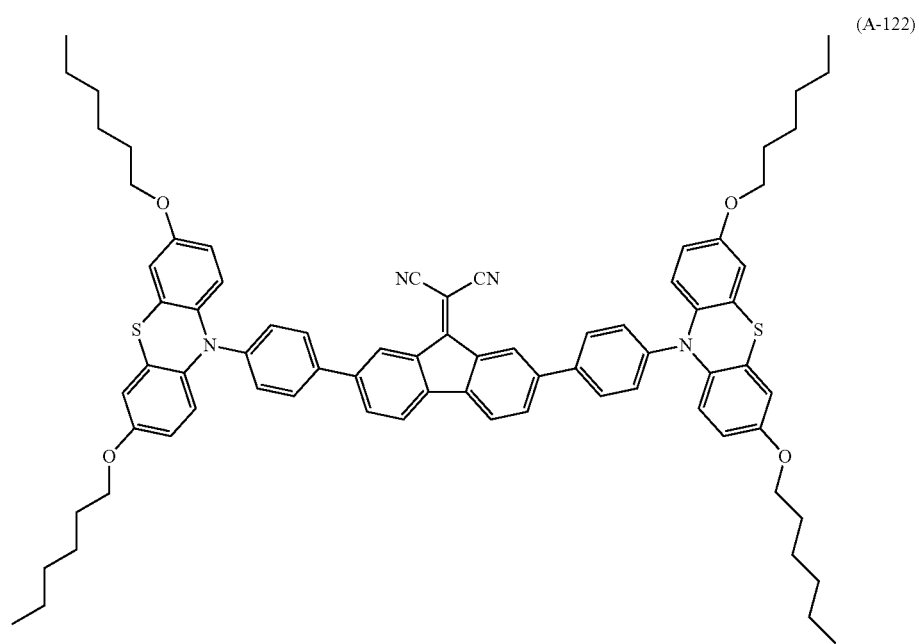

-continued
(A-123)
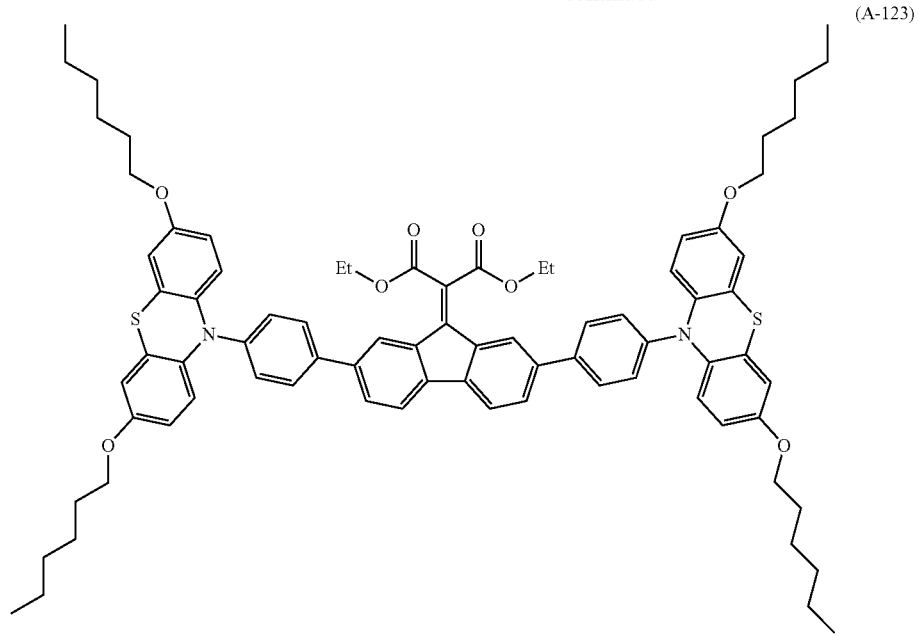
(A-124)
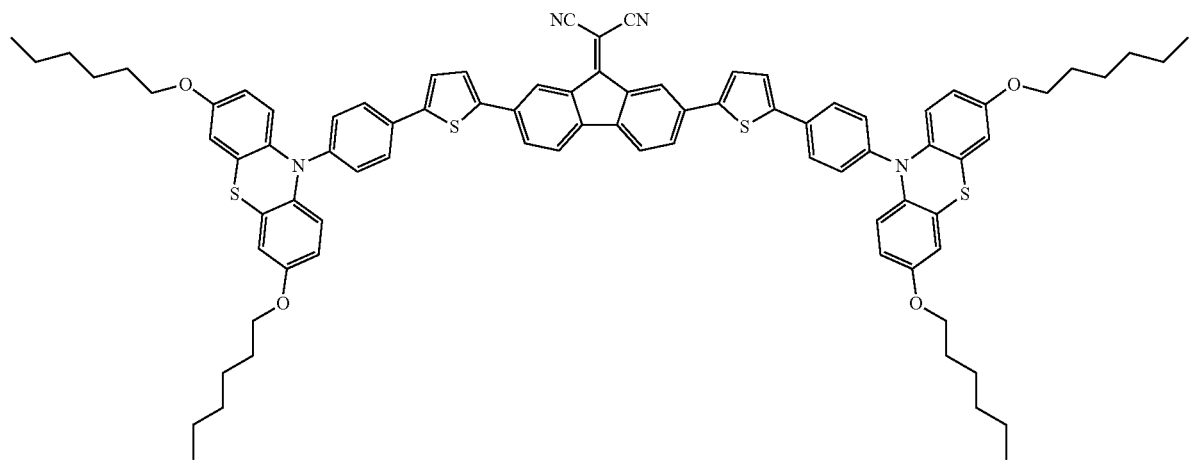
(A-125)
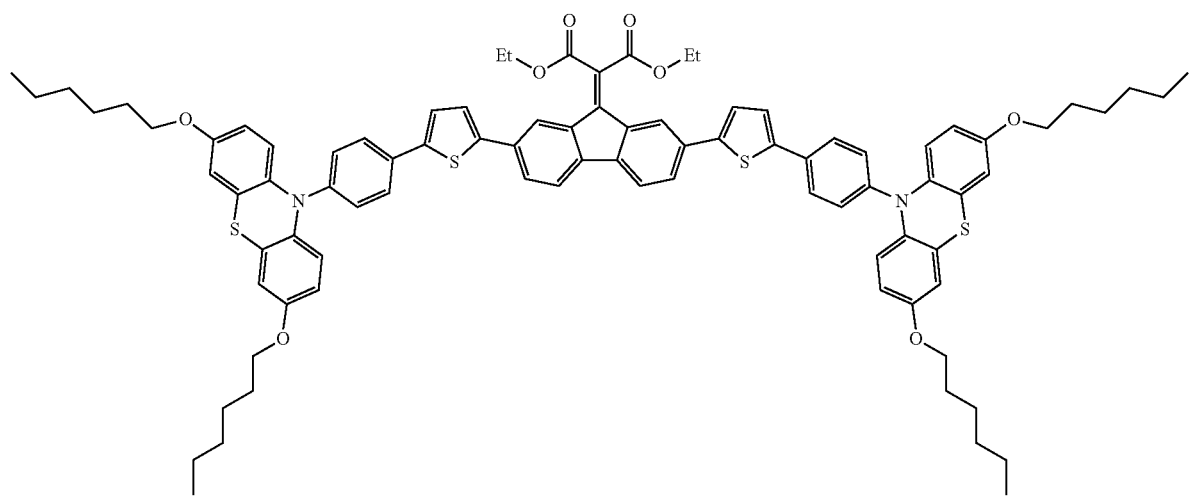

-continued
(A-126)
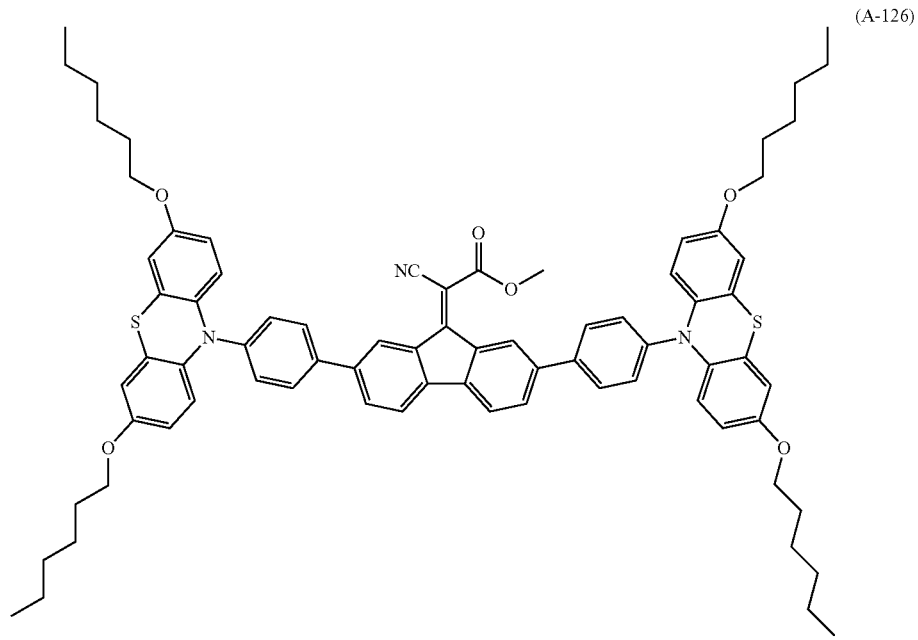
(A-127)
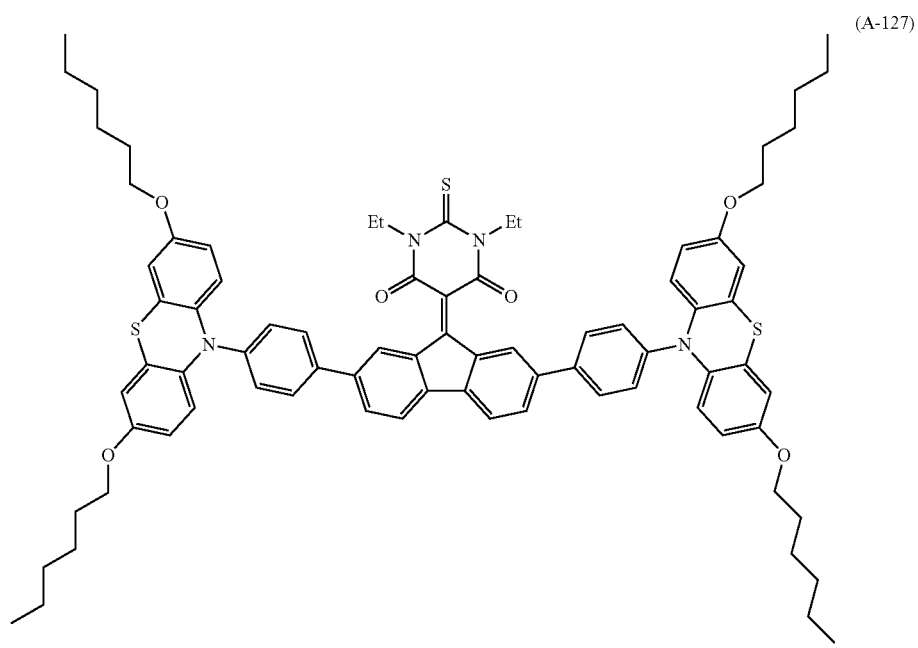

[Chem. 14]
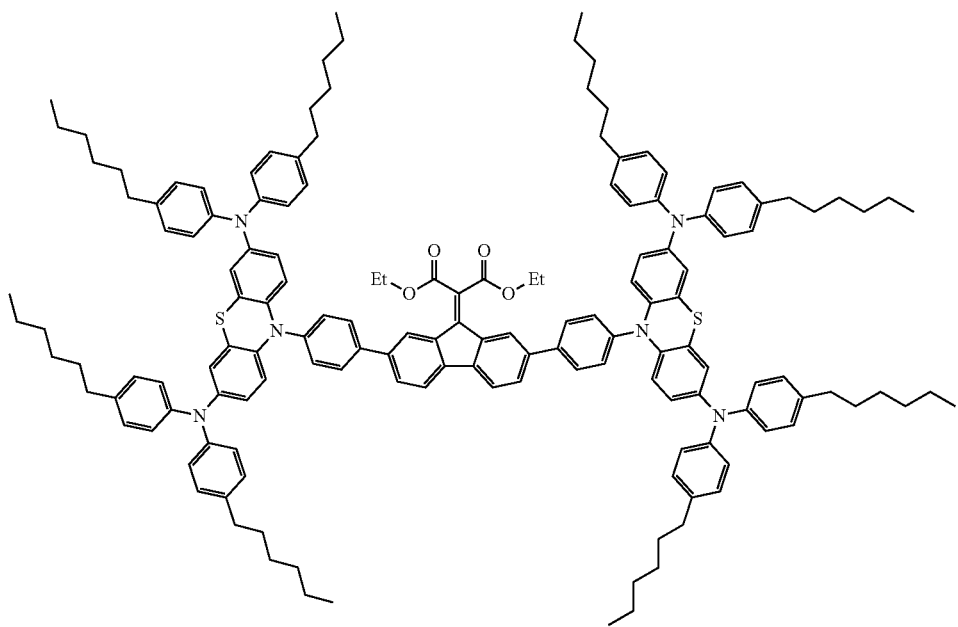
(A-128)
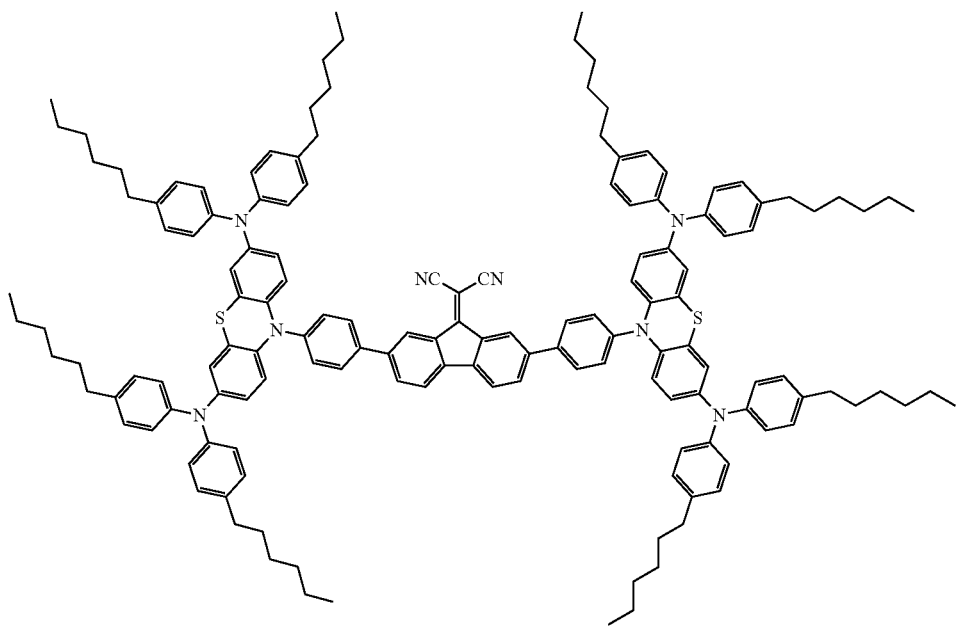
(A-129)

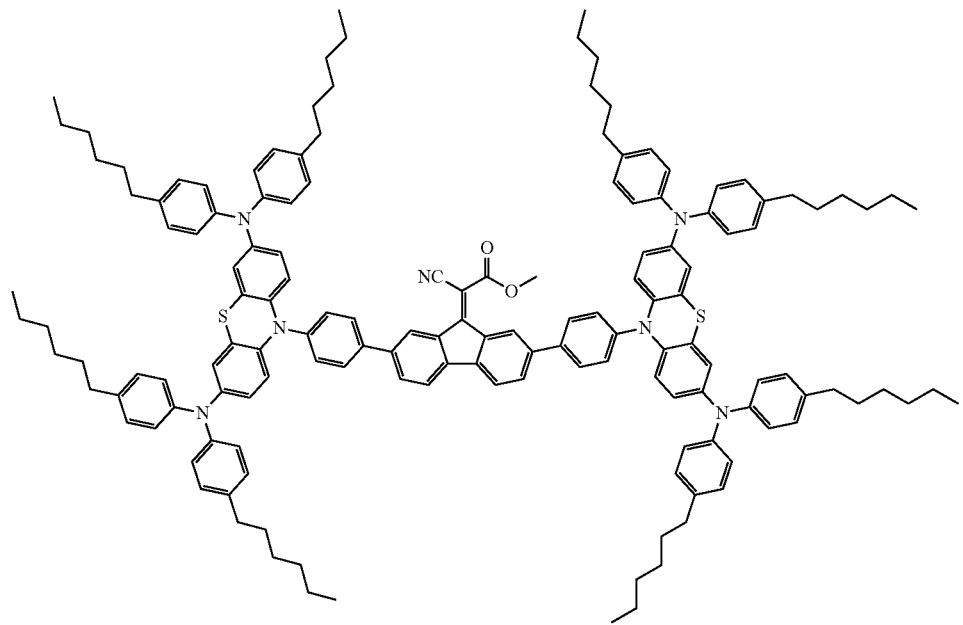
(A-130)
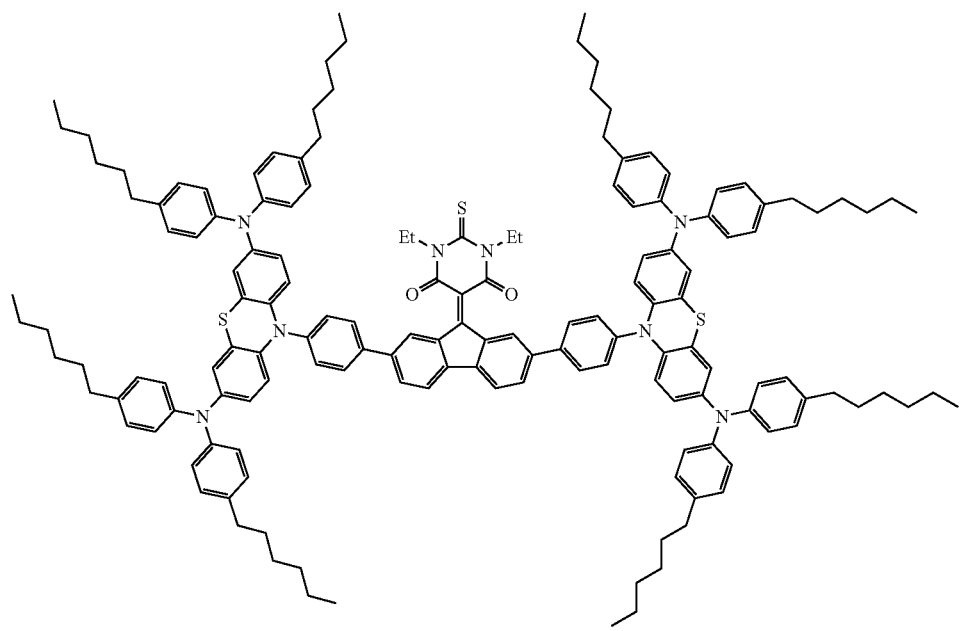
(A-131)

(A-132)
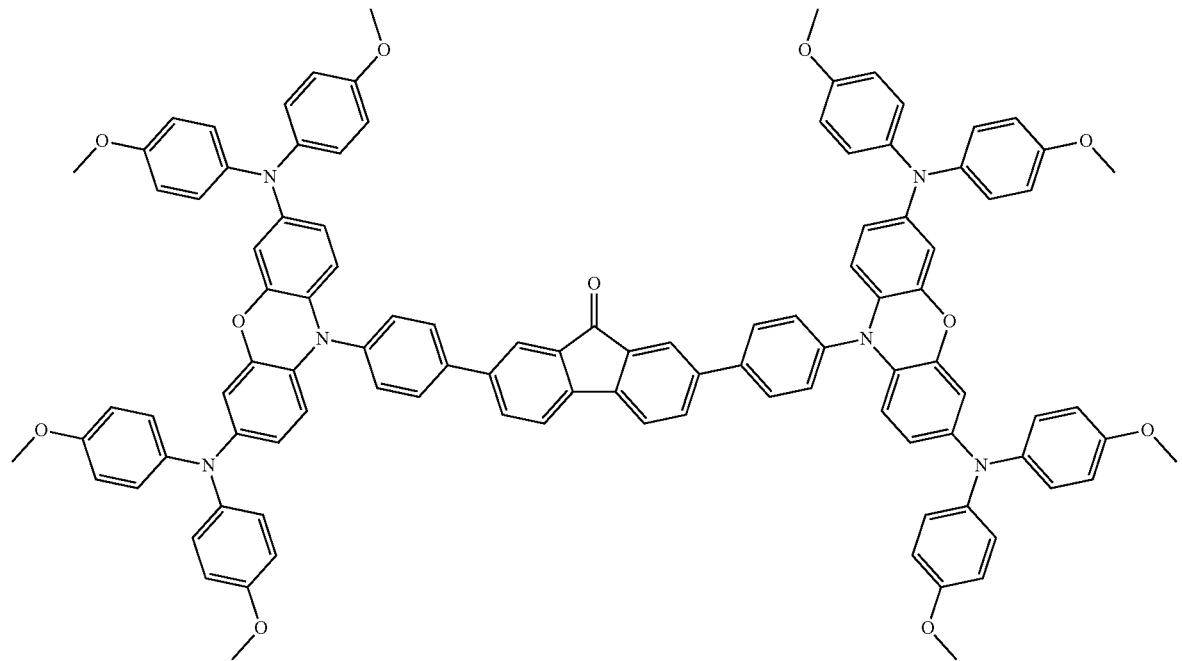
(A-133)
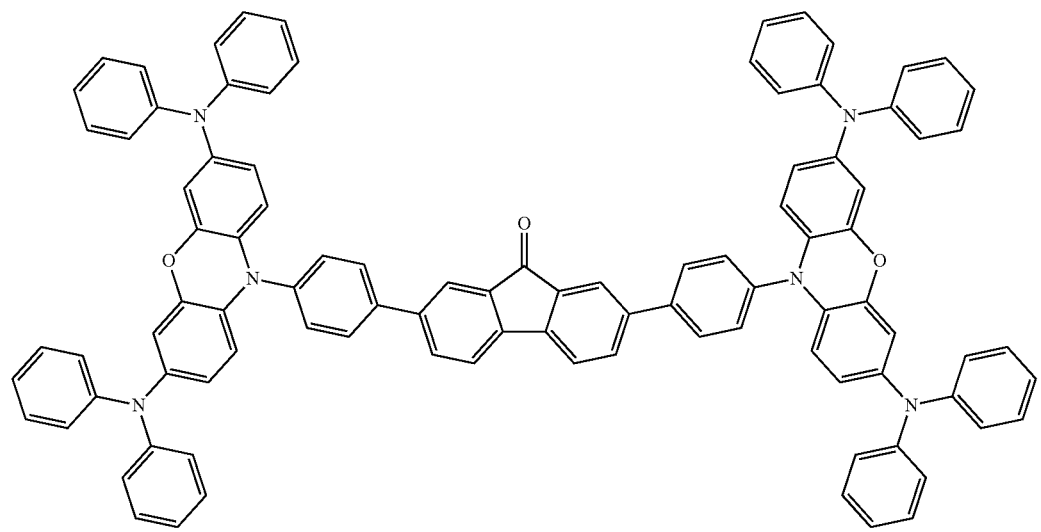

(A-134)
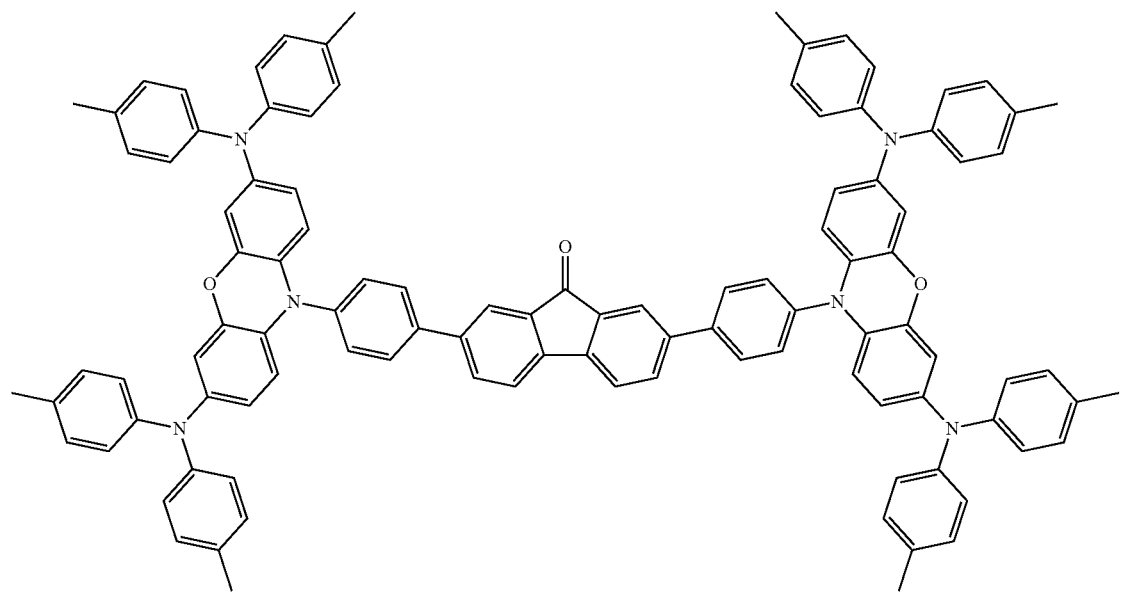
(A-135)
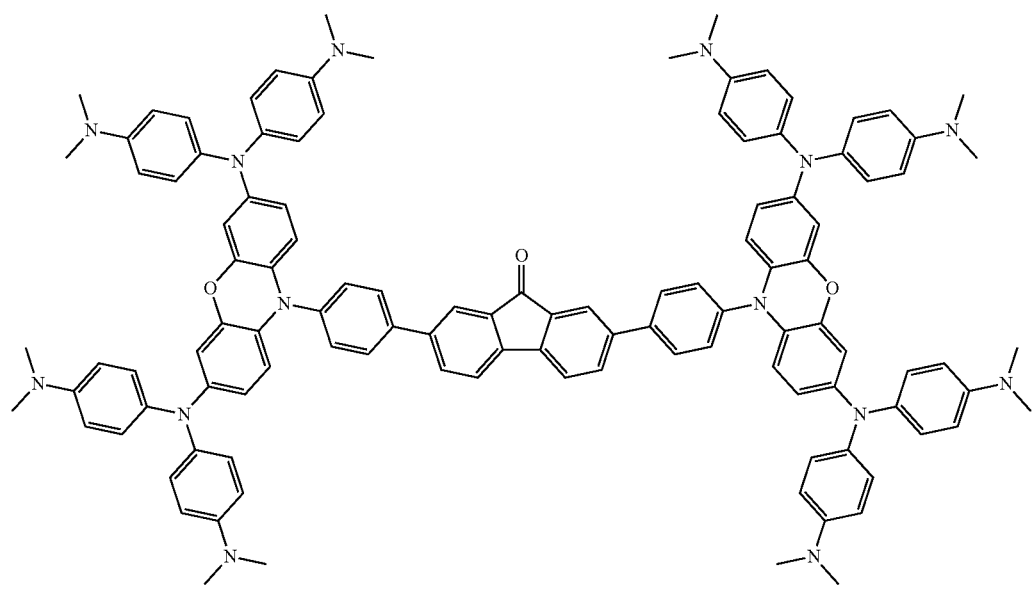

[Chem. 15]
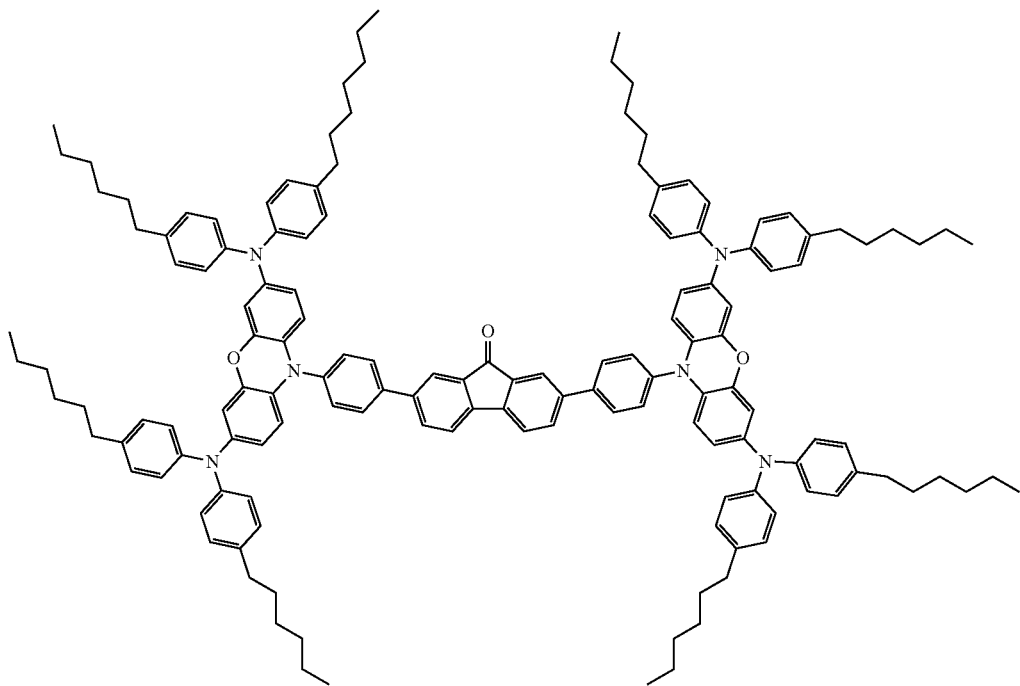
(A-136)
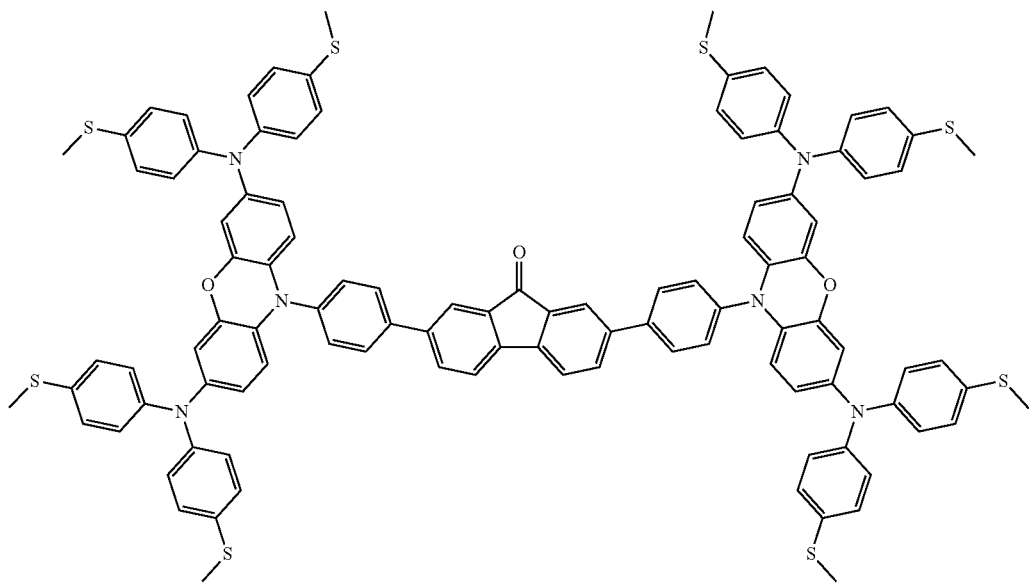
(A-137)

-continued
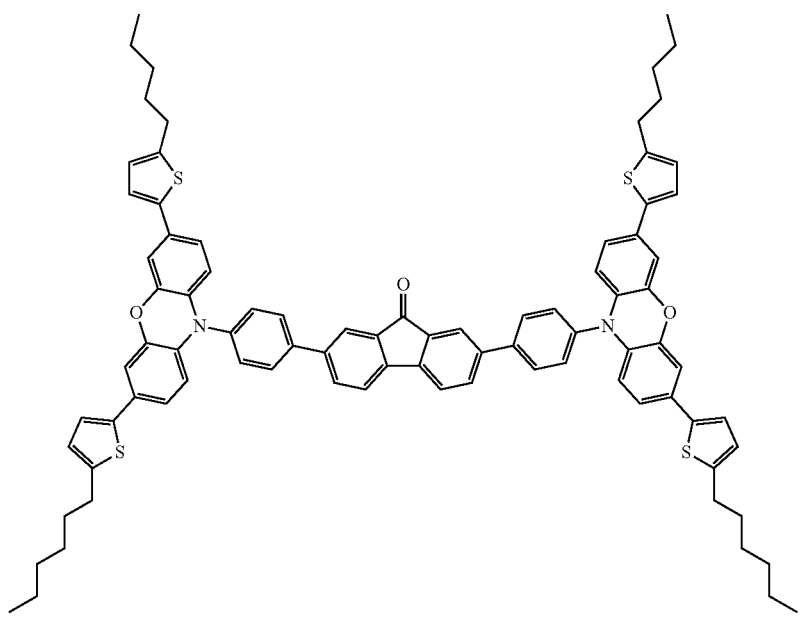
(A-138)
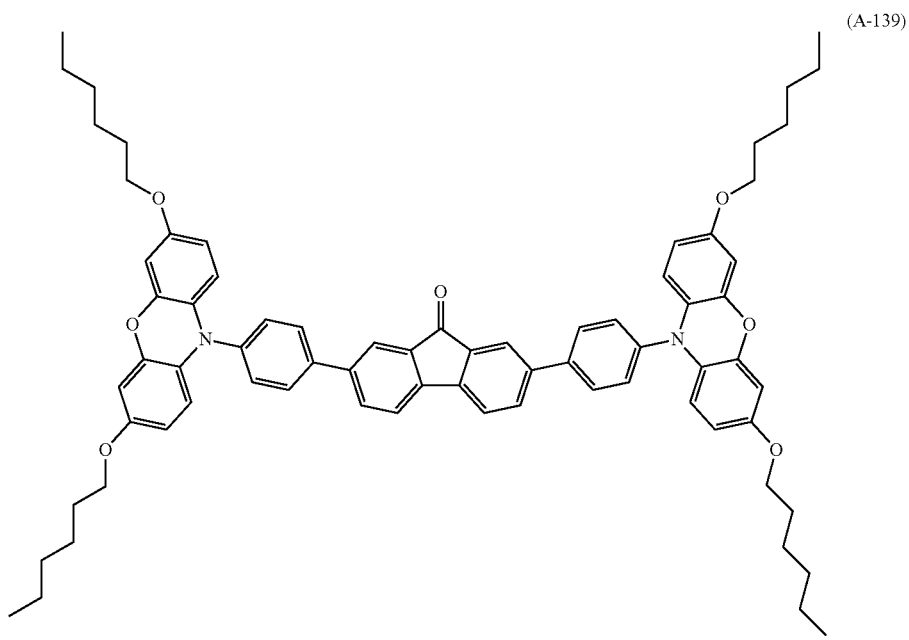
(A-139)

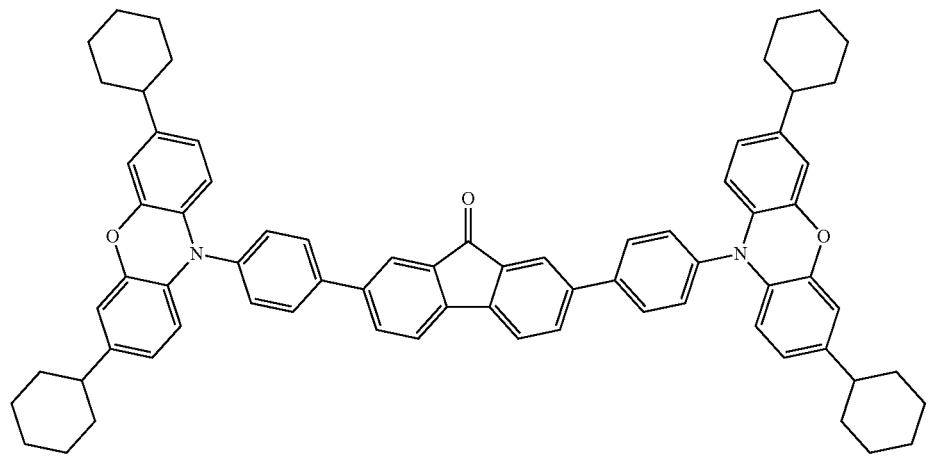
(A-140)
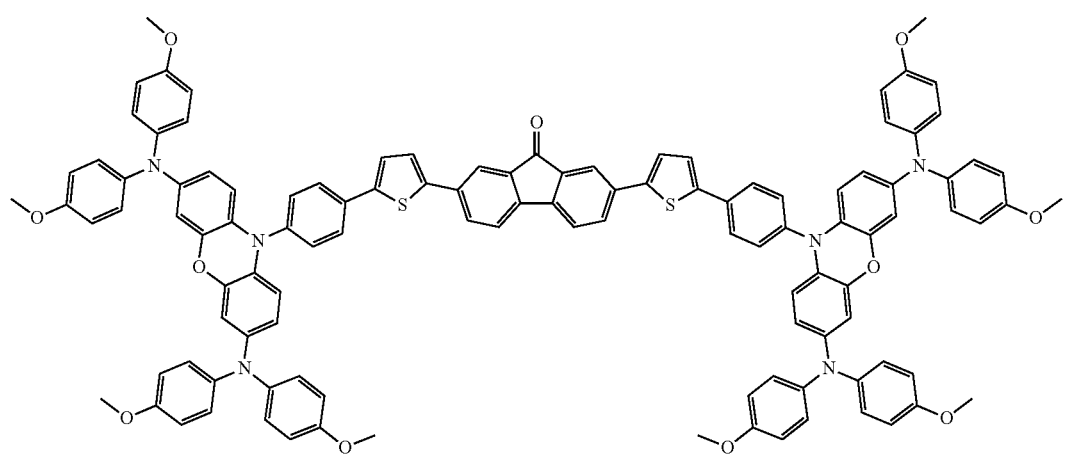
(A-141)
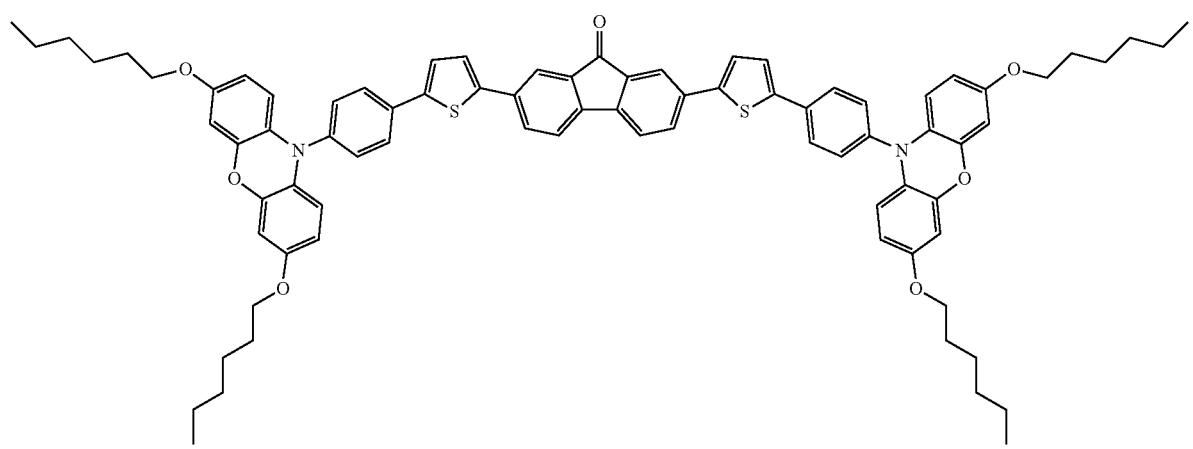
(A-142)

(A-143)
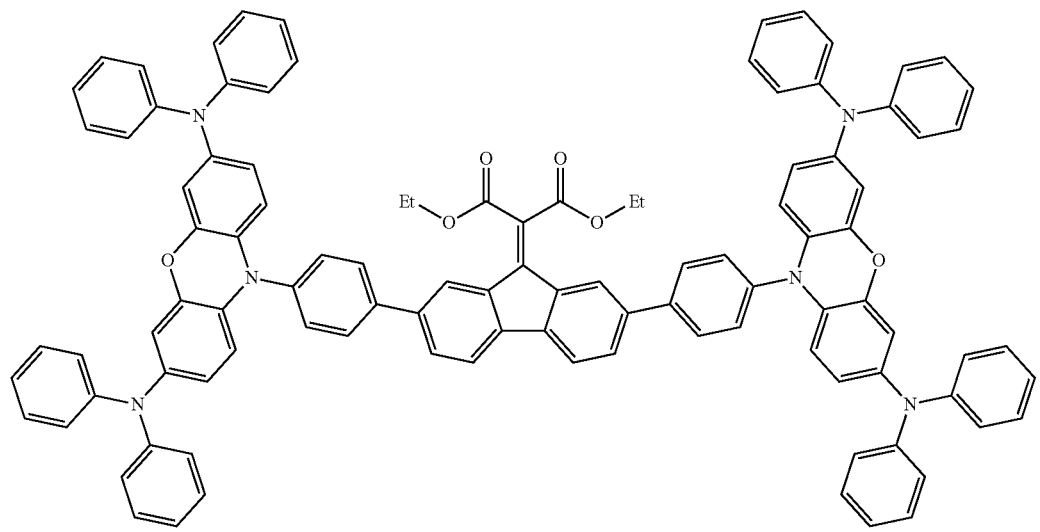
(A-144)
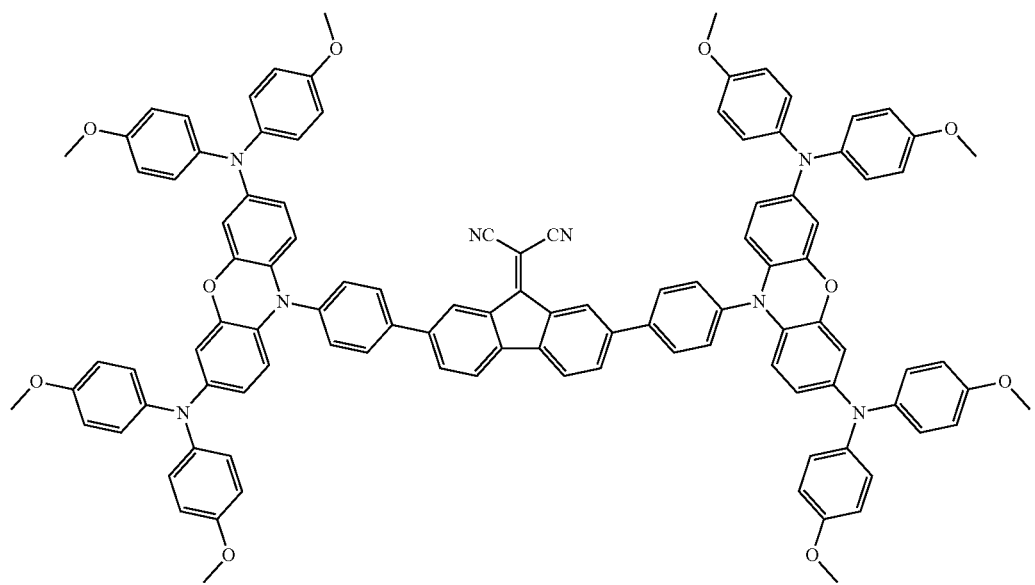

[Chem. 16]
(A-145)
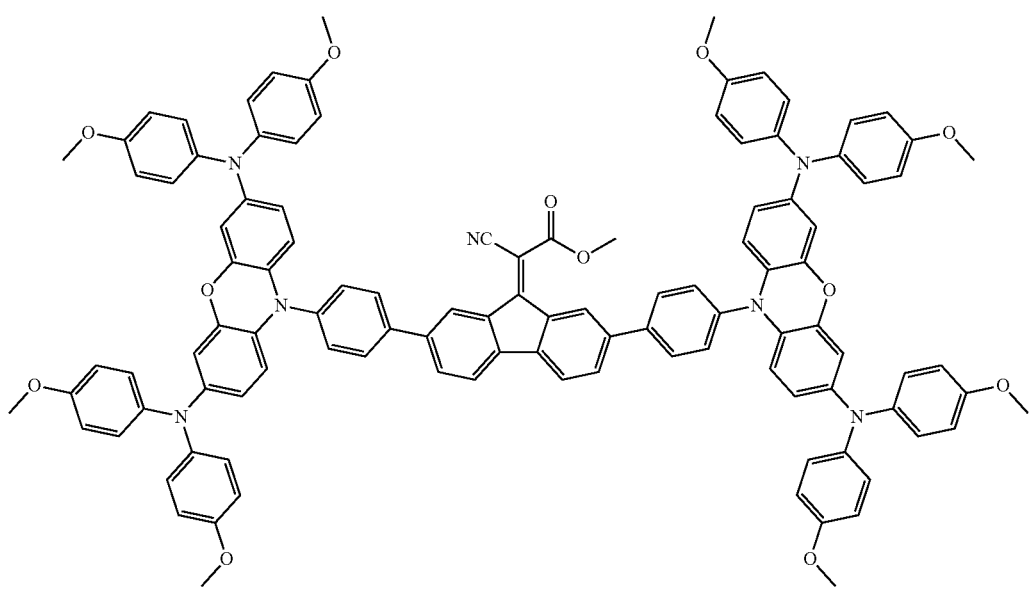
(A-146)
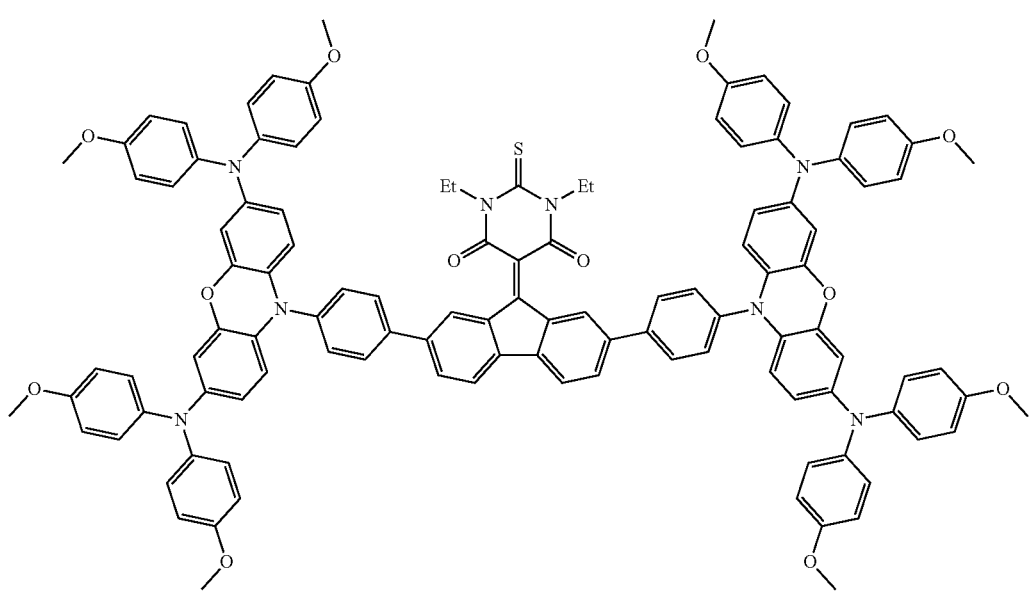
(A-147)
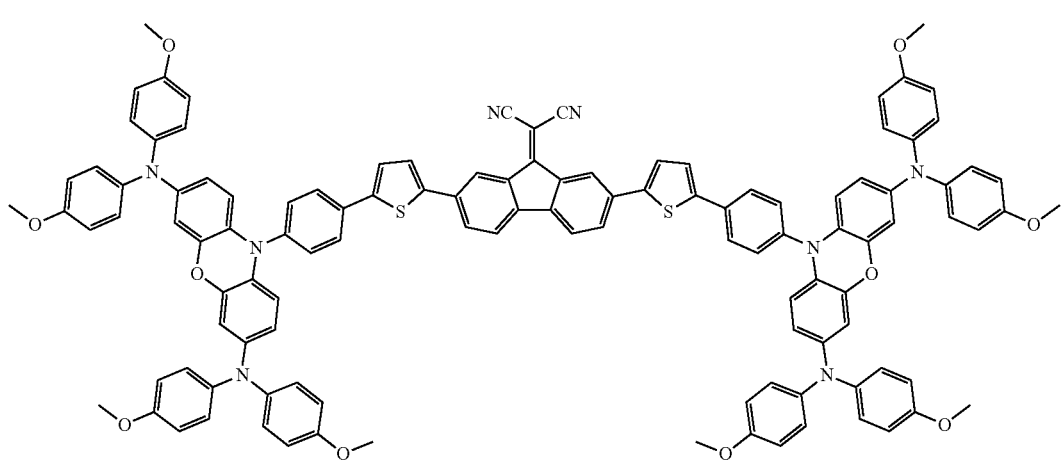

(A-148)
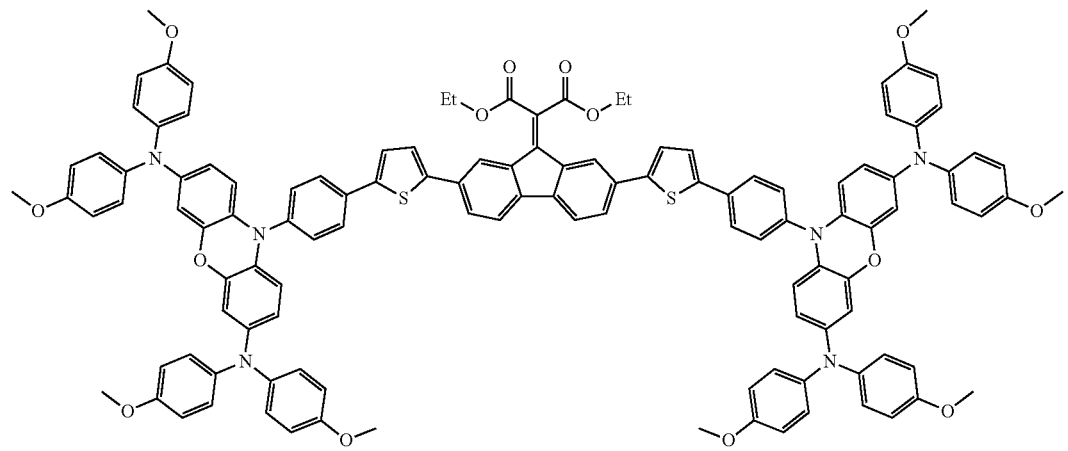
(A-149)
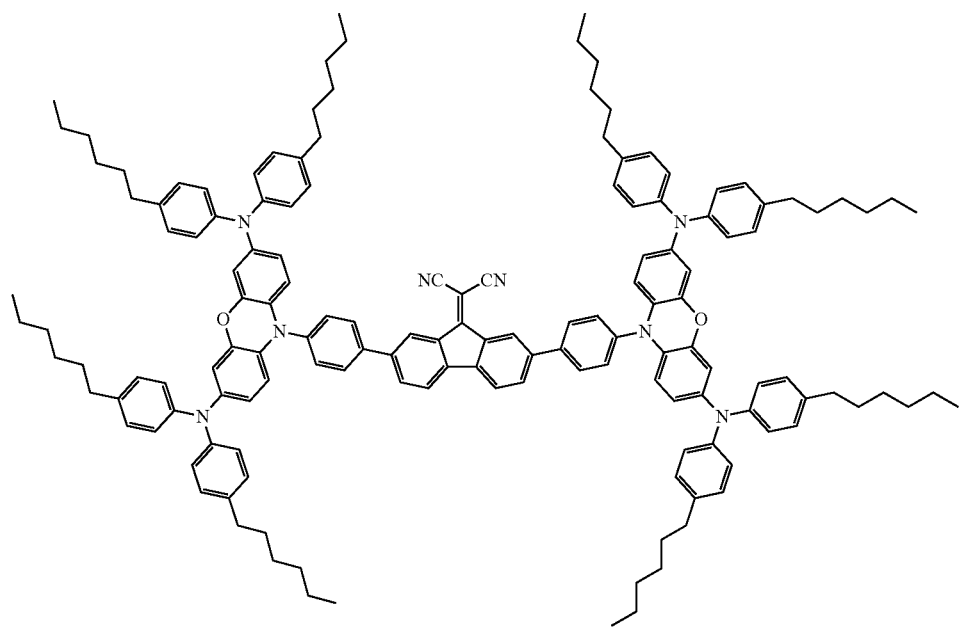

-continued
(A-150)
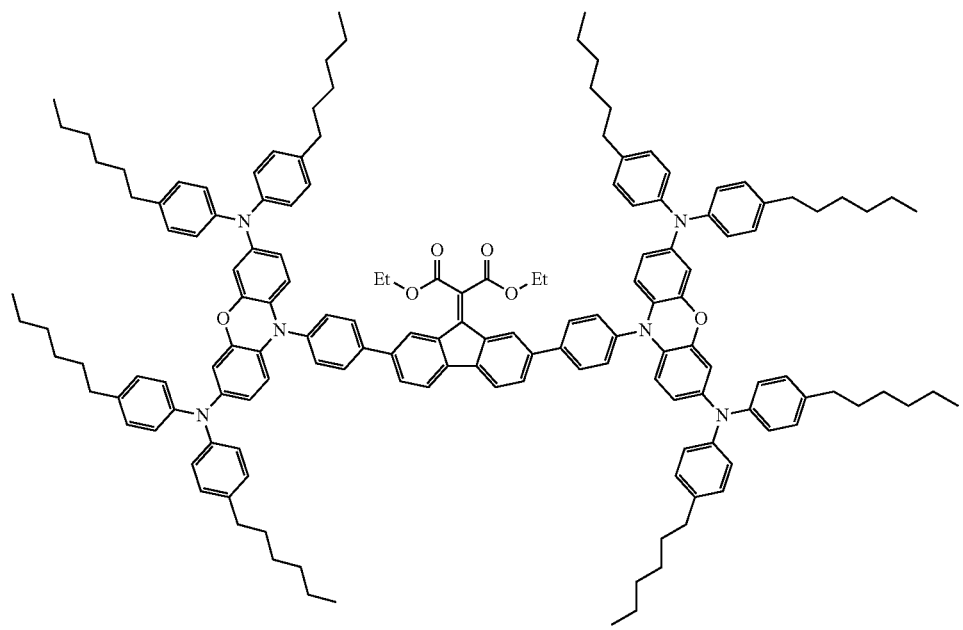
(A-151)
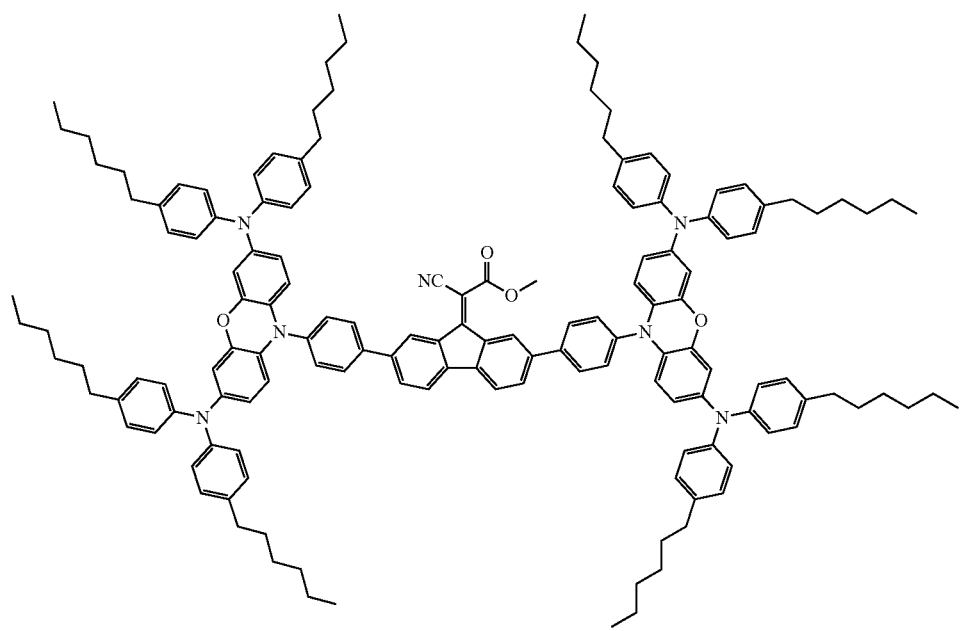

-continued
(A-152)
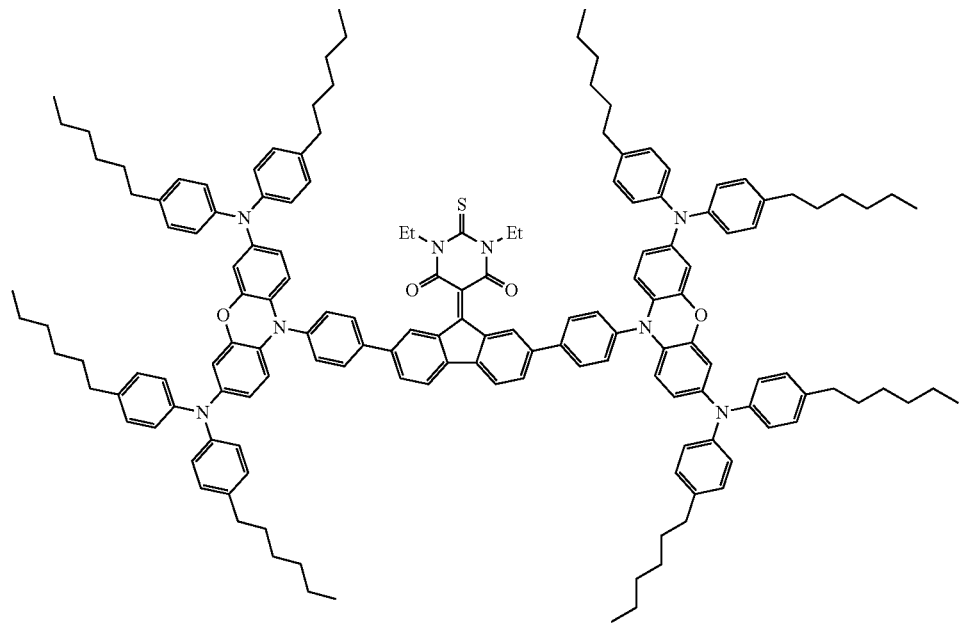
[Chem. 17]
(A-153)
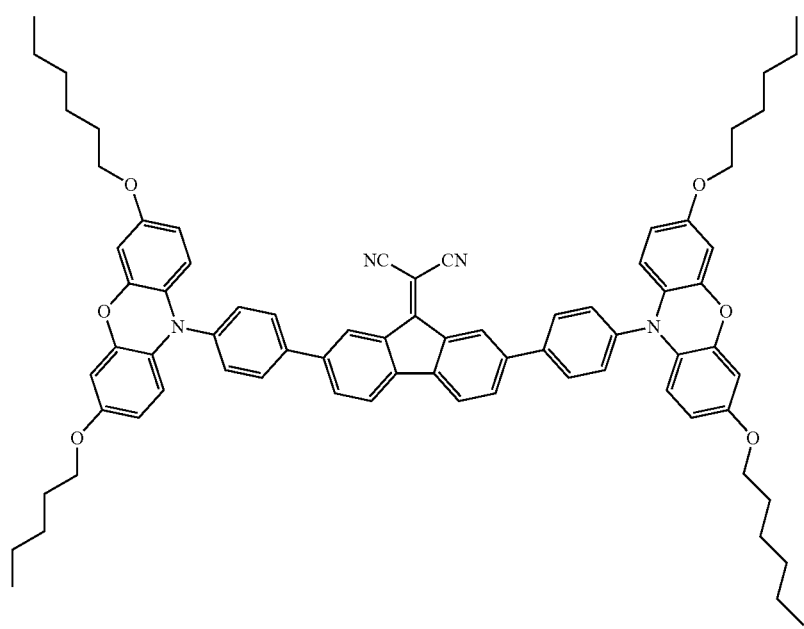

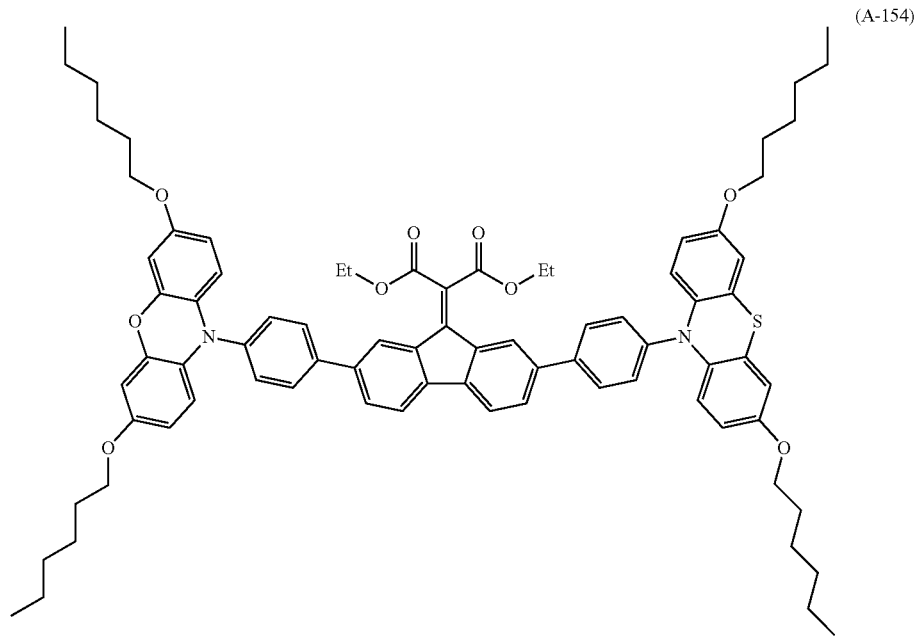
(A-154)
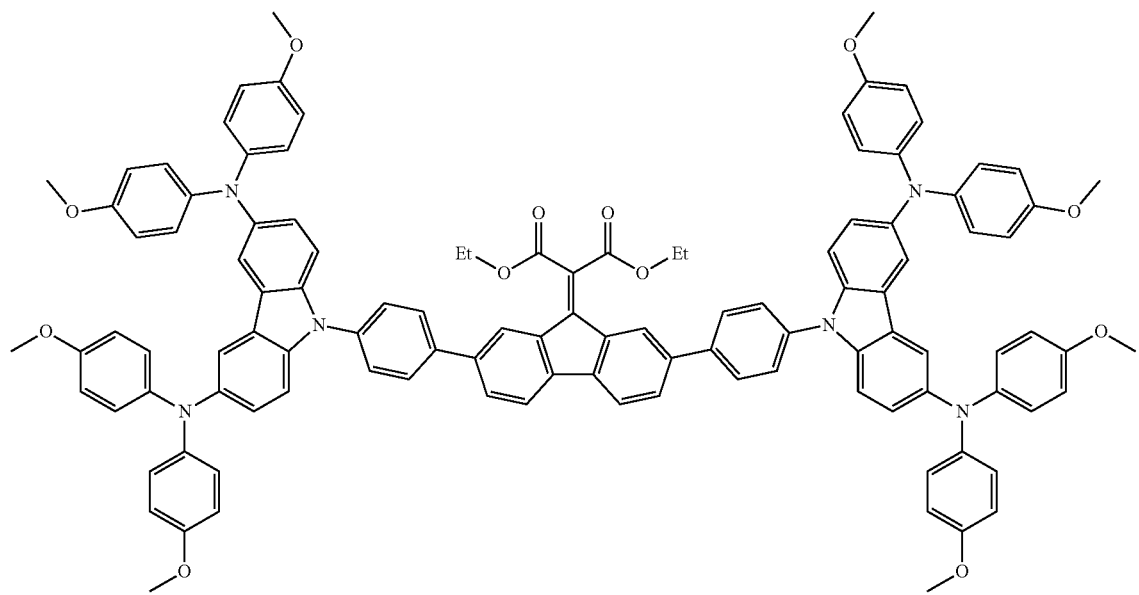
(A-155)

-continued
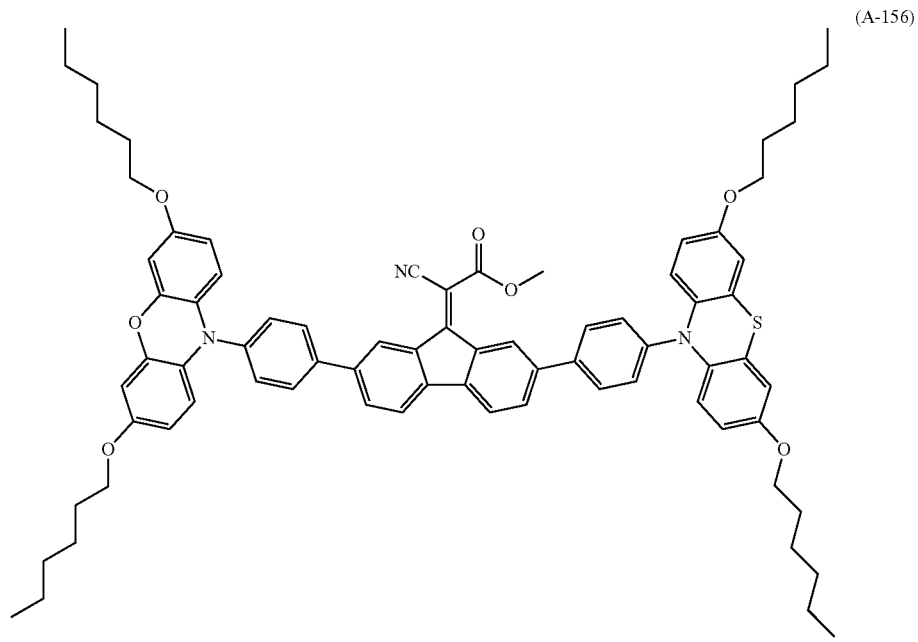 [SMILES: CCCCCCOc1ccc2c(c1)Oc1cc(OCCCCCC)ccc1N2c1ccc(-c2ccc3c(c2)/C(=C(\C#N)C(=O)OC)c2cc(-c4ccc(N5c6ccc(OCCCCCC)cc6Sc6cc(OCCCCCC)ccc65)cc4)ccc2-3)cc1]
(A-156)
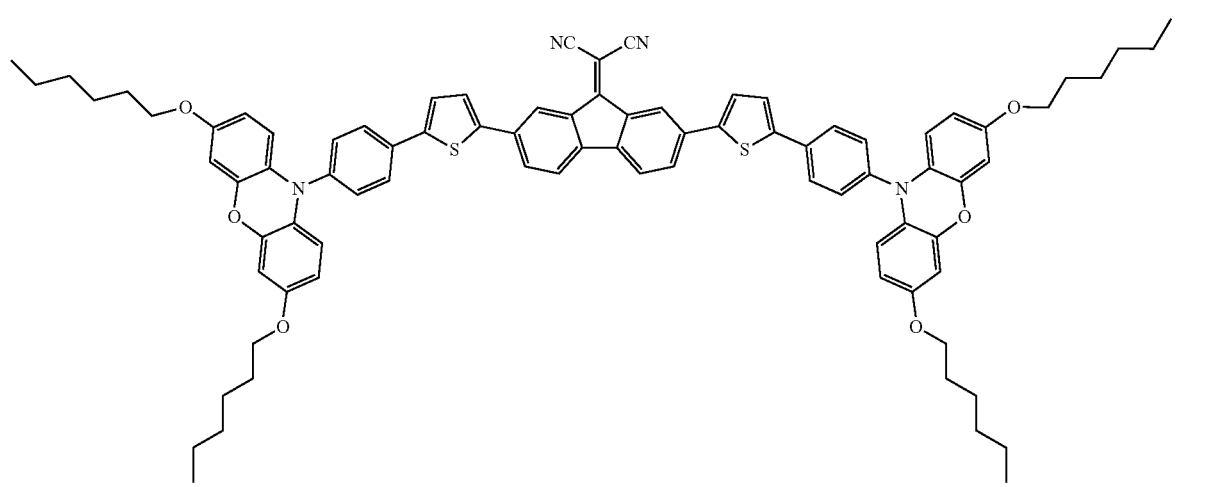
(A-157)
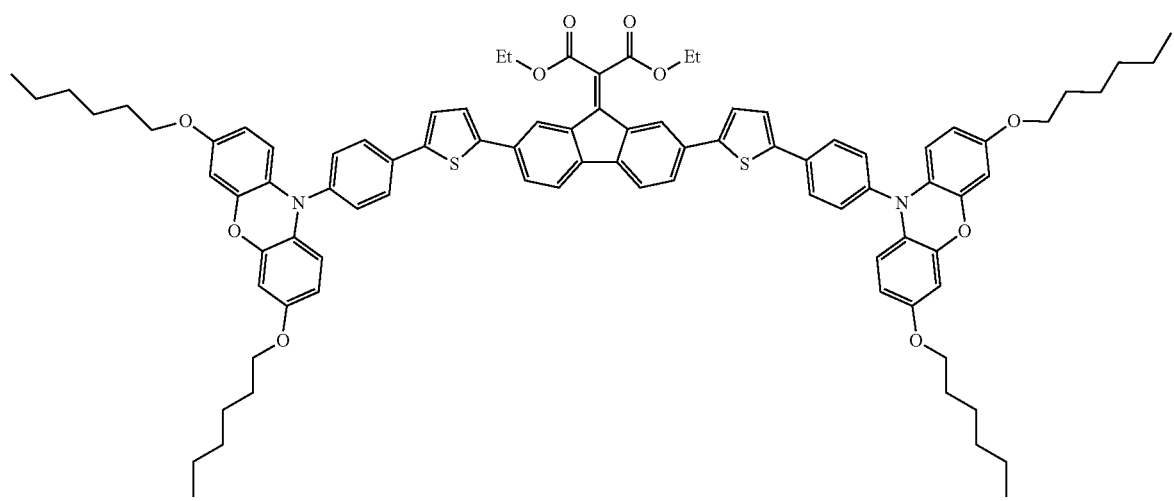
(A-158)

The compound represented by the general formula (1) can be synthesized using a known method.

For example, the compound can be synthesized by performing a Suzuki-Miyaura cross-coupling reaction between 2,7-dibromofluorenone represented by the formula (3) below and boronic acid compounds represented by the general formulae (4) and (5) below or boronate ester compounds represented by the general formulae (6) and (7) below and subjecting the reaction product to a Knoevenagel condensation reaction with a compound represented by the general formula (8) below.

[Chem. 18]

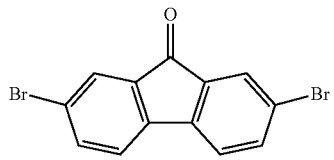

(3)

[Chem. 19]

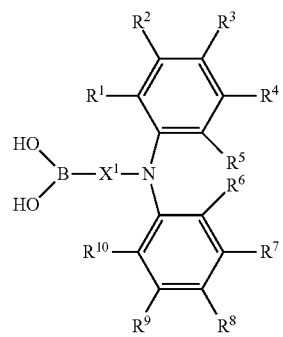

(4)

[Chem. 20]

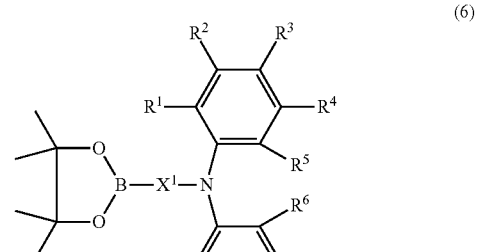

(6)

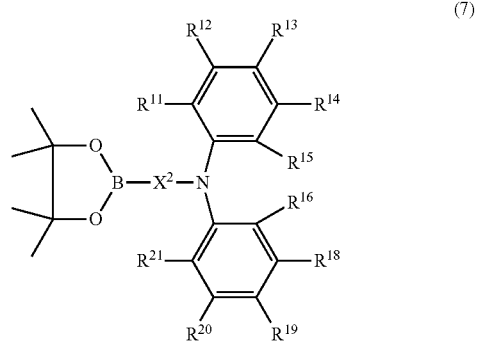

(7)

The symbols in the formulae are as defined in the general formula (1).

[Chem. 21]

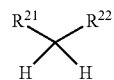

(8)

The symbols in the formulae are as defined in the general formula (1).

The compound represented by the general formula (1) may be purified by, for example, column chromatography; adsorption with silica gel, activated carbon, activated clay, or the like; or recrystallization or crystallization from a solvent. It is also effective to use a compound with higher purity obtained by performing these methods in combination. The compound can be identified through nuclear magnetic resonance (NMR) spectroscopy.

Hereinafter, a preferred mode of the device for converting light into electricity of the present invention will be described.

As shown in FIG. 1, the device of the present invention preferably includes, without limitation, the conductive support 1, the electron transport layer 2, the light/electricity conversion layer 3, the hole transport layer 4, and the counter electrode 5. Also, the device of the present invention can be suitably used as a solar cell, and is more preferably, but not limited to, a perovskite device for converting light into electricity. In the present invention, the perovskite device for converting light into electricity preferably includes a conductive support (electrode) 1, an electron

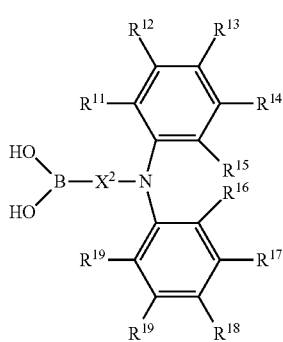

(5)

transport layer 2, a light/electricity conversion layer (perovskite layer) 3, a hole transport layer 4, and a counter electrode 5 in this order. Alternatively, the perovskite device may include a conductive support, a hole transport layer, a light/electricity conversion layer (perovskite layer), an electron transport layer, and a counter electrode in this order.

Conductive Support

In the device of the present invention, the conductive support 1 shown in FIG. 1 needs to have optical transparency so as to transmit light that contributes to light/electricity conversion. In addition, the conductive support is a member configured to extract current from the light/electricity conversion layer, and accordingly, is preferably a conductive substrate. Specific examples of conductive materials include conductive transparent oxide semiconductors such as tin-doped indium oxide (ITO), zinc-doped indium oxide (IZO), tungsten-doped indium oxide (IWO), aluminum zinc oxide (AZO), fluorine-doped tin oxide (FTO), indium oxide ($In_2O_3$), and indium-tin complex oxides, and it is preferable to use tin-doped indium oxide (ITO) or fluorine-doped tin oxide (FTO).

Electron Transport Layer

In the device of the present invention, the electron transport layer 2 shown in FIG. 1 is positioned between the conductive support 1 described above and the light/electricity conversion layer (perovskite layer) 3. The electron transport layer 2 is preferably formed on the conductive support 1, but the position is not limited thereto. The electron transport layer is used to improve the efficiency in transfer of electrons from the light/electricity conversion layer to the electrode and also used to block the transfer of holes.

Examples of a semiconductor for forming the electron transport layer include: metal oxides such as tin oxide (SnO, $SnO_2$, $SnO_3$, etc.), titanium oxide ($TiO_2$ etc.), tungsten oxide ($WO_2$, $WO_3$, $W_2O_3$, etc.), zinc oxide (ZnO), niobium oxides ($Nb_2O_5$ etc.), tantalum oxide ($Ta_2O_5$ etc.), yttrium oxide ($Y_2O_3$ etc.), and strontium titanate ($SrTiO_3$ etc.); metal sulfides such as titanium sulfide, zinc sulfide, zirconium sulfide, copper sulfide, tin sulfide, indium sulfide, tungsten sulfide, cadmium sulfide, and silver sulfide; metal selenides such as titanium selenide, zirconium selenide, indium selenide, and tungsten selenide; and elemental semiconductors such as silicon and germanium. These semiconductors may also be used in combinations of two or more. In the present invention, it is preferable to use one or more selected from tin oxide, titanium oxide, and zinc oxide as the semiconductor.

The electron transport layer may be formed by using a commercially available paste containing microparticles of the above-described semiconductor (coating solution for an electron transport layer), or a paste or the like prepared by dispersing a commercially available semiconductor fine powder in a solvent. Specific examples of the solvent used to prepare the paste include, but are not limited to, water; alcoholic solvents such as methanol, ethanol, and isopropyl alcohol; ketone solvents such as acetone, methyl ethyl ketone, and methyl isobutyl ketone; and hydrocarbon solvents such as n-hexane, cyclohexane, benzene, and toluene. These solvents may also be used in a combination of two or more as a solvent mixture.

For dispersing the semiconductor fine powder in the solvent, a disperser may be used, including a ball mill, a paint conditioner, a vertical bead mill, a horizontal bead mill, and an attritor, and the powder may be ground in a mortar or the like before use. In preparing a paste, a surfactant or the like is preferably added to prevent aggregation of semiconductor fine particles, and a thickening agent such as polyethylene glycol is preferably added to impart viscosity.

The electron transport layer can be formed using a known film formation method depending on the material used. Examples of the method for forming the electron transport layer include, but are not limited to, a method including forming a coating film on a conductive substrate using a wet coating method, and then removing the solvent and additives therefrom through firing, and examples of the wet coating method include spin coating, inkjet coating, doctor blade coating, drop casting, squeegee coating, screen printing, reverse roll coating, gravure coating, kiss coating, roll brushing, spray coating, air knife coating, wire-bar bar coating, pipe doctor coating, impregnation and coating, and curtain coating. Other examples of the method for forming the electron transport layer include a method including forming a film by sputtering, evaporation, electrodeposition, electrocrystallization, or microwave irradiation. In the present invention, it is preferable to form the electron transport layer by spin coating using a coating solution for the electron transport layer that has been prepared in the above-described manner, but the method for forming the electron transport layer is not limited to this. The conditions for spin coating can be set as appropriate. There is no particular limitation on the atmosphere in which the electron transport layer is formed, and the electron transport layer may be formed in normal air.

When a dense electron transport layer is to be used in view of further improving the power conversion efficiency, the film thickness of the electron transport layer is usually preferably 5 to 100 nm, and more preferably 10 to 50 nm. In the present invention, when a porous (mesoporous) metal oxide is used in addition to the dense layer, the film thickness is usually preferably 20 to 200 nm, and more preferably 50 to 150 nm.

Layer that Convers Light into Electricity
(Light/Electricity Conversion Layer)

In the device of the present invention, the light/electricity conversion layer (perovskite layer) 3 is preferably formed on the electron transport layer 2 as shown in FIG. 1.

When the device of the present invention is a perovskite device for converting light into electricity, examples of a perovskite material used in the light/electricity conversion layer include materials of a family having a structure represented by the general formula $ABX_3$, where A, B, and X represent an organic cation or a monovalent metal cation, a metal cation, and a halide anion, respectively. For example, combinations of A=$K^+$, $Rb^+$, $Cs^+$, $CH_3NH_3^+$ (hereinafter referred to as "MA" (methylammonium)), $NH=CHNH_2^+$ (hereinafter referred to as "FA" (formamidinium)), or $CH_3CH_2NH_3^+$ (hereinafter referred to as "EA" (ethylammonium)); B=$Pb^{2+}$ or $Sn^{2+}$; and X=$I^-$ or $Br^-$ are conceivable. More specific examples include, but are not limited to, perovskite materials represented by the compositions $MAPbI_3$, $FAPbI_3$, $EAPbI_3$, $CsPbI_3$, $MASnI_3$, $FASnI_3$, $EASnI_3$, $MAPbBr_3$, $FAPbBr_3$, $EAPbBr_3$, $MASnBr_3$, $FASnBr_3$, and $EASnBr_3$, and also perovskite materials composed of mixed cations and mixed anions represented by the compositions $K(FAMA)Pb(IBr)_3$, $Rb(FAMA)Pb(IBr)_3$, and $Cs(FAMA)Pb(IBr)_3$. These perovskite materials may also be used in a combination of two or more. The light/electricity conversion layer may contain a light absorbing agent other than a perovskite material.

The light/electricity conversion layer (perovskite layer) of the device of the present invention may be formed by any coating method involving use of a coating solution, and examples of the method include those described above as the method for forming the electron transport layer. The perovskite layer can be produced by forming a coating film by using a perovskite material precursor solution and then heating the coating film.

A commercially available perovskite precursor may be used, and in the present invention, a precursor obtained by mixing a lead halide, a methylammonium halide, a formamidine halide, and a cesium halide to achieve a desired composition is preferably used, but the perovskite precursor is not limited to this.

Examples of a solvent for the perovskite precursor solution include, but are not limited to, N,N-dimethylformamide (DMF), dimethyl sulfoxide (DMSO), and γ-butyrolactone, in view of the solubility of the precursor. These solvents may also be used in a combination of two or more, and a solvent mixture of N,N-dimethylformamide and dimethyl sulfoxide is preferably used.

The atmosphere in which the light/electricity conversion layer (perovskite layer) is formed is preferably a dry atmosphere, which prevents moisture contamination to thereby enable a highly efficient device for converting light into electricity to be produced with high reproducibility, and more preferably a dry inert gas atmosphere in a glove box or the like. It is also preferable to use a solvent with low moisture content obtained by drying with a molecular sieve.

The temperature at which the light/electricity conversion layer (perovskite layer) is heated using a hot plate or other means is preferably 50 to 200° C., and more preferably 70 to 150° C., in view of efficiently producing the perovskite material from the precursor. The heating time is preferably 10 to 90 minutes, and more preferably 10 to 60 minutes.

The film thickness of the light/electricity conversion layer (perovskite layer) is preferably 50 to 1000 nm, and more preferably 300 to 700 nm, in view of more reliably suppressing degradation in performance due to a defect or delamination and also ensuring a sufficient light absorptance of the light/electricity conversion layer and not too much resistance of the device.

Hole Transport Layer

In the device of the present invention, the hole transport layer 4 shown in FIG. 1 is a layer that transports holes and is positioned between the light/electricity conversion layer (perovskite layer) 3 and the counter electrode 5. The hole transport layer is used to improve the efficiency in the transfer of holes from the light/electricity conversion layer to the electrode and also used to block the transfer of electrons. For the hole transport layer, conductors, semiconductors, organic hole transport materials, and the like can be used, and an additive may also be contained for the purpose of further improving the hole transporting properties.

The hole transport layer in the device of the present invention is a layer that contains the compound represented by the general formula (1) as a hole transport material. For the hole transport layer, two or more compounds represented by the general formula (1) may be used in combination. The compound represented by the general formula (1) may also be used in combination with another hole transport material or the like that is outside the scope of the present invention.

Specific examples of the other hole transport material that is outside the scope of the hole transport material of the present invention include compound semiconductors containing monovalent copper, such as CuI, $CuInSe_2$, and CuS; and also compounds containing a metal other than copper, such as GaP, NiO, CoO, FeO, $Bi_2O_3$, $MoO_2$, and $Cr_2O_3$. These oxide metals may be incorporated into the hole transport layer or may be laminated on the hole transport material. Examples of the organic hole transport materials include polythiophene derivatives such as poly-3-hexylthiophene (P3HT) and polyethylenedioxythiophene (PEDOT); fluorene derivatives such as 2,2',7,7'-tetrakis-(N,N-di-p-methoxyphenylamine)-9,9'-spirobifluorene (Spiro-OMeTAD); carbazole derivatives such as polyvinylcarbazole; triphenylamine derivatives such as poly[bis(4-phenyl) (2,4,6-trimethylphenyl)amine] (PTAA); diphenylamine derivatives; polysilane derivatives; and polyaniline derivatives.

The hole transport layer of the device of the present invention may be formed by any coating method involving use of a coating solution, and examples thereof include those described above as the method for forming the electron transport layer.

Examples of a solvent used in the coating solution for the hole transport layer include, but are not limited to, aromatic organic solvents such as benzene, toluene, xylene, mesitylene, tetralin (1,2,3,4-tetrahydronaphthalene), monochlorobenzene (chlorobenzene), o-dichlorobenzene, m-dichlorobenzene, p-dichlorobenzene, and nitrobenzene; alkyl halide organic solvents such as dichloromethane, chloroform, 1,2-dichloroethane, 1,1,2-trichloroethane, and dichloromethane; nitrile solvents such as benzonitrile and acetonitrile; ether solvents such as tetrahydrofuran, dioxane, diisopropyl ether, c-pentyl methyl ether, ethylene glycol dimethyl ether, ethylene glycol diethyl ether, and propylene glycol monomethyl ether; ester solvents such as ethyl acetate and propylene glycol monomethyl ether acetate; alcoholic solvents such as methanol, isopropanol, n-butanol, propylene glycol, 1,3-butanediol, 1,4-butanediol, 2,3-butanediol, cyclohexanol, and 2-n-butoxyethanol. These solvents may also be used in a combination of two or more thereof, and the solvent used can be selected according to the hole transport material used. In particular, aromatic organic solvents and alkyl halide organic solvents are preferable.

In the device of the present invention, the film thickness of the hole transport layer is preferably 5 to 500 nm, and more preferably 10 to 250 nm, in view of further improving the power conversion efficiency.

The atmosphere in which the hole transport layer is formed is preferably a dry atmosphere, which prevents moisture contamination to thereby enable a highly efficient device for converting light into electricity to be produced with high reproducibility. It is also preferable to use a dried solvent with a moisture content of 10 ppm or less.

Additives

The device of the present invention may contain a dopant (or an oxidizing agent) or a basic compound (or a basic additive) as an additive in the hole transport layer. Incorporating the additive into the hole transport layer to increase the carrier concentration of the hole transport material in the hole transport layer (i.e., doping) leads to an improvement in the conversion efficiency of the device. In the present invention, when the hole transport layer contains a dopant and a basic additive as additives, the amount of the additives is preferably 3.5 equivalents or less per 1 equivalent of the hole transport material.

For the case where the hole transport layer contains the dopant, specific examples of the dopant include lithium bis(trifluoromethylsulfonyl)imide (LiTFSI), silver bis(trifluoromethanesulfonyl)imide, tris(2-(1H-pyrazol-1-yl)-4-tert-butylpyridine)cobalt(III) tri[bis(trifluoromethane)sulfonimide] (FK209), $NOSbF_6$, $SbCl_5$, and $SbF_5$. In the present invention, lithium bis(trifluoromethylsulfonyl)imide (LiTFSI) is preferably used, but the dopant used is not limited to this.

When a dopant is used, the amount of the dopant is preferably 2.0 equivalents or less, and more preferably 0.5 equivalents or less, per 1 equivalent of the hole transport material contained in the hole transport layer.

For the case where the hole transport layer contains the basic compound, specific examples thereof include 4-tert-butylpyridine (tBP), 2-picoline, and 2,6-lutidine. When the above-described dopant is used, the basic compound is often used in combination with the dopant. In the present invention as well, when the dopant is used, it is desirable to use the basic compound along with the dopant, and 4-tert-butylpyridine is preferably used.

When the basic compound is used, the amount of the basic compound is preferably 5 equivalents or less, and more preferably 3 equivalents or less, per 1 equivalent of the hole transport material contained in the hole transport layer.

Counter Electrode

In the device of the present invention, the counter electrode 5 shown in FIG. 1 is a layer that is disposed opposite the conductive support 1 and formed on the hole transport layer 4, and the counter electrode 5 is used to exchange charges with the hole transport layer. In the device of the present invention, a metal electrode serving as the counter electrode is provided preferably on the hole transport layer 4. An electron blocking layer made of an organic material or an inorganic compound semiconductor may be interposed between the hole transport layer 4 and the counter electrode 5.

Specific examples of a material used for the counter electrode include metals such as platinum, titanium, stainless steel, aluminum, gold, silver, nickel, magnesium, chromium, cobalt, and copper, and also alloys of these metals. Among these, gold, silver, or a silver alloy is preferably used in view of high electrical conductivity even in the form of a thin film. As the silver alloy, it is preferable to use a silver-gold alloy, a silver-copper alloy, a silver-palladium alloy, a silver-copper-palladium alloy, a silver-platinum alloy, and the like, which are less susceptible to sulfidation and chlorination and thus increase the stability of the thin film.

The material for forming the counter electrode is preferably such that the counter electrode can be formed by using the material by evaporation or the like.

When a metal electrode is used as the counter electrode, the film thickness of the metal electrode is preferably 10 nm or greater, and more preferably 50 nm or greater, in view of obtaining favorable conductivity.

In the device of the present invention, the conductive support serves as a negative electrode, and the counter electrode serves as a positive electrode. The conductive support side of the device is preferably irradiated with light such as sunlight. When irradiated with sunlight or the like, the light/electricity conversion layer (perovskite layer) absorbs light and becomes excited, generating electrons and holes. The electrons move through the electron transport layer, and the holes move through the hole transport layer, to reach the respective electrodes, thereby causing a current to flow, and thus, the device for converting light into electricity performs its function.

For the device of the present invention, the short-circuit current density, open-circuit voltage, fill factor, and power conversion efficiency may be determined to evaluate the performance (characteristics) of the device. The short-circuit current density refers to the current per 1 $cm^2$ that flows between two terminals when the output terminal is short-circuited, and the open-circuit voltage refers to the voltage between the two terminals when the output terminal is open-circuited. The fill factor is a value obtained by dividing the maximum output (product of current and voltage) by the product of short-circuit current density and open-circuit voltage, and mainly depends on the internal resistance. The power conversion efficiency is a numerical value in percent obtained by dividing the maximum output (W) by the light intensity (W) per 1 $cm^2$ and multiplying the quotient by 100.

The device of the present invention can be applied to perovskite solar cells, various optical sensors, and the like. In a perovskite solar cell module, the device of the present invention, which includes the hole transport material containing the compound represented by the general formula (1) as the hole transport layer, serves as a cell. The required number of such cells are arranged to form the solar cell module, to which predetermined electrical wiring is provided.

Although preferred embodiments has been described above, the present invention is not limited thereto, and changes and modifications may be made thereto as appropriate without departing from the scope of the present invention.

EXAMPLES

Hereinafter, the present invention will be described in greater detail by way of Examples with reference to the drawings, but the present invention is not limited to the following Examples. In Synthesis Examples below, the compounds obtained were identified using $^1$H-NMR (a nuclear magnetic resonance spectrometer, model JNM-ECZ400S/L1, manufactured by JEOL Ltd.).

Synthesis Example 1: Synthesis of Compound (A-2)

First, 2,7-dibromofluorenone (0.63 g, manufactured by Tokyo Chemical Industry Co., Ltd. (TCI)), [4-[bis(4-methoxyphenyl)amino]phenyl]boronic acid (1.50 g, manufactured by TCI), tetrakis(triphenylphosphine)palladium(0) (0.09 g, manufactured by Kanto Chemical Co., Inc.), potassium carbonate (0.68 g, manufactured by Kanto Chemical Co., Inc.), toluene (10 mL), ethanol (3.5 mL), and water (3.5 mL) were placed in a reaction vessel and degassed under reduced pressure. The mixture was stirred in an argon atmosphere while heating under reflux for 6 hours. After the reaction was completed, toluene (10 mL) and water (20 mL) were added. The resulting mixture was subjected to liquid-liquid separation, and the organic layer was washed with water (30 mL) twice. The organic layer was concentrated, and the resulting crude product was purified using a silica gel column (toluene) to obtain a compound represented by the formula (A-2) below, as a reddish purple powder (actual yield: 1.44 g, percent yield: 98%).

$^1$H-NMR (400 MHz, $CDCl_3$): δ (ppm)=3.81 (12H), 6.85 (8H), 6.98 (4H), 7.10 (8H), 7.43 (4H), 7.53 (2H), 7.67 (2H), 7.86 (2H).

[Chem. 22]

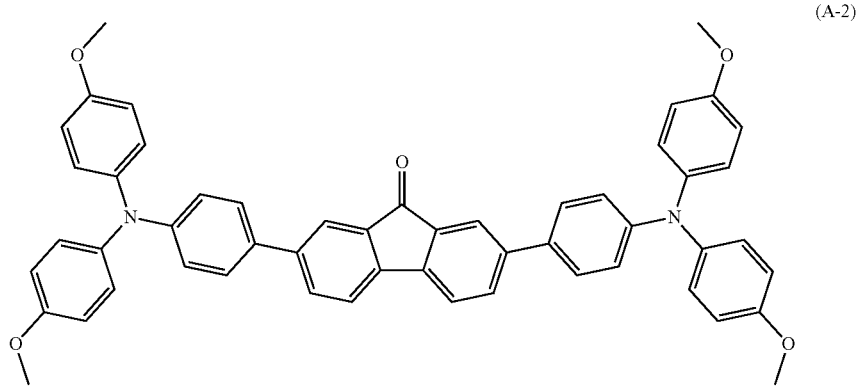

(A-2)

Synthesis Example 2: Synthesis of Compound (A-15)

The compound of the above formula (A-2) (0.60 g), malononitrile (0.20 g, manufactured by Tokyo Chemical Industry Co., Ltd.), and 25 mL of THF were placed in a reaction vessel and stirred in an argon atmosphere. Acetic acid (2.4 mL, manufactured by Kanto Chemical Co., Inc.) and pyridine (2.4 mL, manufactured by Nacalai Tesque, Inc.) were added thereto, and the mixture was stirred while heating under reflux for 16 hours. After the reaction was completed, the reaction solution was put into a beaker containing 300 mL of water. The resulting mixture was filtered, and the residue on the filter was washed with 30 mL of water and with 20 mL of methanol. The resulting crude product was purified using a silica gel column (toluene:chloroform=4:1) to obtain a compound represented by the formula (A-15) below, as a black green powder (actual yield: 0.54 g, percent yield: 84%).

$^1$H-NMR (400 MHz, CDCl$_3$): δ (ppm)=3.81 (12H), 6.86 (8H), 6.98 (4H), 7.10 (8H), 7.43 (4H), 7.53 (2H), 7.65 (2H), 8.57 (2H).

Synthesis Example 3: Synthesis of Compound (A-28)

The compound of the above formula (A-2) (0.6 g), diethyl malonate (0.37 g, manufactured by Tokyo Chemical Industry Co., Ltd.), and THF (14 mL) were placed in a reaction vessel and stirred in an argon atmosphere. The mixture was cooled to 5° C. or below in an ice bath, and pyridine (1 mL) was added. The mixture was cooled again to 5° C. or below, and titanium tetrachloride (0.5 mL, manufactured by Wako Pure Chemical Industries, Ltd.) was added. The temperature was then raised to room temperature, and the mixture was stirred at room temperature for 17 hours. After the reaction was completed, the reaction solution was poured into a beaker containing 200 mL of water, and toluene (30 mL) was added thereto. The resulting mixture was subjected to liquid-liquid separation, and the organic layer was dried over magnesium sulfate and then concentrated. The resulting crude product was purified using a silica gel column (toluene) to obtain a compound represented by the formula (A-28) below, as a reddish purple powder (actual yield: 0.50 g, percent yield: 71%).

$^1$H-NMR (400 MHz, CDCl$_3$): δ (ppm)=1.37 (6H), 3.81 (12H), 4.43 (4H), 6.86 (8H), 6.99 (4H), 7.11 (8H), 7.40 (4H), 7.56 (2H), 7.60 (2H), 8.04 (2H).

[Chem. 23]

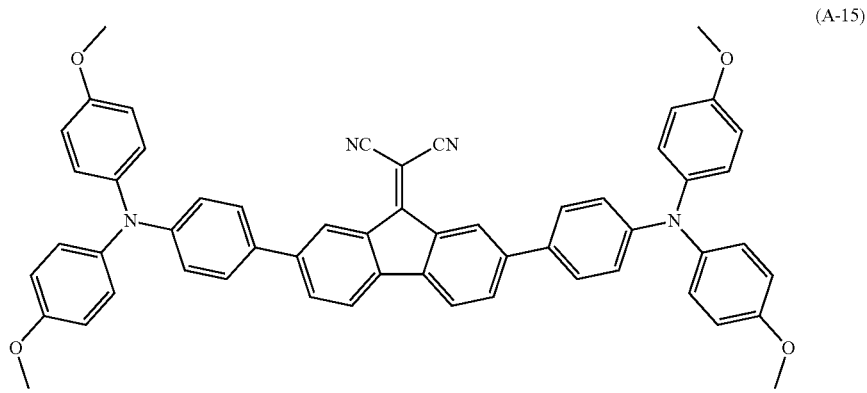

(A-15)

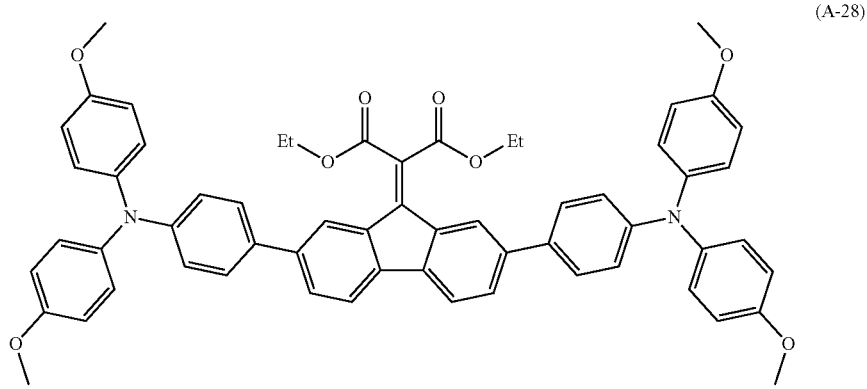

(A-28)

Synthesis Example 4: Synthesis of Compound (A-41)

The compound of the above formula (A-2) (0.65 g), methyl cyanoacetate (0.33 g, manufactured by Tokyo Chemical Industry Co., Ltd.), and THF (25 mL) were placed in a reaction vessel and stirred in an argon atmosphere. The mixture was cooled to 5° C. or below in an ice bath, and pyridine (1 mL) was added. The mixture was cooled again to 5° C. or below, and titanium tetrachloride (0.55 mL, manufactured by Wako Pure Chemical Industries, Ltd.) was added. The temperature was then raised to room temperature, and the mixture was stirred at room temperature for 8 hours, and then stirred for 2 hours while heating under reflux. After the reaction was completed, the reaction solution was poured into a beaker containing water (200 mL), and toluene (30 mL) was added thereto. The resulting mixture was subjected to liquid-liquid separation, and the organic layer was dried over magnesium sulfate and then concentrated. The resulting crude product was purified using a silica gel column (toluene) to obtain a compound represented by the formula (A-41) below, as a black green powder (actual yield: 0.65 g, percent yield: 90%).

$^1$H-NMR (400 MHz, CDCl$_3$): δ (ppm)=3.81 (12H), 4.10 (3H), 6.86 (8H), 6.99 (4H), 7.11 (8H), 7.40 (2H), 7.46 (2H), 7.50 (2H), 7.60 (2H), 8.26 (1H), 8.78 (1H).

Synthesis Example 5: Synthesis of Compound (A-1)

First, 2,7-dibromofluorenone (0.75 g, manufactured by Tokyo Chemical Industry Co., Ltd.), 4-(diphenylamino) phenylboronic acid (1.48 g, manufactured by Sigma-Aldrich), tetrakis(triphenylphosphine)palladium(0) (0.10 g, manufactured by Kanto Chemical Co., Inc.), potassium carbonate (0.80 g, manufactured by Kanto Chemical Co., Inc.), toluene (12 mL), ethanol (4.0 mL), and water (4.0 mL) were placed in a reaction vessel and degassed under reduced pressure. The mixture was stirred in an argon atmosphere while heating under reflux for 4 hours. After the reaction was completed, the reaction solution was put into a beaker containing water (100 mL), and 30 mL of toluene was added thereto. The resulting mixture was subjected to liquid-liquid separation, and the organic layer was dried over magnesium sulfate and then concentrated. The resulting crude product was purified using a silica gel column (toluene), followed by recrystallization from toluene, to obtain a compound represented by the formula (A-1) below, as a red powder (actual yield: 1.48 g, percent yield: 100%).

$^1$H-NMR (400 MHz, DMSO-d$_6$): δ (ppm)=7.0-7.1 (16H), 7.35 (8H), 7.71 (4H), 7.85 (2H), 7.92 (4H).

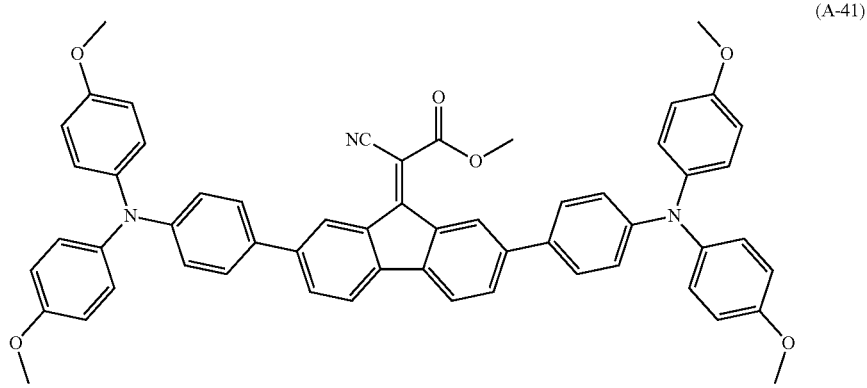

(A-41)

[Chem. 26]

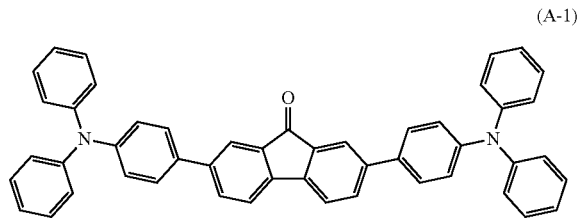

(A-1)

Synthesis Example 6: Synthesis of Compound (A-27)

The compound of the above formula (A-1) (0.6 g), diethyl malonate (0.82 g, manufactured by TCI), and THF (27 mL) were placed in a reaction vessel and stirred in an argon atmosphere. The mixture was cooled to 5° C. or below in an ice bath, and pyridine (1.1 mL) was added. The mixture was cooled again to 5° C. or below, and titanium tetrachloride (0.6 mL, manufactured by Wako Pure Chemical Industries, Ltd.) was added. The temperature was then raised to room temperature, and the mixture was stirred at room temperature for 17 hours. After the reaction was completed, the reaction solution was poured into a beaker containing 200 mL of water, and toluene (30 mL) was added thereto. The resulting mixture was subjected to liquid-liquid separation, and the organic layer was dried over magnesium sulfate and then concentrated. The resulting crude product was purified using a silica gel column (toluene) to obtain a compound represented by the formula (A-27) below, as a red powder (actual yield: 0.52 g, percent yield: 71%).

$^1$H-NMR (400 MHz, DMSO-d$_6$): δ (ppm)=1.38 (6H), 4.45 (4H), 7.06 (4H), 7.13-7.16 (12H), 7.29 (8H), 7.46 (4H), 7.61 (4H), 7.07 (2H).

[Chem. 27]

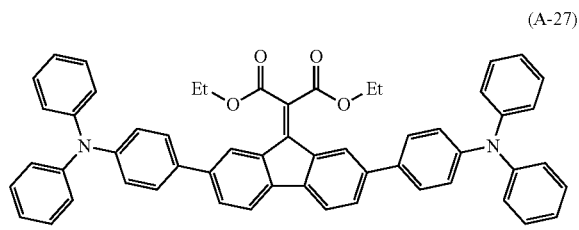

(A-27)

Synthesis Example 7: Synthesis of Compound (A-14)

The compound of the above formula (A-1) (0.60 g), malononitrile (0.23 g, manufactured by Tokyo Chemical Industry Co., Ltd.), and THF (50 mL) were placed in a reaction vessel and stirred in an argon atmosphere. Acetic acid (2.8 mL, manufactured by Kanto Chemical Co., Inc.) and pyridine (2.8 mL, manufactured by Nacalai Tesque, Inc.) were added thereto, and the mixture was stirred for 6 hours while heating under reflux. After the reaction was completed, the reaction solution was put into a beaker containing water (200 mL). The resulting mixture was filtered, and the residue on the filter was washed with water (20 mL) and with methanol (20 mL). The resulting crude product was recrystallized (chloroform) to obtain a compound represented by the formula (A-14) below, as a black green powder (actual yield: 0.58 g, percent yield: 91%).

$^1$H-NMR (400 MHz, THF-d$_8$): δ (ppm)=7.0-7.1 (16H), 7.35 (8H), 7.71 (4H), 7.92 (4H), 8.56 (2H).

[Chem. 28]

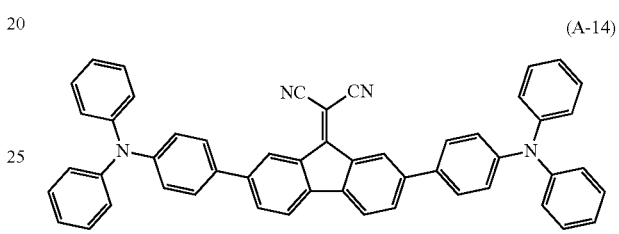

(A-14)

Synthesis Example 8: Synthesis of Compound (A-67)

First, 2,7-dibromofluorenone (0.47 g, manufactured by Tokyo Chemical Industry Co., Ltd.), the compound of the formula (9) below (2.71 g), tetrakis(triphenylphosphine) palladium(0) (0.065 g, manufactured by Kanto Chemical Co., Inc.), potassium carbonate (0.51 g, manufactured by Kanto Chemical Co., Inc.), toluene (7.5 mL), ethanol (2.5 mL), and water (2.5 mL) were placed in a reaction vessel and degassed under reduced pressure. The mixture was stirred in an argon atmosphere for 13 hours while heating under reflux. After the reaction was completed, toluene (20 mL) and water (10 mL) were added. The resulting mixture was subjected to liquid-liquid separation. The aqueous layer was washed with toluene (20 mL) twice, and the organic layer was concentrated. The resulting crude product was purified using a silica gel column (toluene/ethyl acetate=50/1 (volume ratio)) to obtain a compound represented by the formula (A-67) below, as a red powder (actual yield: 1.76 g, percent yield: 80%).

$^1$H-NMR (400 MHz, DMSO-d$_6$): δ (ppm)=3.65 (24H), 6.75 (16H), 6.83 (16H), 7.02 (4H), 7.19 (4H), 7.58 (4H), 7.63 (4H), 7.88 (4H), 7.95 (6H).

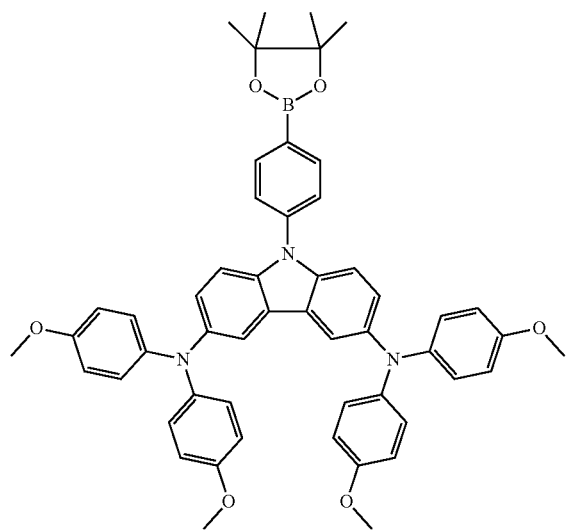

(9)

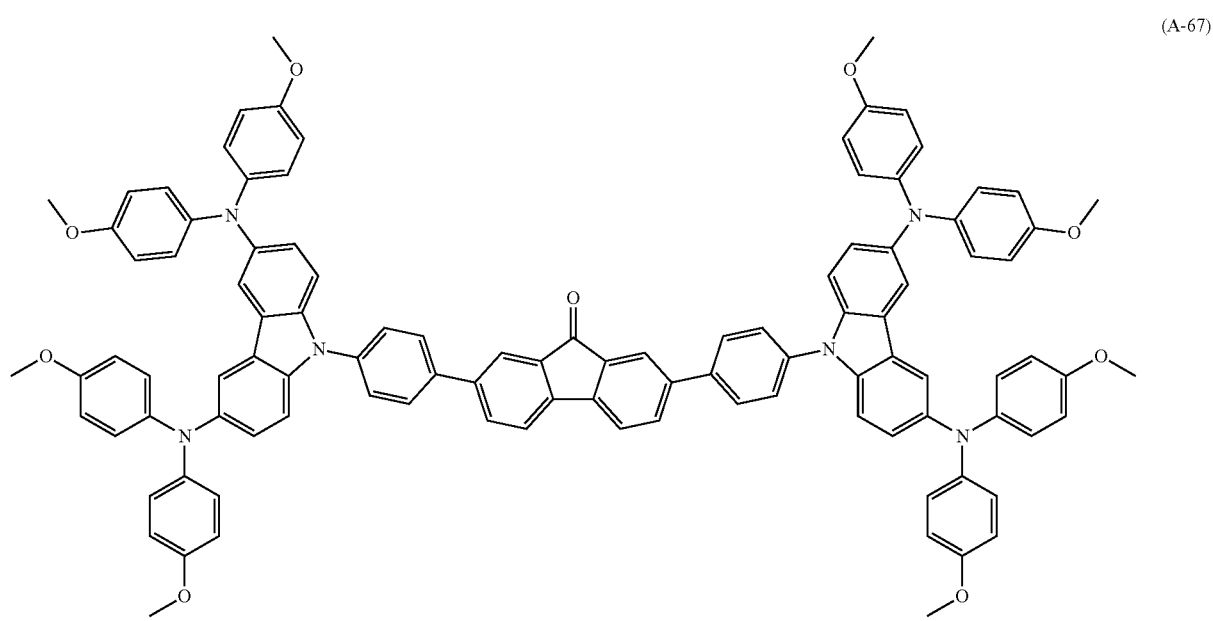

(A-67)

Synthesis Example 9: Synthesis of Compound (A-82)

The compound of the above formula (A-67) (0.70 g), malononitrile (0.12 g, manufactured by Tokyo Chemical Industry Co., Ltd.), and THF (18 mL) were placed in a reaction vessel and stirred in an argon atmosphere. Acetic acid (1.6 mL, manufactured by Kanto Chemical Co., Inc.) and pyridine (1.6 mL, manufactured by Nacalai Tesque, Inc.) were added thereto, and the mixture was stirred for 14 hours while heating under reflux. After the reaction was completed, the reaction solution was put into a beaker containing water (200 mL). The resulting mixture was filtered, and the residue on the filter was washed with water (30 mL) and with methanol (20 mL). The resulting crude product was recrystallized (chloroform/acetone) to obtain a compound represented by the formula (A-82) below, as a black green powder (actual yield: 0.67 g, percent yield: 94%).

$^{1}$H-NMR (400 MHz, THF-d$_{8}$): δ (ppm)=3.68 (24H), 6.72 (16H), 6.91 (16H), 7.07 (4H), 7.34 (4H), 7.66 (4H), 7.74 (4H), 7.89 (2H), 7.99 (6H), 8.81 (2H).

(A-82)

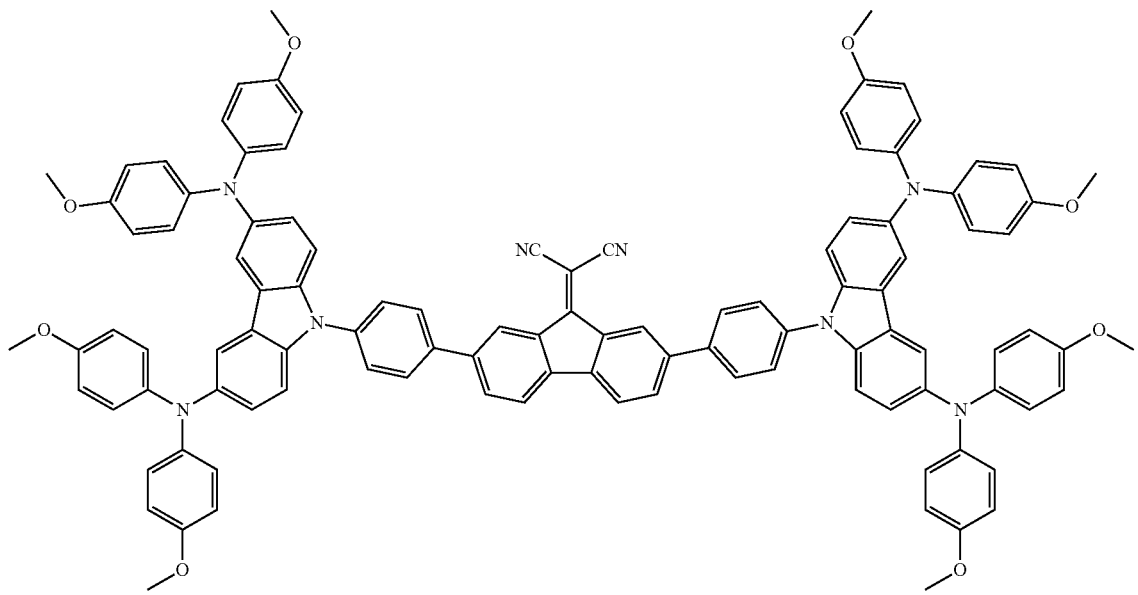

Synthesis Example 10: Synthesis of Compound (A-97)

First, 2,7-dibromofluorenone (0.47 g), the compound of the formula (10) below (2.62 g), tetrakis(triphenylphosphine)palladium(0) (0.065 g, manufactured by Kanto Chemical Co., Inc.), potassium carbonate (0.51 g, manufactured by Kanto Chemical Co., Inc.), toluene (7.5 mL), ethanol (2.5 mL), and water (2.5 mL) were placed in a reaction vessel and degassed under reduced pressure. The mixture was stirred in an argon atmosphere for 8 hours while heating under reflux. After the reaction was completed, toluene (20 mL) and water (10 mL) were added. The resulting mixture was subjected to liquid-liquid separation. The aqueous layer was washed with toluene (20 mL) twice, and the organic layer was concentrated. The resulting crude product was purified using a silica gel column (toluene:ethyl acetate=50/1 (volume ratio)) to obtain a compound represented by the formula (A-97) below, as a red powder (actual yield: 1.95 g, percent yield: 86%).

$^1$H-NMR (400 MHz, THF-d$_8$): δ (ppm)=3.73 (24H), 6.59-6.65 (8H), 6.74 (4H), 6.80 (16H), 6.97 (16H), 7.35 (4H), 7.75 (2H), 7.80 (4H), 7.86 (2H), 7.94 (2H).

(10)

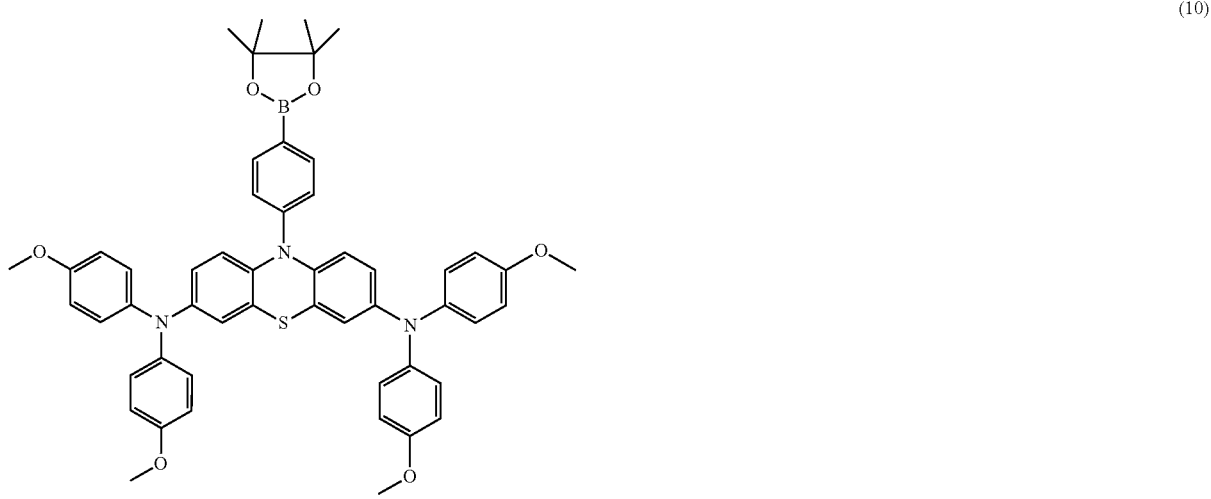

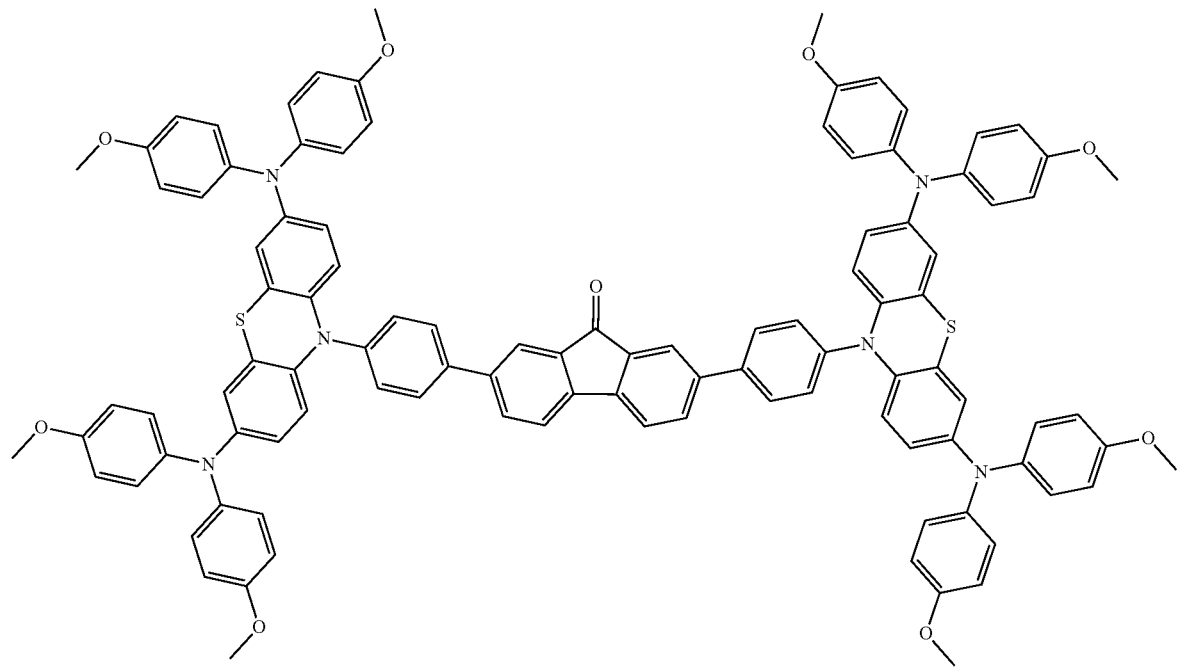

(A-97)

Synthesis Example 11: Synthesis of Compound (A-113)

The compound of the above formula (A-97) (0.60 g), malononitrile (0.10 g, manufactured by Tokyo Chemical Industry Co., Ltd.), and THF (15 mL) were placed in a reaction vessel and stirred in an argon atmosphere. Acetic acid (1.3 mL, manufactured by Kanto Chemical Co., Inc.) and pyridine (1.3 mL, manufactured by Nacalai Tesque, Inc.) were added thereto, and the mixture was stirred for 20 hours while heating under reflux. After the reaction was completed, the reaction solution was poured into water (200 mL). The resulting mixture was filtered, and the residue on the filter was washed with water (30 mL) and with methanol (20 mL). The resulting crude product was washed with toluene and then recrystallized (chloroform/acetone) to obtain a compound represented by the formula (A-113) below, as a green powder (actual yield: 0.56 g, percent yield: 90%).

$^1$H-NMR (400 MHz, THF-d$_8$): δ (ppm)=3.73 (24H), 6.59-6.65 (8H), 6.74 (4H), 6.80 (16H), 6.97 (16H), 7.35 (4H), 7.75 (2H), 7.80 (4H), 7.86 (2H), 8.94 (2H).

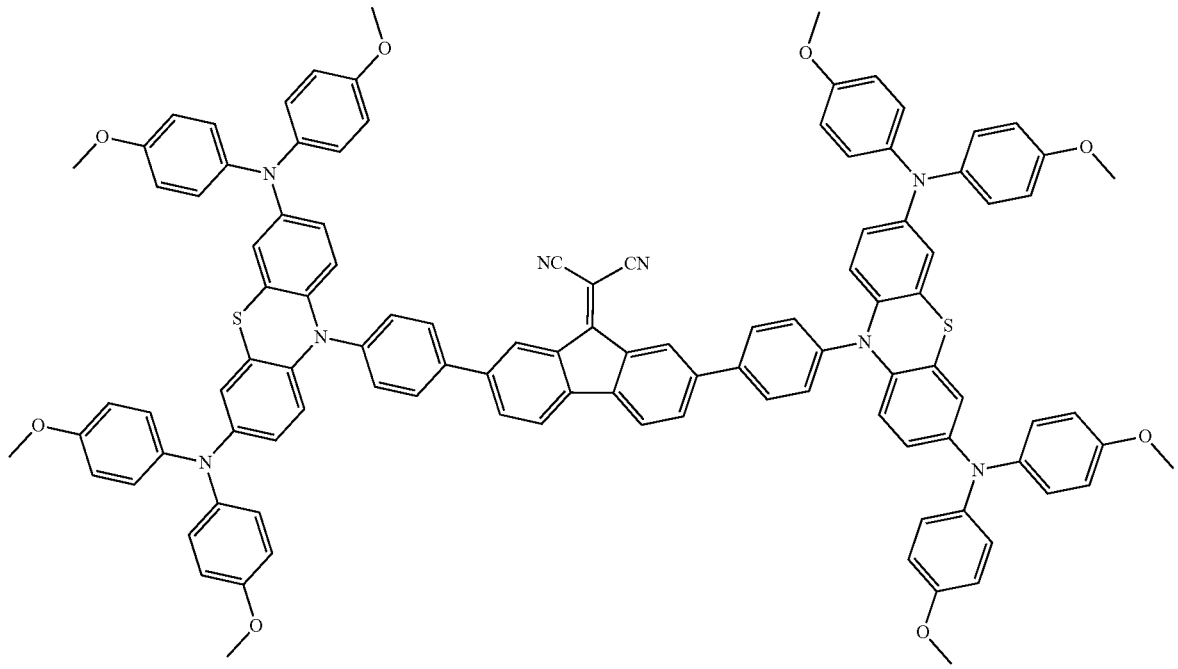

(A-113)

Synthesis Example 12: Synthesis of Compound (A-132)

First, 2,7-dibromofluorenone (0.47 g), the compound of the formula (11) below (2.57 g), tetrakis(triphenylphosphine)palladium(0) (0.065 g, manufactured by Kanto Chemical Co., Inc.), potassium carbonate (0.51 g, manufactured by Kanto Chemical Co., Inc.), toluene (7.5 mL), ethanol (2.5 mL), and water (2.5 mL) were placed in a reaction vessel and degassed under reduced pressure. The mixture was heated under reflux for 7 hours in an argon atmosphere. After the reaction was completed, toluene (20 mL) and water (10 mL) were added. The resulting mixture was subjected to liquid-liquid separation. The aqueous layer was washed with toluene (20 mL) twice, and the organic layer was concentrated. The resulting crude product was purified using a silica gel column (toluene/ethyl acetate=50/1 (volume ratio)) to obtain a compound represented by the formula (A-132) below, as a red powder (actual yield: 1.67 g, percent yield: 75%).

$^1$H-NMR (400 MHz, THF-$d_8$): δ (ppm)=3.75 (24H), 6.60-6.66 (8H), 6.76 (4H), 6.82 (16H), 6.97 (16H), 7.36 (4H), 7.78 (2H), 7.83 (4H), 7.87 (2H), 7.95 (2H).

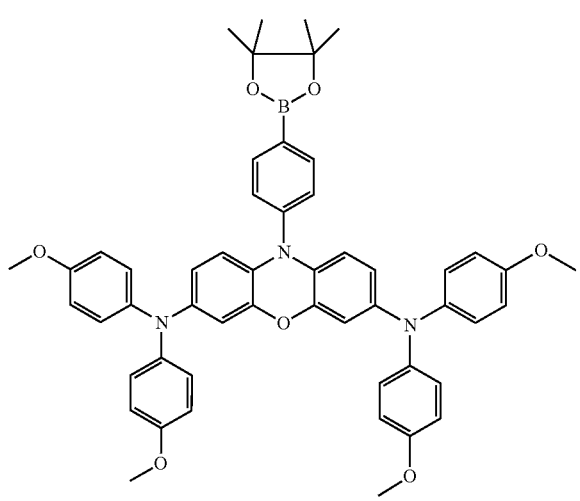

(11)

(A-132)

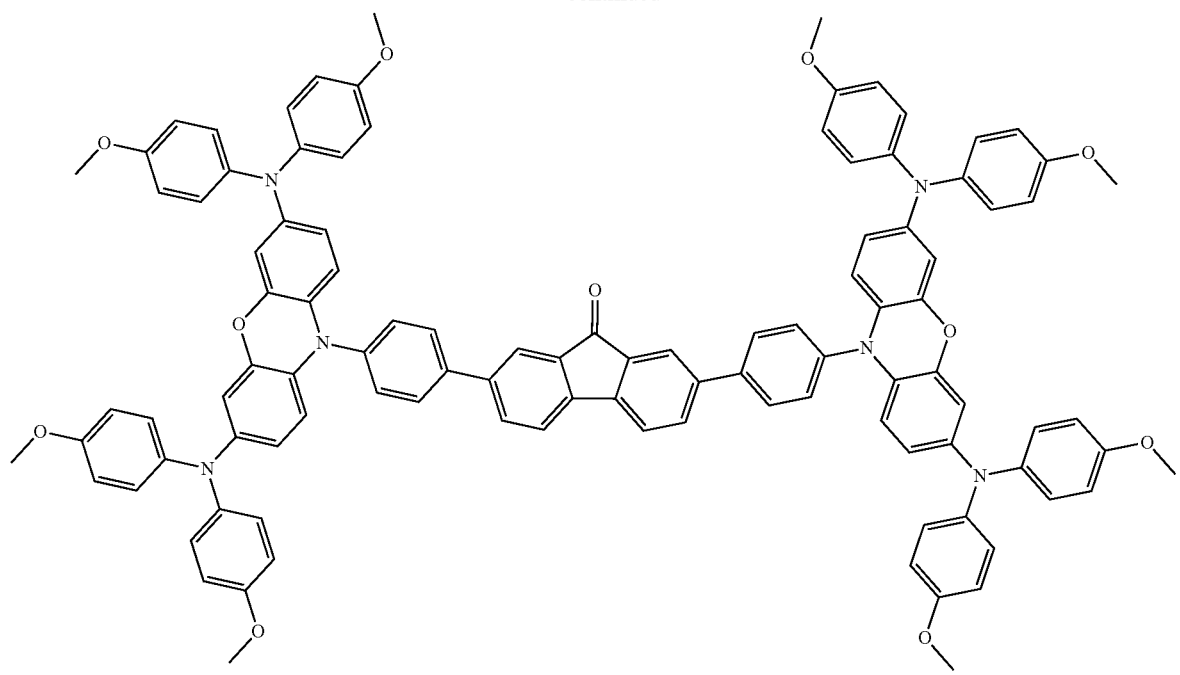

Synthesis Example 13: Synthesis of Compound (A-144)

The compound of the above formula (A-132) (0.60 g), malononitrile (0.10 g, manufactured by Tokyo Chemical Industry Co., Ltd.), and THF (15 mL) were placed in a reaction vessel and stirred in an argon atmosphere. Acetic acid (1.3 mL, manufactured by Kanto Chemical Co., Inc.) and pyridine (1.3 mL, manufactured by Nacalai Tesque, Inc.) were added thereto, and the mixture was stirred for 15 hours while heating under reflux. After the reaction was completed, the reaction solution was poured into water (200 mL). The resulting mixture was filtered, and the residue on the filter was washed with water (30 mL) and with methanol (20 mL). The resulting crude product was recrystallized (chloroform/acetone) to obtain a compound represented by the formula (A-144) below, as a green powder (actual yield: 0.54 g, percent yield: 88%).

$^1$H-NMR (400 MHz, THF-d$_8$): δ (ppm)=3.75 (24H), 6.60-6.66 (8H), 6.76 (4H), 6.82 (16H), 6.97 (16H), 7.36 (4H), 7.78 (2H), 7.83 (4H), 7.87 (2H), 8.95 (2H).

[Chem. 34]

(A-144)

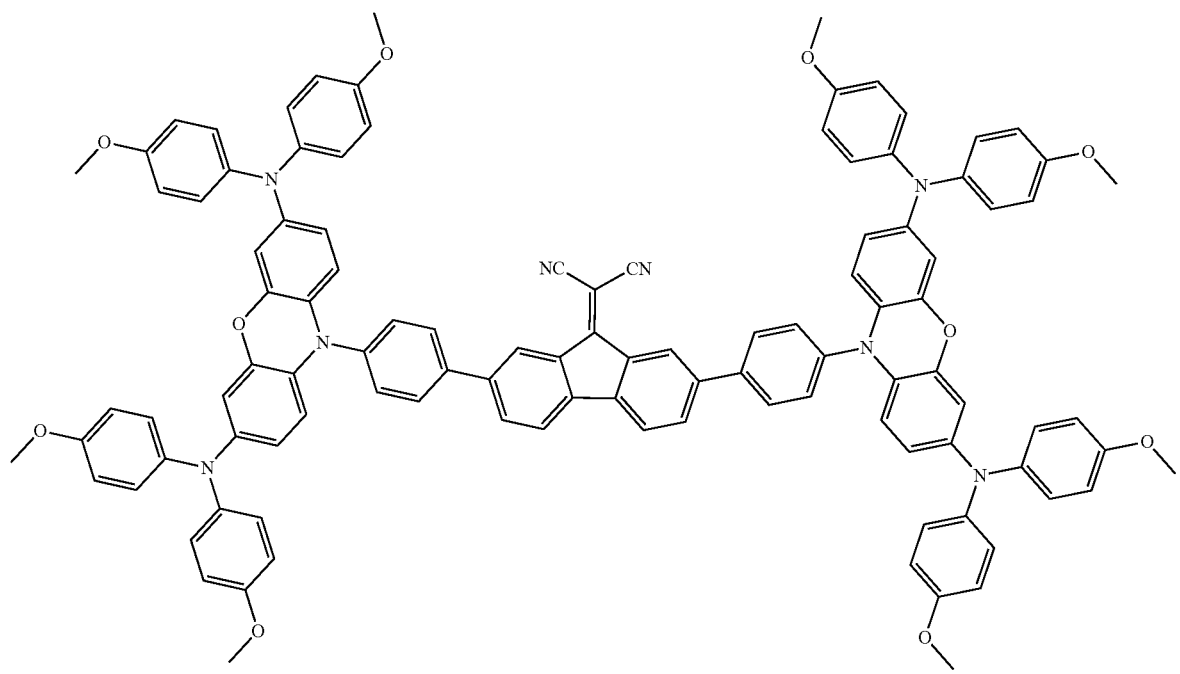

Synthesis Example 14: Synthesis of Compound (A-54)

The compound of the above formula (A-2) (0.6 g), 1,3-diethylthiobarbituric acid (0.38 g, manufactured by Wako Pure Chemical Industries, Ltd.), and THF (24 mL) were placed in a reaction vessel and stirred in an argon atmosphere. Piperidine (0.07 mL) was added thereto. The temperature was raised, and the mixture was heated under reflux for 4 hours. After the reaction was completed, the reaction solution was poured into a beaker containing 300 mL of water. The mixture was filtered, and the residue on the filter was washed with 30 mL of water and with 30 mL of methanol. The resulting crude product was purified using a silica gel column (toluene) to obtain a compound represented by the formula (A-54) below, as a black green powder (actual yield: 0.44 g, percent yield: 60%).

$^1$H-NMR (400 MHz, CDCl$_3$): δ (ppm)=3.81 (12H), 6.85 (8H), 6.98 (4H), 7.10 (8H), 7.43 (4H), 7.53 (2H), 7.67 (2H), 8.41 (2H).

[Chem. 35]

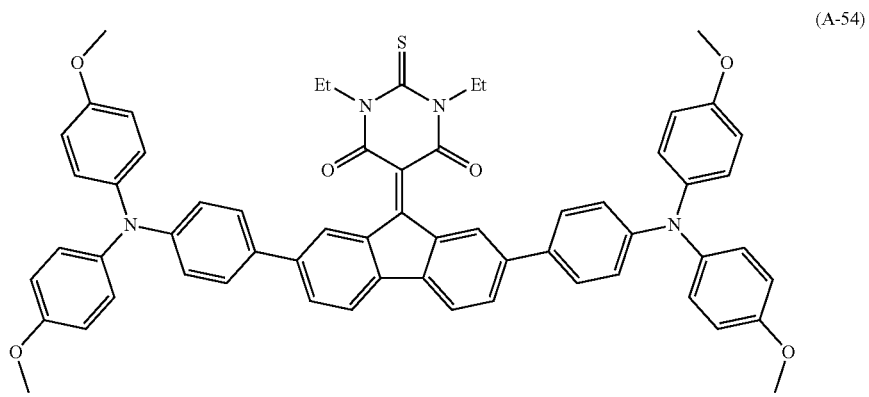

(A-54)

Synthesis of Compound (A-8)

Synthesis Example 15

First, 2,7-dibromofluorenone (0.68 g, manufactured by Tokyo Chemical Industry Co., Ltd.), the compound of the formula (12) below (2.52 g), potassium carbonate (0.72 g, manufactured by Kanto Chemical Co., Inc.), tetrakis(triphenylphosphine)palladium (0.09 g, manufactured by Kanto Chemical Co., Inc.), toluene (11 mL), ethanol (3 mL), and water (3 mL) were placed in a reaction vessel and degassed under reduced pressure. The mixture was stirred for 10 hours while heating under reflux. After the reaction was completed, the reaction solution was put into a beaker containing water (100 mL). Toluene (20 mL) was added thereto, and then liquid-liquid separation was performed. The organic layer was dried over magnesium sulfate and then concentrated. The resulting crude product was purified using a silica gel column (toluene:hexane=2/1 (volume ratio)) to obtain a compound represented by the formula (A-8) below, as a red powder (actual yield: 1.79 g, percent yield: 84%).

$^1$H-NMR (400 MHz, CDCl$_3$): δ (ppm)=0.92 (12H), 1.31-1.36 (16H), 1.40-1.47 (8H), 1.74-1.81 (8H), 3.94 (8H), 6.84 (8H), 6.98 (4H), 7.08 (8H), 7.43 (4H), 7.52 (2H), 7.60 (2H), 7.86 (2H).

[Chem. 36]

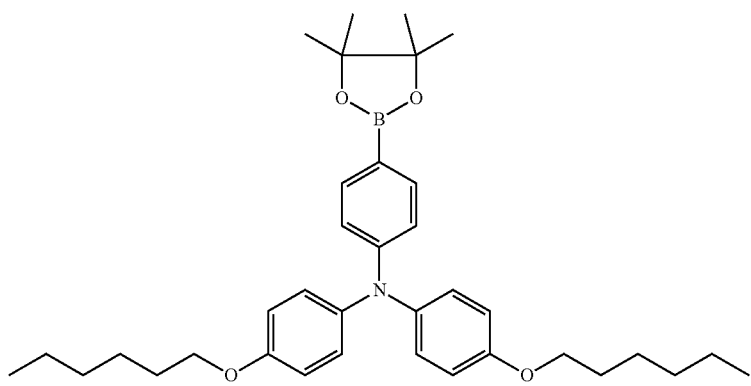

(12)

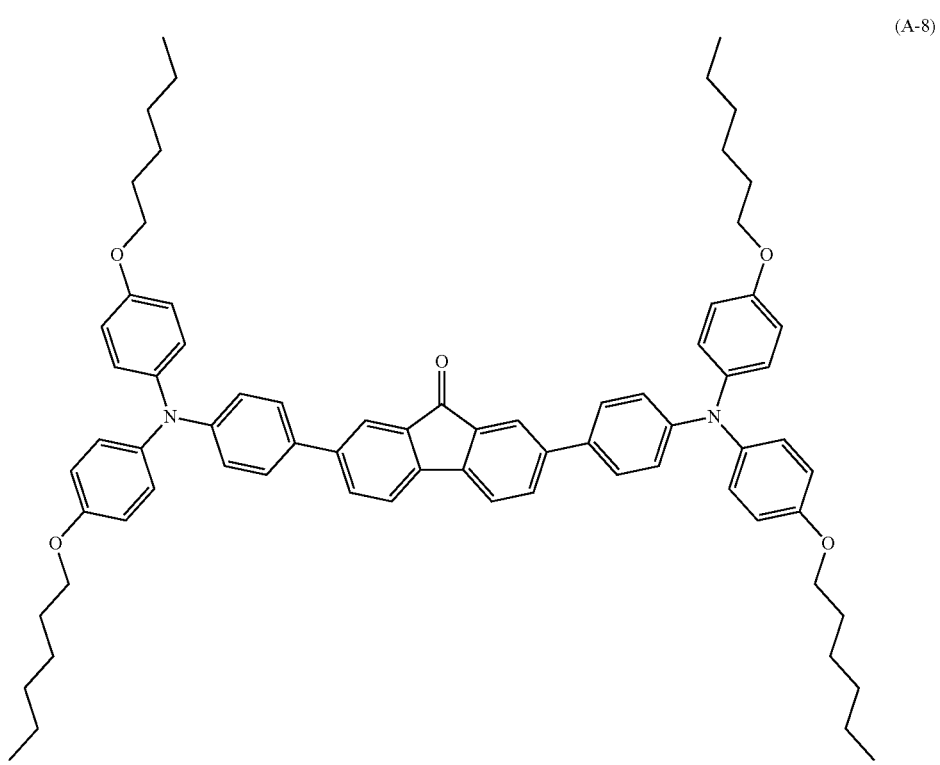

(A-8)

Synthesis Example 16: Synthesis of Compound (A-20)

The compound of the above formula (A-8) (0.68 g), malononitrile (0.22 g, manufactured by Tokyo Chemical Industry Co., Ltd.), and THF (26 mL) were placed in a reaction vessel and stirred in an argon atmosphere. A mixture of acetic acid and pyridine (volume ratio=1:1) (4.6 mL) was added thereto, and the resulting mixture was stirred for 19 hours while heating under reflux. After the reaction was completed, the reaction solution was poured into water (150 mL). Toluene (20 mL) was added thereto, and liquid-liquid separation was performed. The organic layer was dried over magnesium sulfate and then concentrated. The resulting crude product was purified using a silica gel column (toluene) to obtain a compound represented by the formula (A-20) below, as a black green solid (actual yield: 0.59 g, percent yield: 83%).

$^1$H-NMR (400 MHz, CDCl$_3$): δ (ppm)=0.92 (12H), 1.31-1.36 (16H), 1.40-1.47 (8H), 1.74-1.81 (8H), 3.94 (8H), 6.84 (8H), 6.98 (4H), 7.08 (8H), 7.43 (4H), 7.52 (2H), 7.65 (2H), 8.57 (2H).

[Chem. 37]

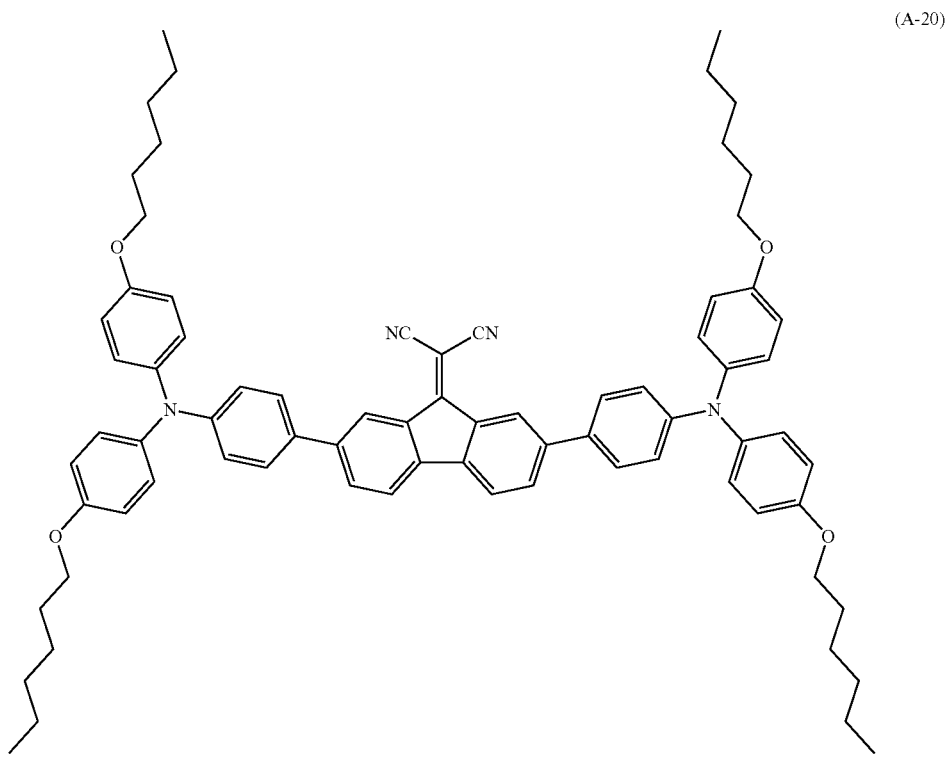

(A-20)

Synthesis Example 17: Synthesis of Compound (A-11)

First, a compound represented by the formula (13) below (1.10 g), [4-[bis(4-methoxyphenyl)amino]phenyl]boronic acid (1.75 g, manufactured by Tokyo Chemical Industry Co., Ltd.), potassium carbonate (0.82 g, manufactured by Kanto Chemical Co., Inc.), tetrakis triphenylphosphinepalladium (0.10 g, manufactured by Kanto Chemical Co., Inc.), toluene (18 mL), ethanol (5.1 mL), and water (5.1 mL) were placed in a reaction vessel and degassed under reduced pressure. The mixture was heated under reflux for 6 hours. After the reaction was completed, the reaction solution was cooled to 40° C. or below, and water (10 mL) and methanol (10 mL) were added. The resulting mixture was filtered, and the residue on the filter was washed with methanol (10 mL) and dried. The resulting crude product was purified using a silica gel column (chloroform:toluene=50/1 (volume ratio)) to obtain a compound represented by the formula (A-11) below, as a red powder (actual yield: 1.79 g, percent yield: 86%).

$^1$H-NMR (400 MHz, CDCl$_3$): δ (ppm)=3.81 (12H), 6.86 (8H), 6.93 (4H), 7.09 (8H), 7.18 (2H), 7.34 (2H), 7.42 (4H), 7.50 (2H), 7.71 (2H), 7.92 (2H).

[Chem. 38]

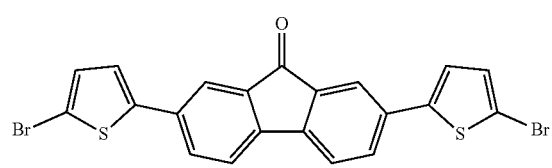

(13)

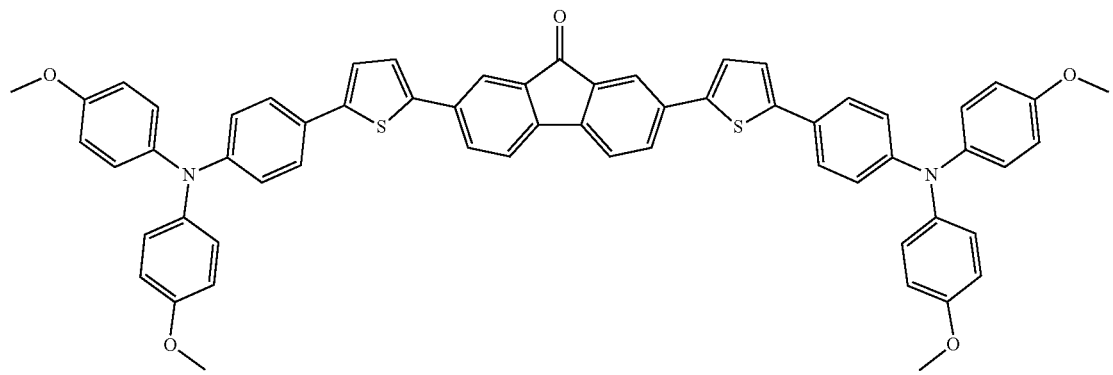

(A-11)

Synthesis Example 18: Synthesis of Compound (A-23)

The compound represented by the above formula (A-11) (0.73 g), malononitrile (0.22 g, manufactured by Tokyo Chemical Industry Co., Ltd.), and THF (26 mL) were placed in a reaction vessel and stirred in an argon atmosphere. A mixture of acetic acid and pyridine (volume ratio=1:1) (4.6 mL) was added thereto, and the resulting mixture was heated under reflux for 15 hours. After the reaction was completed, the reaction solution was poured into water (150 mL). The resulting mixture was filtered, and the residue on the filter was washed with methanol (20 mL) and then dried. The resulting crude product was purified using a silica gel column (chloroform) to obtain a compound represented by the formula (A-23) below, as a black green solid (actual yield: 0.63 g, percent yield: 83%).

$^1$H-NMR (400 MHz, CDCl$_3$): δ (ppm)=3.81 (12H), 6.87 (8H), 6.93 (4H), 7.09 (8H), 7.18 (2H), 7.34 (2H), 7.42 (4H), 7.60 (2H), 7.90 (2H), 8.65 (2H).

Synthesis Example 19: Synthesis of Compound (A-36)

The compound of the above formula (A-11) (0.45 g), diethyl malonate (0.42 mL, manufactured by Tokyo Chemical Industry Co., Ltd.), and THF (15 mL) were placed in a reaction vessel and stirred in an argon atmosphere. The mixture was cooled to 5° C. or below in an ice bath, and pyridine (0.63 mL) was added. The mixture was cooled again to 5° C. or below, and titanium tetrachloride (0.32 mL, manufactured by Wako Pure Chemical Industries, Ltd.) was added. The temperature was then raised, and the mixture was heated under reflux for 9 hours. After the reaction was completed, the reaction solution was put into a beaker containing water (150 mL). The resulting mixture was filtered, and the residue on the filter was washed with water (10 mL) and with methanol (30 mL), and dried. The resulting crude product was purified using a silica gel column (chloroform) to obtain a compound represented by the formula (A-36) below, as a brown powder (actual yield: 0.36 g, percent yield: 71%).

$^1$H-NMR (400 MHz, THF-d$_8$): δ (ppm)=1.39 (6H), 3.78 (12H), 4.50 (4H), 6.83-6.90 (12H), 7.05 (8H), 7.24 (2H), 7.35 (2H), 7.45 (4H), 7.71 (4H), 8.20 (2H).

[Chem. 39]

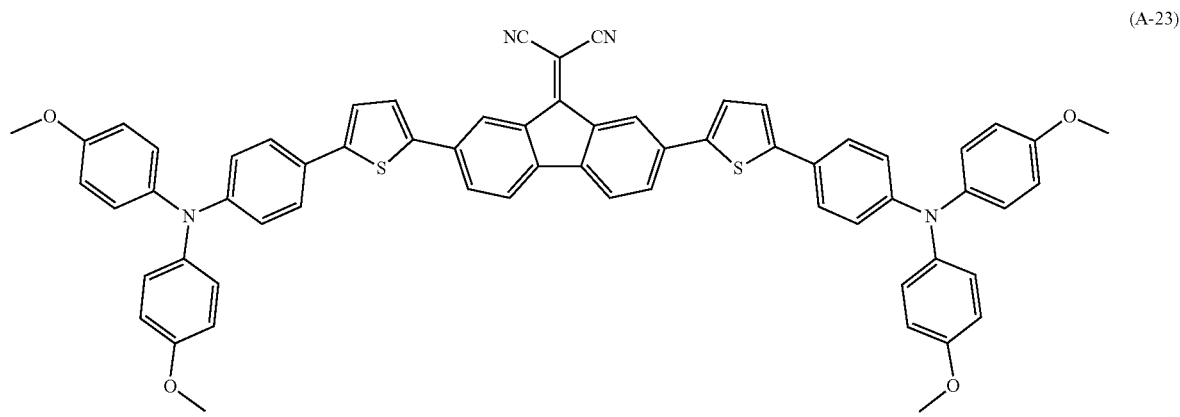

(A-23)

[Chem. 40]

(A-36)

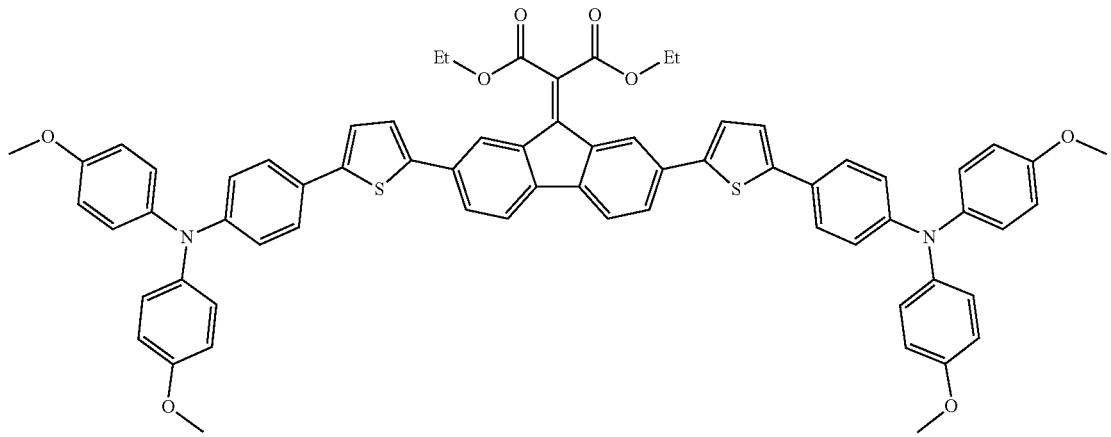

Synthesis Example 20: Synthesis of Compound (A-49)

The compound of the above formula (A-11) (0.45 g), methyl cyanoacetate (0.25 mL, manufactured by Tokyo Chemical Industry Co., Ltd.), and THF (15 mL) were placed in a reaction vessel and stirred in an argon atmosphere. The mixture was cooled to 5° C. or below in an ice bath, and pyridine (0.63 mL) was added. The mixture was cooled again to 5° C. or below, and titanium tetrachloride (0.32 mL, manufactured by Wako Pure Chemical Industries, Ltd.) was added. The temperature was then raised, and the mixture was heated under reflux for 9 hours. After the reaction was completed, the reaction solution was put into a beaker containing water (150 mL). The resulting mixture was filtered, and the residue on the filter was washed with water (10 mL) and with methanol (30 mL), and dried. The resulting crude product was purified using a silica gel column (chloroform) to obtain a compound represented by the formula (A-49) below, as a brown powder (actual yield: 0.46 g, percent yield: 94%).

$^1$H-NMR (400 MHz, THF-d$_8$): δ (ppm)=3.78 (12H), 4.07 (3H), 6.84-6.89 (12H), 7.05 (8H), 7.24 (2H), 7.37 (1H), 7.40 (1H), 7.45 (4H), 7.71 (4H), 8.43 (1H), 8.92 (1H).

[Chem. 41]

(A-49)

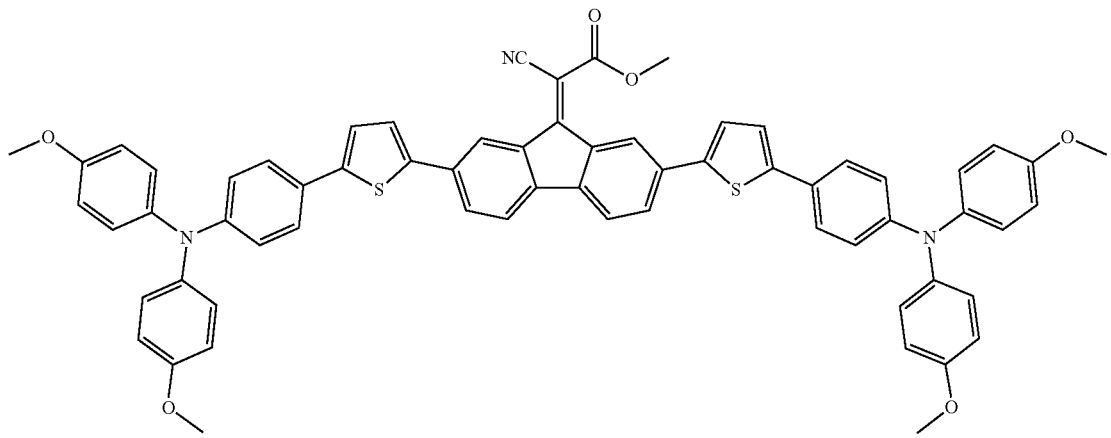

Synthesis Example 21: Synthesis of Compound (A-79)

The compound of the above formula (13) (0.50 g), the compound of the above formula (9) (1.89 g), potassium carbonate (0.37 g, manufactured by Kanto Chemical Co., Inc.), tetrakis triphenylphosphinepalladium (0.05 g, manufactured by Kanto Chemical Co., Inc.), toluene (10 mL), ethanol (2.3 mL), and water (2.3 mL) were placed in a reaction vessel and degassed under reduced pressure. The mixture was heated under reflux for 13 hours. After the reaction was completed, the reaction solution was put into a beaker containing water (100 mL). The resulting mixture was filtered, and the residue on the filter was washed with water (10 mL) and with methanol (30 mL), and dried. The resulting crude product was purified using a silica gel column (toluene:ethyl acetate=30/1 (volume ratio)) to obtain a compound represented by the formula (A-79) below, as a reddish brown powder (actual yield: 1.23 g, percent yield: 71%).

¹H-NMR (400 MHz, DMSO-d₆): δ (ppm)=3.70 (24H), 6.82 (16H), 6.88 (16H), 7.09 (4H), 7.32 (4H), 7.64 (6H), 7.67 (4H), 7.70 (2H), 7.84 (2H), 7.89 (2H), 7.94 (6H).

under reflux for 19 hours. After the reaction was completed, the reaction solution was poured into water (100 mL). The resulting mixture was filtered, and the residue on the filter was washed with methanol (20 mL) and then dried. The resulting crude product was recrystallized (chloroform) to obtain a compound represented by the formula (A-95) below, as a black green solid (actual yield: 0.54 g, percent yield: 80%).

¹H-NMR (400 MHz, DMSO-d₆): δ (ppm)=3.70 (24H), 6.82 (16H), 6.88 (16H), 7.09 (4H), 7.32 (4H), 7.65 (6H), 7.67 (4H), 7.80 (2H), 7.98 (2H), 8.01 (2H), 8.12 (6H).

[Chem. 42]

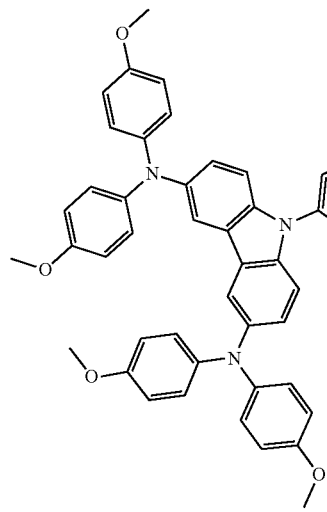
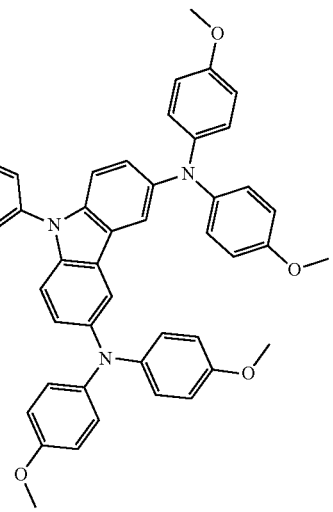

(A-79)

Synthesis Example 22: Synthesis of Compound (A-95)

The compound of the above formula (A-79) (0.66 g), malononitrile (0.11 g, manufactured by Tokyo Chemical Industry Co., Ltd.), and THF (15 mL) were placed in a reaction vessel and stirred in an argon atmosphere. A mixture of acetic acid and pyridine (volume ratio=1:1) (2.3 mL) was added thereto, and the resulting mixture was heated

[Chem. 43]

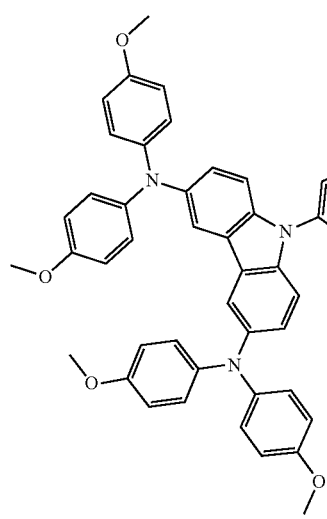
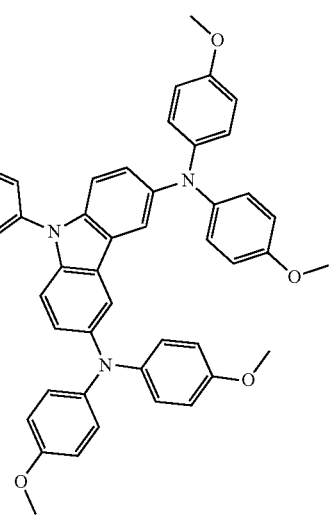

(A-95)

Synthesis Example 23: Synthesis of Compound (A-96)

The compound of the above formula (A-79) (0.40 g), diethyl malonate (0.20 mL, manufactured by Tokyo Chemical Industry Co., Ltd.), and THF (9 mL) were placed in a reaction vessel and stirred in an argon atmosphere. The mixture was cooled to 5° C. or below in an ice bath, and pyridine (0.31 mL) was added. The mixture was cooled again to 5° C. or below, and titanium tetrachloride (0.16 mL, manufactured by Wako Pure Chemical Industries, Ltd.) was added. The temperature was then raised, and the mixture was heated under reflux for 6 hours. After the reaction was completed, the reaction solution was put into a beaker containing water (150 mL). The resulting mixture was filtered, and the residue on the filter was washed with water (10 mL) and with methanol (30 mL), and dried. The resulting crude product was purified using a silica gel column (toluene:ethyl acetate=20/1 (volume ratio)) to obtain a compound represented by the formula (A-96) below, as a black green powder (actual yield: 0.07 g, percent yield: 16%).

$^1$H-NMR (400 MHz, DMSO-d$_6$): δ (ppm)=1.42 (6H), 3.78 (12H), 4.52 (4H), 6.83-6.91 (20H), 6.88 (16H), 7.40 (4H), 7.62 (6H), 7.65 (4H), 7.68 (2H), 7.80 (2H), 7.85 (2H), 7.89 (6H).

Synthesis Example 24: Synthesis of Compound (A-83)

The compound of the above formula (A-67) (0.30 g), methyl cyanoacetate (0.10 mL, manufactured by Tokyo Chemical Industry Co., Ltd.), and THF (7 mL) were placed in a reaction vessel and stirred in an argon atmosphere. The mixture was cooled to 5° C. or below in an ice bath, and pyridine (0.25 mL) was added. The mixture was cooled again to 5° C. or below, and titanium tetrachloride (0.13 mL, manufactured by Wako Pure Chemical Industries, Ltd.) was added. The temperature was then raised, and the mixture was heated under reflux for 9 hours. After the reaction was completed, water (20 mL) and toluene (10 mL) were added, and liquid-liquid separation was performed. The organic layer was dried over magnesium sulfate and then concentrated. The resulting crude product was purified using a silica gel column (toluene:ethyl acetate=40/1 (volume ratio)) to obtain a compound represented by the formula (A-83) below, as a black green powder (actual yield: 0.22 g, percent yield: 70%).

$^1$H-NMR (400 MHz, THF-d$_8$): δ (ppm)=3.71 (24H), 4.06 (3H), 6.74 (16H), 6.93 (16H), 7.11 (4H), 7.33 (4H), 7.69-7.76 (8H), 7.88-7.99 (8H), 8.63 (1H), 9.07 (1H).

[Chem. 44]

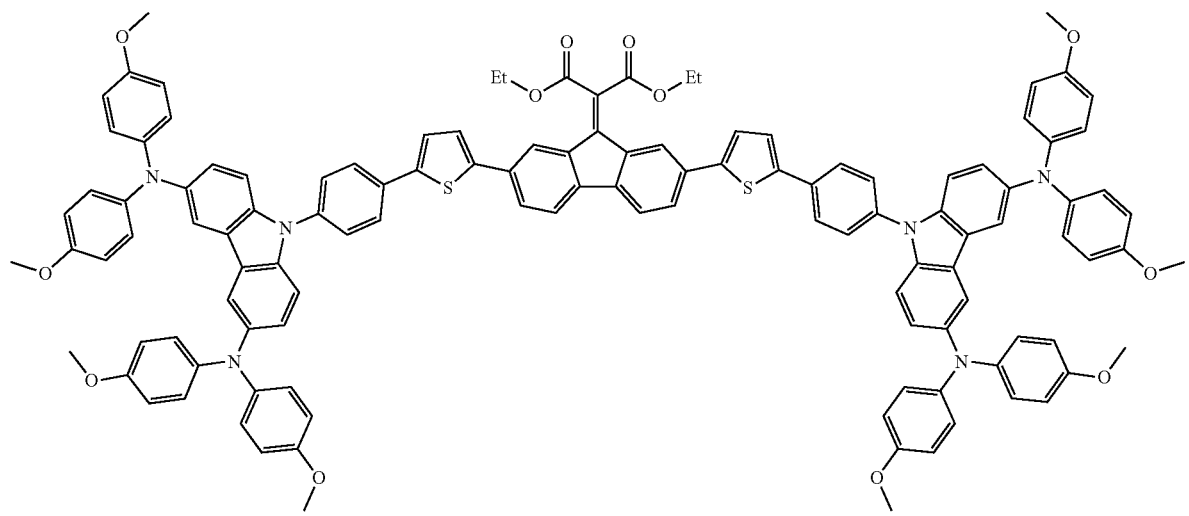

(A-96)

[Chem. 45]

(A-83)

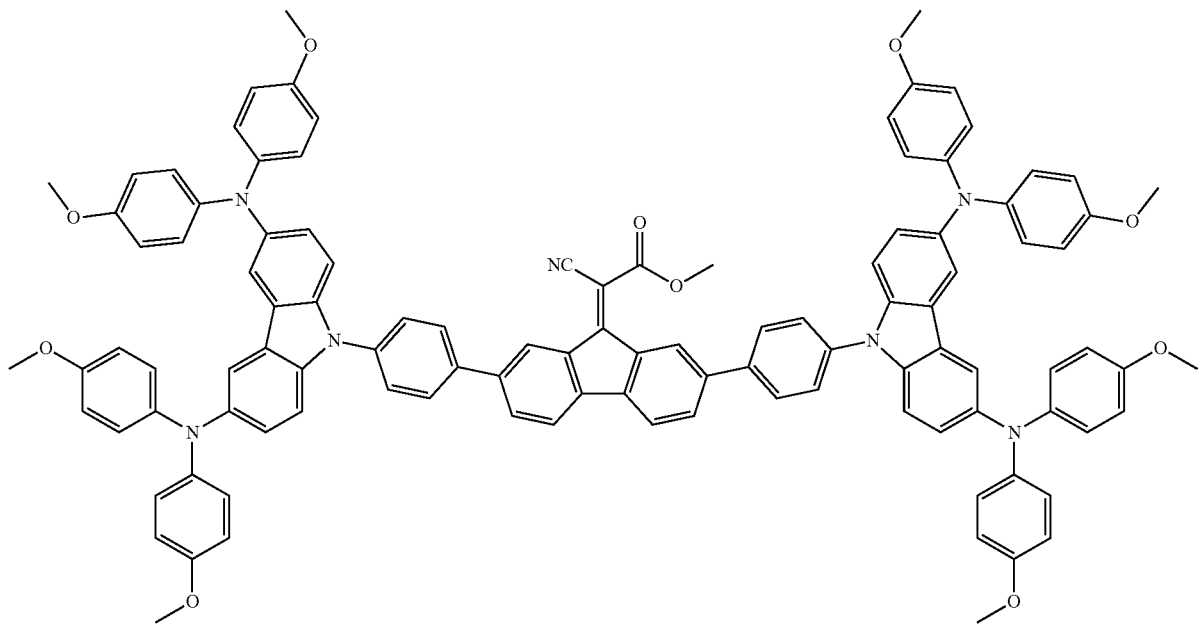

Synthesis Example 25: Synthesis of Compound (A-155)

The compound of the above formula (A-67) (0.30 g), diethyl malonate (0.18 mL, manufactured by Tokyo Chemical Industry Co., Ltd.), and THF (7 mL) were placed in a reaction vessel and stirred in an argon atmosphere. The mixture was cooled to 5° C. or below in an ice bath, and pyridine (0.25 mL) was added. The mixture was cooled again to 5° C. or below, and titanium tetrachloride (0.13 mL, manufactured by Wako Pure Chemical Industries, Ltd.) was added. The temperature was then raised, and the mixture was heated under reflux for 9 hours. After the reaction was completed, water (20 mL) and toluene (10 mL) were added, and liquid-liquid separation was performed. The organic layer was dried over magnesium sulfate and then concentrated. The resulting crude product was purified using a silica gel column (toluene:ethyl acetate=50/1 (volume ratio)) to obtain a compound represented by the formula (A-155) below, as a black green powder (actual yield: 0.26 g, percent yield: 78%).

$^1$H-NMR (400 MHz, THF-$d_8$): δ (ppm)=1.35 (6H), 3.71 (24H), 4.45 (4H), 6.73 (16H), 6.91 (16H), 7.10 (4H), 7.35 (4H), 7.70-7.72 (8H), 7.84-7.91 (8H), 8.34 (2H).

[Chem. 46]

(A-155)

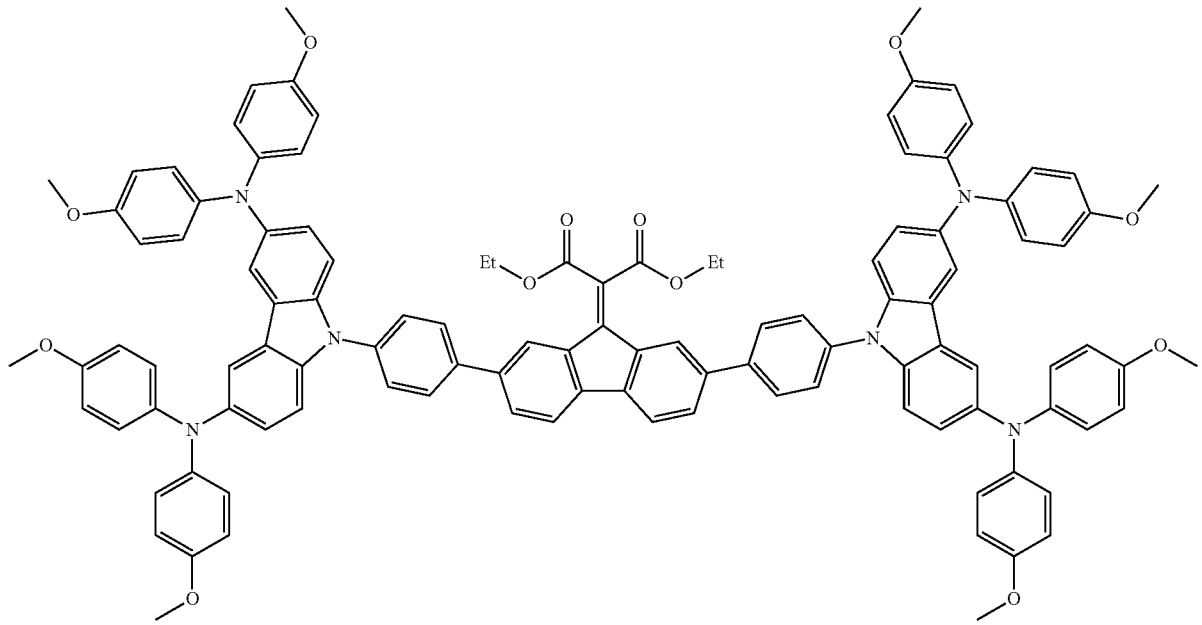

Example 1: Production of Device for Converting Light into Electricity and Evaluation of Current-Voltage Characteristics Thereof A glass substrate with an etched, fluorine-doped tin oxide (FTO) coating (conductive support 1, manufactured by Solaronix) was ultrasonically cleaned in isopropyl alcohol and then treated with UV/ozone.

Tin(IV) oxide, 15% in $H_2O$ colloidal dispersion (manufactured by Alfa Aesar) and purified water were mixed in a volume ratio of 1:3 to obtain a tin oxide dispersion (coating solution for an electron transport layer), and the FTO coating was spin-coated with the coating solution for an electron transport layer. After that, the resultant was heated at 150° C. for 30 minutes using a hot plate to form a tin oxide thin film (electron transport layer 2) having a film thickness of about 40 nm.

Under a nitrogen stream in a glove box, formamidine hydroiodide (1 M, manufactured by Tokyo Chemical Industry Co., Ltd.), lead(II) iodide (1.1 M, manufactured by Tokyo Chemical Industry Co., Ltd.), methylamine hydrobromide (0.2 M, manufactured by Tokyo Chemical Industry Co., Ltd.), and lead(II) bromide (0.2 M, manufactured by Tokyo Chemical Industry Co., Ltd.) were dissolved in a solvent mixture of dimethylformamide and dimethyl sulfoxide in a volume ratio of 4:1. A cesium iodide (1.5 M, manufactured by Tokyo Chemical Industry Co., Ltd.) solution in dimethyl sulfoxide was added thereto such that the amount of cesium added was 5% in terms of the percent composition. Thus, a perovskite precursor solution was prepared.

Under a nitrogen atmosphere in a glove box, the perovskite precursor solution was dropped on the tin oxide thin film, followed by spin-coating. During the spin-coating, 0.3 mL of chlorobenzene was dropped. Thus, a perovskite precursor film was formed.

After that, the resultant was heated at 100° C. for 1 hour using a hot plate, to thereby form a Cs(MAFA)Pb(IBr)$_3$ layer (light/electricity conversion layer 3) having a film thickness of about 500 nm.

Under a nitrogen stream in a glove box, 4-tert-butylpyridine and lithium bis(trifluoromethanesulfonyl)imide as dopants were dissolved in chlorobenzene. The compound (A-2), which was a hole transport material obtained in Synthesis Example 1, was dissolved in the dopant solution in chlorobenzene to a concentration of 50 mM. The amounts of 4-tert-butylpyridine and lithium bis(trifluoromethanesulfonyl)imide were adjusted to 3 equivalents and 0.5 equivalents, respectively, with respect to the compound (A-2). Thus, a coating solution for a hole transport layer was obtained.

Under a nitrogen atmosphere in a glove box, the Cs(MAFA)Pb(IBr)$_3$ layer (light/electricity conversion layer 3) was spin-coated with the coating solution for a hole transport layer, to thereby form a hole transport layer 4 having a film thickness of about 200 nm.

Vacuum evaporation was performed (degree of vacuum: about $1\times10^{-4}$ Pa) to form a gold film having a thickness of 80 to 100 nm as a gold electrode (counter electrode 5) on the hole transport layer.

Thus, a device for converting light into electricity was produced.

The conductive support side of the device for converting light into electricity was irradiated with simulated sunlight (AM1.5, 100 mW/cm$^2$) generated by a solar simulator (model OTENTO-SUN SH, manufactured by Bunkoukeiki Co., Ltd.), and power conversion efficiency was determined by determining current-voltage characteristics using a source meter (Model 2400 Series SourceMeter, manufactured by KEITHLEY). Table 1 shows the current-voltage characteristics and the power conversion efficiency.

Example 2

A device for converting light into electricity was produced in the same manner as in Example 1, except that, instead of the compound (A-2), the compound (A-15) was dissolved in the dopant solution in chlorobenzene to a concentration of 30 mM and used. Then, the power conversion efficiency was determined by determining current-voltage characteristics in the same manner as in Example 1. Table 1 shows the current-voltage characteristics and the power conversion efficiency.

Example 3

A device for converting light into electricity was produced in the same manner as in Example 1, except that the compound (A-28) was used instead of the compound (A-2). Then, the power conversion efficiency was determined by determining current-voltage characteristics in the same manner as in Example 1. Table 1 shows the current-voltage characteristics and the power conversion efficiency.

Example 4

A device for converting light into electricity was produced in the same manner as in Example 1, except that the compound (A-41) was used instead of the compound (A-2). Then, the power conversion efficiency was determined by determining current-voltage characteristics in the same manner as in Example 1. Table 1 shows the current-voltage characteristics and the power conversion efficiency.

Example 5

A device for converting light into electricity was produced in the same manner as in Example 1, except that the compound (A-67) was used instead of the compound (A-2). Then, the power conversion efficiency was determined by determining current-voltage characteristics in the same manner as in Example 1. Table 1 shows the current-voltage characteristics and the power conversion efficiency.

Comparative Example 1

A device for converting light into electricity was produced in the same manner as in Example 1, except that a standard hole transport material Spiro-OMeTAD (manufactured by Sigma-Aldrich) represented by the formula (B-1) below was used instead of the compound (A-2). Then, the power conversion efficiency was determined by determining current-voltage characteristics in the same manner as in Example 1. Table 1 shows the current-voltage characteristics and the power conversion efficiency.

[Chem. 47]

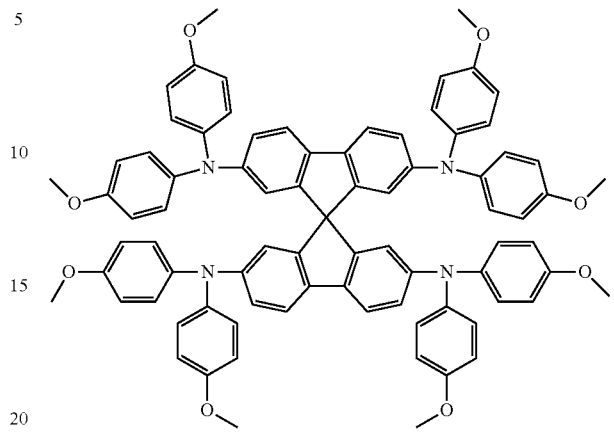

(B-1)

TABLE 1

| | Hole transport material | Short-circuit current density Jsc [mA/cm$^2$] | Open-circuit voltage Voc [V] | Fill factor FF | Power conversion efficiency PCE [%] |
|---|---|---|---|---|---|
| Ex. 1 | (A-2) | 22.28 | 1.07 | 0.72 | 17.43 |
| Ex. 2 | (A-15) | 22.61 | 1.04 | 0.66 | 15.81 |
| Ex. 3 | (A-28) | 20.98 | 1.13 | 0.73 | 17.56 |
| Ex. 4 | (A-41) | 22.83 | 1.01 | 0.67 | 15.69 |
| Ex. 5 | (A-67) | 22.30 | 1.01 | 0.71 | 15.98 |
| Com. Ex. 1 | (B-1) | 22.27 | 1.00 | 0.69 | 15.38 |

It can be seen from the results in Table 1 that the devices for converting light into electricity each including, as the hole transport material, the compound (A-2), (A-15), (A-28), (A-41), or (A-67) having the fluorenone skeleton, which is a compound of the present invention, exhibited higher efficiencies in conversion of light into electricity than the device including the compound (B-1), which is a standard hole transport material.

Example 6: Production of Device for Converting Light into Electricity and Evaluation of Current-Voltage Characteristics Thereof Glass with FLAT ITO coating (conductive support 1, manufactured by Geomatic Co., Ltd.) was ultrasonically cleaned in isopropyl alcohol and then treated with UV/ozone.

Tin(IV) oxide, 15% in $H_2O$ colloidal dispersion (manufactured by Alfa Aesar) and purified water were mixed in a volume ratio of 1:9 to obtain a tin oxide dispersion (coating solution for an electron transport layer), and the ITO coating was spin coated with the coating solution for an electron transport layer. After that, the resultant was heated at 150° C. for 30 minutes using a hot plate to form a tin oxide thin film (electron transport layer 2) having a thickness of about 20 nm.

Under a nitrogen stream in a glove box, formamidine hydroiodide (1 M, manufactured by Tokyo Chemical Industry Co., Ltd.), lead(II) iodide (1.1 M, manufactured by Tokyo Chemical Industry Co., Ltd.), methylamine hydrobromide (0.2 M, manufactured by Tokyo Chemical Industry Co., Ltd.), and lead(II) bromide (0.2 M, manufactured by Tokyo Chemical Industry Co., Ltd.) were dissolved in a solvent mixture of dimethylformamide and dimethyl sulfoxide in a volume ratio of 4:1. A cesium iodide (1.5 M, manufactured by Tokyo Chemical Industry Co., Ltd.) solution in dimethyl sulfoxide was added thereto such that the amount of cesium added was 5% in terms of the percent composition. Thus, a perovskite precursor solution was prepared.

Under a nitrogen atmosphere in a glove box, the perovskite precursor solution was dropped onto the tin oxide thin film, followed by spin-coating. During the spin-coating, 0.3 mL of chlorobenzene was dropped. Thus, a perovskite precursor film was formed.

After that, the resultant was heated at 100° C. for 1 hour using a hot plate, to thereby form a Cs(MAFA)Pb(IBr)$_3$ layer (light/electricity conversion layer 3) having a film thickness of about 500 nm.

Under a nitrogen stream in a glove box, 4-tert-butylpyridine and lithium bis(trifluoromethanesulfonyl)imide as dopants were dissolved in chlorobenzene. The compound (A-36), which was a hole transport material obtained in Synthesis Example 19, was dissolved in the dopant solution in chlorobenzene to a concentration of 30 mM at 60° C. The amounts of 4-tert-butylpyridine and lithium bis(trifluoromethanesulfonyl)imide were adjusted to 3 equivalents and 0.5 equivalents, respectively, with respect to the compound (A-36). Thus, a coating solution for a hole transport layer was obtained.

Under a nitrogen atmosphere in a glove box, the Cs(MAFA)Pb(IBr)$_3$ layer (light/electricity conversion layer 3) was spin-coated with the coating solution for a hole transport layer, to thereby form a hole transport layer 4 having a film thickness of about 200 nm.

Vacuum evaporation was performed (degree of vacuum: about 1×10$^{-4}$ Pa) to form a gold film having a thickness of about 80 nm as a gold electrode (counter electrode 5) on the hole transport layer.

Thus, a device for converting light into electricity was produced.

The conductive support side of the device for converting light into electricity was irradiated with simulated sunlight (AM1.5, 100 mW/cm$^2$) generated by a solar simulator (model OTENTO-SUN SH, manufactured by Bunkoukeiki Co., Ltd.), and the initial power conversion efficiency was determined by determining current-voltage characteristics using a source meter (Model 2400 Series SourceMeter, manufactured by KEITHLEY). Table 2 shows the current-voltage characteristics and the initial power conversion efficiency.

After the determination of the current-voltage characteristics, the device for converting light into electricity was stored in a desiccator containing silica gel for 30 days. Then, current-voltage characteristics were determined again under simulated sunlight irradiation to determine the power conversion efficiency after 30 days.

The retention (%) was calculated using the formula (a-1) below from the initial power conversion efficiency and time-dependent efficiency, which is the power conversion efficiency after 30 days. Table 2 shows the retention.

[Math. 1]

$$\text{Retention (\%)} = \frac{\text{Time-dependent power conversion efficiency}}{\text{Initial power conversion efficiency}} \times 100 \quad (a\text{-}1)$$

Example 7

A device for converting light into electricity was produced in the same manner as in Example 6, except that, instead of the compound (A-36), the compound (A-49) was dissolved in the dopant solution in chlorobenzene to a concentration of 30 mM at 90° C. and used. Then, the initial power conversion efficiency and the power conversion efficiency after 30 days were determined in the same manner as in Example 6. Table 2 shows the initial power conversion efficiency. The retention (%) was calculated using the above formula (a-1) from the power conversion efficiency after 30 days. Table 2 also shows the retention.

Example 8

A device for converting light into electricity was produced in the same manner as in Example 6, except that, instead of the compound (A-36), the compound (A-79) was dissolved in the dopant solution in chlorobenzene to a concentration of 30 mM at 90° C. and used. Then, the initial power conversion efficiency and the power conversion efficiency after 30 days were determined in the same manner as in Example 6. Table 2 shows the initial power conversion efficiency. The retention (%) was calculated using the above formula (a-1) from the power conversion efficiency after 30 days. Table 2 also shows the retention.

Example 9

A device for converting light into electricity was produced in the same manner as in Example 6, except that, instead of the compound (A-36), the compound (A-96) was dissolved in the dopant solution in chlorobenzene to a concentration of 40 mM at room temperature and used. Then, the initial power conversion efficiency and the power conversion efficiency after 30 days were determined in the same manner as in Example 6. Table 2 shows the initial power conversion efficiency. The retention (%) was calculated using the above formula (a-1) from the power conversion efficiency after 30 days. Table 2 also shows the retention.

Example 10

A device for converting light into electricity was produced in the same manner as in Example 6, except that, instead of the compound (A-36), the compound (A-155) was dissolved in the dopant solution in chlorobenzene to a concentration of 50 mM at room temperature and used. Then, the initial power conversion efficiency and the power conversion efficiency after 30 days were determined in the same manner as in Example 6. Table 2 shows the initial power conversion efficiency. The retention (%) was calculated using the above formula (a-1) from the power conversion efficiency after 30 days. Table 2 also shows the retention.

Example 11

A device for converting light into electricity was produced in the same manner as in Example 6, except that, instead of the compound (A-36), the compound (A-83) was dissolved in the dopant solution in chlorobenzene to a concentration of 50 mM at room temperature and used. Then, the initial power conversion efficiency and the power conversion efficiency after 30 days were determined in the same manner as in Example 6. Table 2 shows the initial power conversion efficiency. The retention (%) was calculated using the above formula (a-1) from the power conversion efficiency after 30 days. Table 2 also shows the retention.

Example 12

A device for converting light into electricity was produced in the same manner as in Example 6, except that, instead of the compound (A-36), the compound (A-11) was dissolved in the dopant solution in chlorobenzene to a concentration of 20 mM at 90° C. and used. Then, the initial power conversion efficiency and the power conversion efficiency after 30 days were determined in the same manner as in Example 6. Table 2 shows the initial power conversion efficiency. The retention (%) was calculated using the above formula (a-1) from the power conversion efficiency after 30 days. Table 2 also shows the retention.

Comparative Example 2

A device for converting light into electricity was produced in the same manner as in Example 6, except that, instead of the compound (A-36), a standard hole transport material Spiro-OMeTAD (manufactured by Sigma-Aldrich) represented by the above formula (B-1) was dissolved in the dopant solution in chlorobenzene to a concentration of 50 mM at room temperature and used. Then, the initial power conversion efficiency and the power conversion efficiency after 30 days were determined in the same manner as in Example 6. Table 2 shows the initial power conversion efficiency. The retention (%) was calculated using the above formula (a-1) from the power conversion efficiency after 30 days. Table 2 also shows the retention.

TABLE 2

| | Hole transport material | Short-circuit current density Jsc [mA/cm$^2$] | Open-circuit voltage Voc [V] | Fill factor FF | Power conversion efficiency PCE [%] | Retention [%] |
|---|---|---|---|---|---|---|
| Ex. 6 | (A-36) | 20.77 | 1.04 | 0.62 | 13.32 | 122.87 |
| Ex. 7 | (A-37) | 21.97 | 1.00 | 0.67 | 14.79 | 104.27 |
| Ex. 8 | (A-79) | 22.46 | 1.07 | 0.74 | 17.96 | 92.75 |
| Ex. 9 | (A-96) | 20.76 | 1.05 | 0.67 | 14.66 | 109.55 |
| Ex. 10 | (A-155) | 21.84 | 1.07 | 0.69 | 15.98 | 87.66 |
| Ex. 11 | (A-83) | 21.80 | 1.05 | 0.69 | 15.82 | 87.24 |
| Ex. 12 | (A-11) | 19.72 | 0.97 | 0.54 | 10.31 | 114.43 |
| Com. Ex. 2 | (B-1) | 20.11 | 1.06 | 0.62 | 13.26 | 69.87 |

It can be seen from the results in Table 2 that the devices for converting light into electricity each including, as the hole transport material, the compound (A-36), (A-37), (A-79), (A-96), (A-155), or (A-83) having the fluorenone skeleton, which is a compound of the present invention, exhibited higher efficiencies in conversion of light into electricity than the device including the compound (B-1), which is a standard hole transport material.

It can also be seen from the results in Table 2 that the devices for converting light into electricity each including, as the hole transport material, the compound (A-36), (A-37), (A-79), (A-96), (A-155), (A-83), or (A-11) having the fluorenone skeleton, which is a compound of the present invention, had better storage durability than the device including the compound (B-1), which is a standard hole transport material.

INDUSTRIAL APPLICABILITY

A device for converting light into electricity that includes the hole transport material according to the present invention has favorable power conversion efficiency, and can thus provide clean energy as a solar cell capable of efficiently converting solar energy into electrical energy. The device for converting light into electricity can also be used in other applications such as organic EL and image sensors.

LIST OF REFERENCE NUMERALS

1 Conductive support
2 Electron transport layer
3 Light/electricity conversion layer
4 Hole transport layer
5 Counter electrode

The invention claimed is:
1. A compound represented by the general formula (1) below:

[Chem. 1]

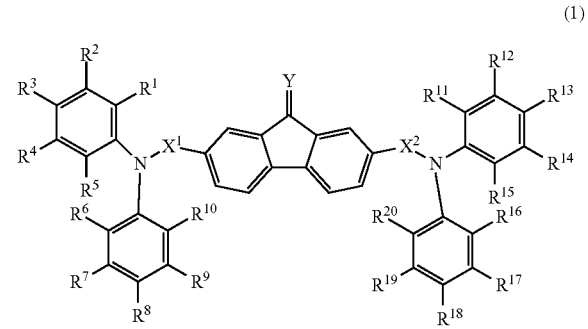

(1)

where $R^1$, $R^2$, $R^4$, $R^7$, $R^9$, $R^{10}$, $R^{11}$, $R^{12}$, $R^{14}$, $R^{17}$, $R^{19}$ and $R^{20}$ represent a hydrogen atom,
$R^5$, $R^6$, $R^{15}$, $R^{16}$ represent a hydrogen atom, and $R^3$, $R^8$, $R^{13}$ and $R^{18}$ represent an alkoxy group with 1 to 20 carbon atoms; or $R^5$ and $R^6$; and $R^{15}$ and $R^{16}$ are, in each combination, bonded to each other to form a ring via a single bond, and $R^3$, $R^8$, $R^{13}$ and $R^{18}$ represent a diphenylamino group substituted with an alkoxy group having 1 to 20 carbon atoms;
$X^1$ and $X^2$ each represent a divalent group represented by the general formula (2) below; and
Y represents $CR^{21}R^{22}$,
where $R^{21}$ and $R^{22}$ each independently represent an acyl group having 1 to 10 carbon atoms and optionally having a substituent, or an alkoxycarbonyl group having 1 to 10 carbon atoms and optionally having a substituent,

[Chem. 2]

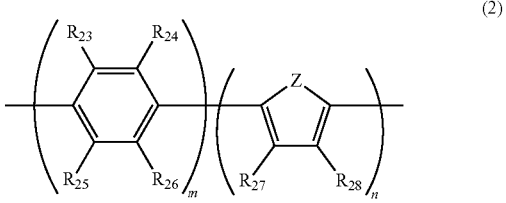

(2)

where $R^{23}$ to $R^{28}$ each independently represent a hydrogen atom, a linear or branched alkyl group having 1 to 10 carbon atoms and optionally having a substituent, a linear or branched alkenyl group having 2 to 10 carbon atoms and optionally having a substituent, a cycloalkyl group having 3 to 10 carbon atoms and optionally having a substituent, an aromatic hydrocarbon group having 6 to 18 carbon atoms and optionally having a substituent, or a heterocyclic group having 5 to 18 ring-forming atoms and optionally having a substituent;

$R^{23}$ and $R^{24}$; $R^{25}$ and $R^{26}$; and $R^{27}$ and $R^{28}$ are, in each combination, optionally bonded to each other to form a ring;

Z represents an oxygen atom, a sulfur atom, or a selenium atom; and m and n represent integers of 0 to 2, with the proviso that cases where both m and n are 0 are excluded.

2. The compound as set forth in claim 1, wherein, in the general formula (2), m is 1.

3. A hole transport material comprising the compound as set forth in claim 1.

4. A device for converting light into electricity, comprising the hole transport material as set forth in claim 3.

* * * * *